(12) United States Patent
Wang

(10) Patent No.: US 10,723,764 B2
(45) Date of Patent: *Jul. 28, 2020

(54) ANTI-MICROBIAL PEPTIDES AND METHODS OF USE THEREOF

(71) Applicant: Board of Regents of the University of Nebraska, Lincoln, NE (US)

(72) Inventor: Guangshun Wang, Omaha, NE (US)

(73) Assignee: BOARD OF REGENTS OF THE UNIVERSITY OF NEBRASKA, Lincoln, NE (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/700,908

(22) Filed: Apr. 30, 2015

(65) Prior Publication Data
US 2015/0259382 A1 Sep. 17, 2015

Related U.S. Application Data

(63) Continuation-in-part of application No. 14/358,340, filed as application No. PCT/US2012/066085 on Nov. 20, 2012, now Pat. No. 9,580,472.

(60) Provisional application No. 61/561,990, filed on Nov. 21, 2011, provisional application No. 61/986,191, filed on Apr. 30, 2014.

(51) Int. Cl.
C07K 7/08 (2006.01)
A61K 45/06 (2006.01)
A61K 38/00 (2006.01)

(52) U.S. Cl.
CPC .............. *C07K 7/08* (2013.01); *A61K 45/06* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 4,683,195 A | 7/1987 | Mullis | |
| 4,965,188 A | 10/1990 | Mullis | |
| 5,294,605 A | 3/1994 | Houghten et al. | |
| 5,789,542 A | 8/1998 | McLaughlin et al. | |
| 5,847,047 A | 12/1998 | Haynie et al. | |
| 7,453,964 B2 | 11/2008 | Pasqualini et al. | |
| 7,465,784 B2* | 12/2008 | Wang | C07K 14/4723 530/326 |
| 7,985,836 B2* | 7/2011 | Wang | C07K 14/4723 530/326 |
| 8,722,616 B2* | 5/2014 | Wang | A61K 38/04 514/1.1 |
| 9,580,472 B2* | 2/2017 | Wang | H02K 51/00 |
| 2002/0151678 A1 | 10/2002 | Arlinghaus | |
| 2003/0022829 A1 | 1/2003 | Maury et al. | |
| 2004/0086535 A1 | 5/2004 | Maury et al. | |
| 2006/0223755 A1 | 10/2006 | Grote | |
| 2007/0037744 A1 | 2/2007 | Gallo et al. | |
| 2009/0005300 A1 | 1/2009 | Hodges et al. | |
| 2012/0237501 A1* | 9/2012 | Wang | A61K 38/04 424/130.1 |

FOREIGN PATENT DOCUMENTS

| | | |
|---|---|---|
| WO | 2004058798 | 7/2004 |
| WO | 20041058789 | 7/2004 |
| WO | 2004/067563 | 8/2004 |
| WO | 2005/040192 | 5/2005 |
| WO | 20051040201 | 5/2005 |
| WO | 20061064514 | 6/2006 |
| WO | 20061064516 | 6/2006 |
| WO | 2007/148078 | 12/2007 |

OTHER PUBLICATIONS

Wang, G. NMR Studies of a Model Antimicrobial Peptide in the Micelles of SDS, Dodecylphosphocholine, or Dioctanoylphosphatidylglycerol, Open Magnetic Resonance Journal, 2005, 9-15. 1.
Wang, G., et al. APD2: the updated antimicrobial peptide database and its application in peptide design, Nucleic Acids Res., 2008, D933-7, 37.
The Antimicrobial Peptide Database. <http://http://aps.unmc.edu/AP/main.php> Oct. 28, 2008.
Murakami, M., et al. Postsecretory processing generates multiple cathelicidins for enhanced topical antimicrobial defense. J Immunol. Mar. 1, 2004 3070-7, 172(5).
Skerlavaj, B., et al. Biological characterization of two novel cathelicidin-derived peptides and identification of requirements for their antimicrobial and cell lytic activities. J Biol Chem. Nov. 8, 1996 28375-81, 271(45).
Zanetti, M., et al. Cathelicidins, multifunctional peptides of the innate immunity. Leukoc Biol. Jan. 2004, 39-48, 75(1).
Mishra, B., et al., Ab Initio Design of Potent Anti-MRSA Peptides based on Database Filtering Technology, Am Chem Soc., Aug. 2012, 12426-12429, 134(30).
Chung, L.A., et al., Fluorescence Studies of the Secondary Structure and Orientation of a Model Ion Channel Peptide in Phospholipid Vesicles, Biochemistry, Jul. 1992, 6608-6616, 31.
GeneBank CAI99864.1. Jun. 3, 2006.
Wang, G., et al. Anti-human immunodeficiency virus type 1 activities of antimicrobial peptides derived from human and bovine cathelicidins. Antimicrob Agents Chemother. Sep. 2008, 3438-40, 52(9).
Steinstraesser, L., et al. Inhibition of early steps in the lentiviral replication cycle by cathelicidin host defense peptides. Retrovirology. Jan. 2, 2005, 2.
Bergman, P., et al. The antimicrobial peptide LL-37 inhibits HIV-1 replication. Curr HIV Res. Jul. 2007, 410-5, 5(4).
Papo et al., Effect of drastic sequence alteration and d-amino acid incorporation on the membrane binding behavior of lytic peptides, Biochemistry, 2004, 6393-6403, 43.
Piotto et al., Gradient-tailored excitation for single-quantum NMR spectroscopy of aqueous solutions, J. Biomol. NMR. 1992, 661-665, 2.

(Continued)

*Primary Examiner* — Maury A Audet
(74) *Attorney, Agent, or Firm* — Robert C. Netter, Jr.; Dann, Dorfman, Herrell & Skillman

(57) ABSTRACT

Anti-microbial peptides and methods of use are provided.

14 Claims, 21 Drawing Sheets

Figure 1A:
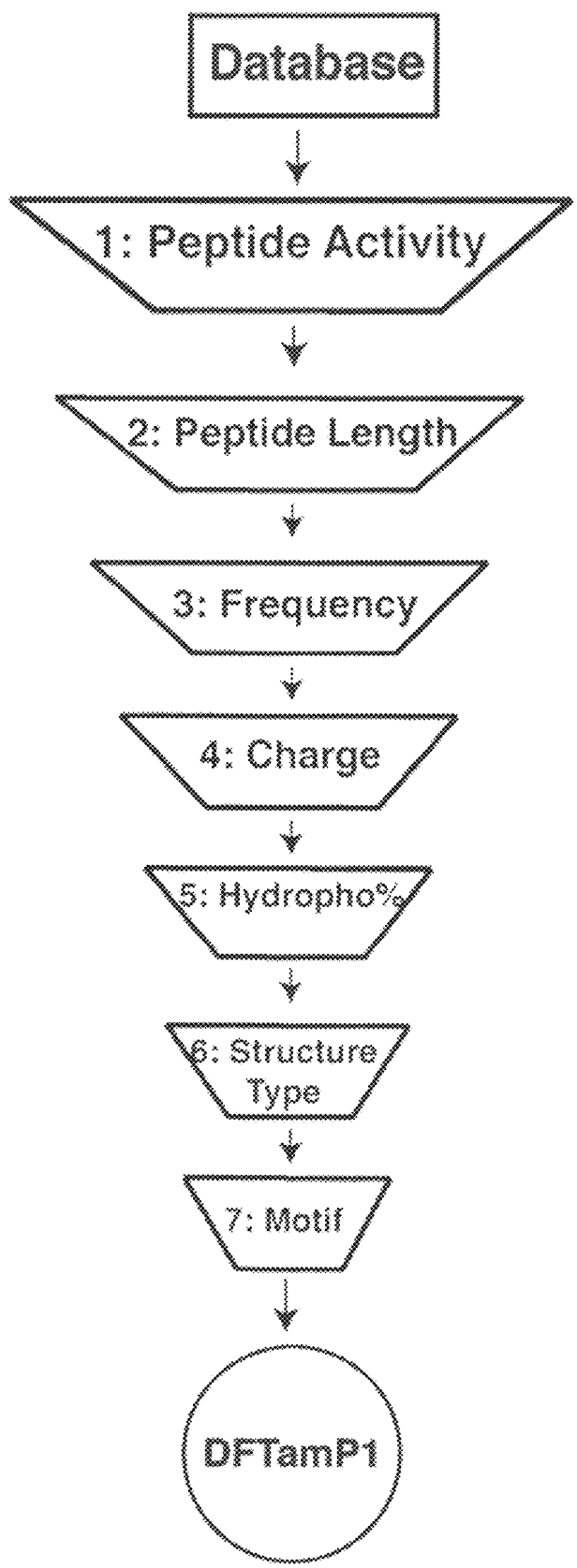
Figure 1B:
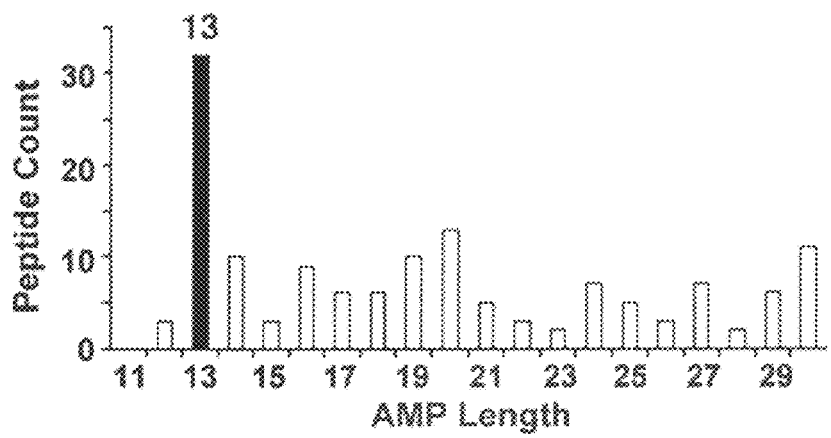
Figure 1C:
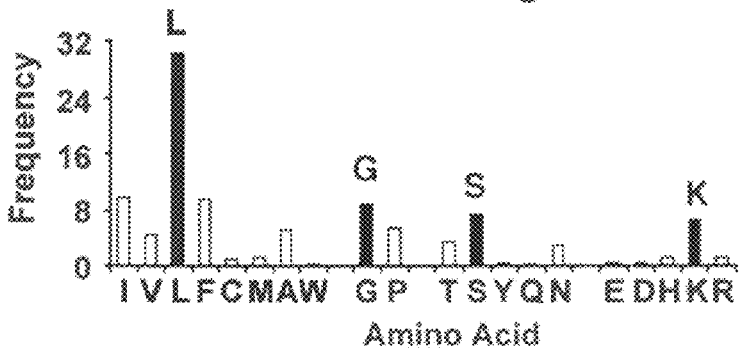
Figure 1D:
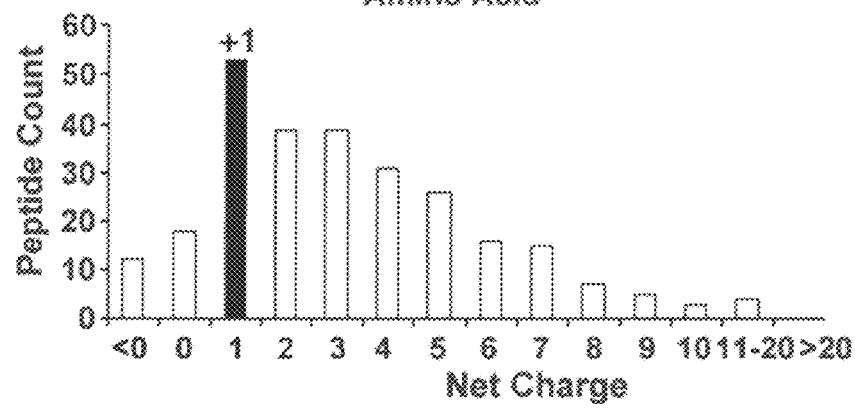

Specification includes a Sequence Listing.

(56) References Cited

OTHER PUBLICATIONS

Porcelli et al., Structure and orientation of parsdaxin determined by NMR experiments in model membranes, J. Biol. Chem., 2004, 45815-45823, 279.
Powers et al., Solution structure and interaction of the antimicrobial polyphemusins with lipid membranes, Biochemistry, 2005, 15504-15513, 44.
Putsep et al., Deficiency of antibacterial peptides in patients with morbus Kostmann: an observation study, Lancet, 2002, 1144-1149, 360.
Rance et al., Improved spectral resolution in COSY 1H NMR spectra of proteins via double quantum filtering, Biochem. Biophys. Res. Commun., 1983, 479-485, 117.
Rosenfeld et al., Endotoxin (lipopolysaccharide) neutralization by innate immunity host-defense peptides, J. Biol. Chem., 2006, 1636-1643, 281.
Rozek et al., The antibiotic and anticancer active aurein peptides from the Australian bell frogs *Litoria aurea* and *Litoria raniformis*, Eur. J. Biochem., 2000, 5330-5341, 267.
Schwieters, C.D., et al., The Xplor-NIH NMR molecular structure determination package, J. Magnetic Resonance, 2003, 65-73, 160.
Shai et al., Diastereomers of cytolysins, a novel class of potent antibacterial peptides, J. Biol. Chem., 1996, 7305-7308 271.
Sigurdardottir, T. et al., In Siulico Identification and Biological Evaluation of Antimicrobial Peptides Based on Human Cathelicidin LL-37; Antimicrobial Agents and Chemotherapy, 2006, 2983-2989, 50(9).
Sorenson et al., The human antibacterial cathelicidin, hCAP-18, is synthesized in myelocytes and metamyelocytes and localized to specific granules in neutrophils, Blood, 1997, 2796-2803, 90.
Spera et al., Empirical correlation between protein backbone conformation and Calpha and Cbeta 13C nuclear magentic resonance chemical shifts, J. Am. Chem. Soc., 1991, 5490-5492, 113.
Tjabringa et al., The antimicrobial peptide LL-37 activates innate immunity at the airway epithelial surface by transactivation of the epidermal growth factor receptor, J. Immunol., 2003, 6690-6696, 171.
Wang et al., Conformations of human apolipoprotein E(263-286) and E(267-289) in aqueous solutions of sodium dodecyl sulfate by CD and 1H NMR, J. Biochemistry, 1996, 10358-10366, 35.
Wang et al., Conformation of human serum apolipoprotein A-I(166-185) in the presence of sodium dodecyl sulfate or dodecylphosphocholine by 1H-NMR and CD. Evidence for specific peptide-SDS interactions, Biochimica et Biophysica Acta, 1996,174-184, 1301.
Wang et al., The helix-hinge-helix structural motif in human apolipoprotein A-I determined by NMR spectrocopy, J. Biochemistry, 1997, 13657-13666, 36.
Wang et al., A novel membrane anchor function for the N-terminal amphipathic sequence of the signal-transducing protein IIAglucose of the *Escherichia coli* phosphotransferase system, J. Biol. Chem., 2000, 39811-39814, 275.
Wang et al., A common interface on histidine-containing phospohcarrier protein for interaction with its partner proteins, J. Biol. Chem., 2000, 16401-16403, 275.
Wang, G. How the lipid-free structure of the N-terminal truncated human apoA-I converts to the lipid-bound form: new insights from NMR and X-ray structural comparison, FEBS Lett., 2002, 157-161, 529.
Wang et al., Solution structure of the N-terminal amphitropic domain of *Escherichia coli* glucose-specific enzyme IIA in membrane-mimetic micelles, Protein Sci., 2003, 1087-1096 and 1 cover sheet, 12.
Wang, G., et al. Short-chain diacyl phosphatidylglycerols: which one to choose for the NMR structural determination of a membrane-associated peptide from *Escherichia coli* ? Spectroscopy, 2004, 257-264, 18.
Wang et al., APD: the antimicrobial peptide database, Nucleic Acids Res., 2004, D590-D592, 32.

Wang et al. Correlation of three-dimensional structures with the antibacterial activity of a group of peptides designed based on a nontoxic bacterial membrane anchor, J. Biol. Chem., 2005, 5803-5811, 280.
Wang, G., Structural biology of antimicrobial peptides by NMR spectroscopy, Current Organic Chemistry, 2006, 569-581, 10 (5).
Wishart et al., Relationship between nuclear magnetic resonance chemical shift and protein secondary structure, J. Mol. Biol., 1991, 311-333, 222.
Yu et al., Solution structure of a cathelicidin-derived antimicrobial peptide, CRAMP as determined by NMR spectroscopy, J. Pept. Res., 2002, 1-9, 60.
Zanetti, M., Cathelicidins, multifunctional peptides of the innate immunity, J. Leukoc. Biol., 2004, 39-48, 75.
Zasloff, M., Antimicrobial peptides of multicellular organisms, Nature; 2002, 389-395, 415.
Zhang et al., Binding of peptides with basic and aromatic residues to bilayer membranes, J. Biol. Chem., 2003, 21459-21466, 278.
Agerberth et al., The human antimicrobial and chemotactic peptides LL-37 and alpha-defensins are expressed by specific lymphocyte and monocyte populations, Blood, 2000, 3086-3093, 96(9).
Allen et al., Structure of gramicidin A in a lipid bilayer environment determined using molecular dynamics simulations and solid-state NMR data, J. Am. Chem. Soc., 2003, 9868-9877, 125.
Bax et al., MLEV-17-based two-dimensional homonuclear magnetization transfer spectroscopy, J. Magn. Reson., 1985, 355-360, 65.
Bechinger, B., Detergent-like properties of magainin antibiotic peptides: A 31P solid-state NMR spectroscopy study, Biochimica et Biophysica Acta, 2005, 101-108, 1712.
Bowdish et al., The human cationic peptide LL-37 induces activation of the extracellular signal-regulated kinase and p38 kinase pathways in primary human monocytes, J. Immunol., 2004, 3758-3765, 172.
Braff et al., Structure-function relationships among human cathelicidin peptides: dissociation of antimicrobial properties from host immunostimulatory activities, J. Immunol., 2005, 4271-4278, 174.
Brahmachary et al., ANTIMIC: a database of antimicrobial sequences, Nucleic Acids Res., 2004, D586-589, 32.
Burley et al., Aromatic-aromatic interaction: a mechanism of protein structure stabilization, Science, 1985, 23-28 and one sheet of abstract, 229.
Chen et al., Rational design of alpha-helical antimicrobial peptides with enhanced activities and specificicty/therapeutic index, J. Biol. Chem., 2005, 12316-12329, 280.
Clore et al., Determining the structures of large proteins and protein complexes by NMR, Trends Biotechnol., 1998, 22-34, 16.
Cornilescu et al., Protein backbone angle restraints from searching a database for chemical shift and sequence homology, J. Biomol. NMR, 1999, 289-302, 13.
Delagio et al., NMRPipe: a mutlidimensional spectral processing system based on UNIX pipes, J. Biomol. NMR, 1995, 277-293, 6.
Di Nardo et al., Cutting edge: mast cell antimicrobial activity is mediated by expression of cathelicidin antimicrobial peptide, J. Immunol., 2003, 2274-2278, 170.
Dorschner et.al., Cutaneous injury induces the release of cathelicidin anti-microbial peptides active against group A *Steptococcus*, Invest. Dermatol., 2001, 91-97, 117.
Frohm et al., The expression of the gene coding for the antibacterial peptide LL-37 is induced in human keratinocytes during inflammatory disorders, J. Biol.Chem., 1997, 15258-15263, 272.
Garrett et al., A common sense approach to peak picking in two-, three-, and four-dimensional spectra using automatic computer analysis of contour diagrams, J. Magn. Reson., 1991, 214-220, 95.
Griesinger et al., Clean TOCSY for 1H spin system identification in macromolecules, J. Am. Chem. Soc., 1998, 7870-7872, 110.
Gudmundsson et al., The human gene FALL39 and processing of the cathelin precursor to the antibacterial peptide LL-37 in granulocytes, Eur. J. Biochem., 1996, 325-332, 238.
Hallock et al., Membrane composition determines pardaxin's mechanism of lipid bilayer disruption, Biophys. J., 2002, 1004-1013, 83.
Hansen et al., Re-examination and further development of a precise and rapid dye method for measuring cell growth/cell kill, J. Immunol. Methods, 1989, 203-210, 199.

(56) References Cited

OTHER PUBLICATIONS

Henry et al. Methods to study membrane protein structure in solution, Methods Enzymol, 1994, 515-535, 239.

Henzler-Wildman et al., Mechanism of lipid bilayer disruption by the human antimicrobial peptide, LL-37, Biochemistry, 2003, 6545-6558, 42.

Henzler-Wildman et al., Peturbation of the hydrophobic core of lipid bilayers by the human antimicrobial peptide LL-37, Biochemistry, 2004, 8459-8469, 43.

Oren et al., Structures and mode of membrane interaction of a short alpha helical lytic peptide and its diastereomer determined by NMR, FTIR, and fluorescence spectroscopy, Eur. J. Biochem., 2002, 3869-3880, 269.

Johansson et al., Conformation-dependent antibacteiral activity of the naturally occurring human peptide LL-37, J. Biol. Chem., 1998, 3718-3724, 273.

Kay et al. Pure absorption gradient enhanced heteronuclear single quantum correlation spectroscopy with improved sensitivity, J. Am Chem. Soc.,1992, 10663-10665, 114.

Keifer et al., Effects of detergent alkyl chain length and chemical structure on the properties of a micelle-bound bacterial membrane targeting peptide, Anal. Biochem., 2004, 33-39, 331.

Kim et al., Correlation between the activities of alpha-helical antimicrobial peptides and hydrophobicities represented as RP HPLC retention times, J. Peptides, 2005, 2050-2056, 26.

Koradi, R., et al., MOLMOL: a program for display and analysis of macromolecular structures, J. Mol. Graphics, 1996, 51-55, 14.

Laskowski, R.A., et al., Procheck: a program to check the stereochemical quality of protein structures, J. Appl. Cryst., 1993, 283-291, 26.

Lee et al., Expression of an additional cathelcidin antimicrobial peptide protects against bacterial skin infection, Proc. Natl. Acad. Sci. U.S.A., 2005, 3750-3755, 102.

Li et al., Cloning, expression, isotope labeling, and purification of human antimicrobial peptide LL-37 in *Escherichia coli* for NMR studies, Protein Exp. Purif., 2006, 498-505, 47.

Li et al., Solution structures of human LL-37 fragments and NMR-based identification of a minimal membrane-targeting antimicrobial and anticancer region, J. Am. Chem. Soc., 2006, 5776-5785, 128.

Li, X. et al., NMR Studies of Aurein 1.2 Analogs, Biochimica et Biophysica Acta; 2006, 1203-14, 1758.

Sieprawska-Lupa et al.; Degradation of human antimicrobial peptide LL-37 by *Staphylococcus aureus*-derived proteinases, Antimicrob. Agents Chemother, 2004, 4673-4679, 48.

Mani, R., et al., Membrane-disruptive abilities of beta-hairpin antimicrobial peptides correlate with conformation and activity: A 31P and 1H NMR study, Biochimica et Biophysica Acta, 2005, 11-18, 1716.

Mark, K.S., et al., Increased permeability of primary cultured brain microvessel endothelial cell monolayers following TNF-alpha exposure, Life Sci., 1999, 1941-1953, 64(21).

Markley et al., Recommendations for the presentation of NMR structures of proteins and nucleic acids, J. Biomol. NMR, 1998, 1-23, 12.

McPhee et al, Function and therapeutic potential of host defence peptides, J. Pept. Sci., 2005, 677-687, 11.

Mecke et al., Membrane thinning due to antimicrobial peptide binding: an atomic force microscopy study of MSI-78 in lipid bilayers, Biophys. J., 2005, 4043-4050, 89.

Mitchell et al., D-amino acid residues in peptides and proteins, Proteins, 563-571, 50.

Murakami et al., Postsecretory processing generates multiple cathelicidins for enhanced topical antimicrobial defense, J. Immunol., 2004, 3070-3077, 172.

Mygind et al., Plectasin is a peptide antibiotic with therapeutic potential from a saprophytic fungus, Nature, 2005, 975-980, 435.

Nagaoka et al., Augmentation of the lipopolysaccharide-neutralizing activities of human cathelicidin CAP18/fLL-37-derived antimicrobial peptides by replacement with hydrophobic and cationic amino acid residues, Clin. Diagn. Lab. Immunol., 2002, 972-982, 9.

Nell et al., Development of novel LL-37 derived antimicrobial peptides with LPS adn LTA neutralizing and antimicrobial activities for therapeutic application, Peptides, 2006, 649-660, 27.

Nizet et al., Innate antimicrobial peptide protects the skin from invasive bacterial infection, Nature, 2001, 454-457, 414.

Opella et al., Structure determination of membrane proteins by NMR spectroscopy, Chem. Rev., 2004, 3587-3606, 104.

Oren et al., Selective lysis of bacteria but not mammalian cells by diastereomers of melittin: structure-function study, Biochemistry, 1997, 1826-1835, 36.

Oren et al., Structure and organization of the human antimicrobial peptide LL-37 in phospholipid membranes: relevance to the molecular basis for its non-cell-selective activity, Biochem. J., 1996, 501-513, 341.

Wang, et al., "Amino Acid Composition Determines Peptide Activity Spectrum and Hot-Spot-Based Design of Merecidin" Adv. Biosys. (2018) 1700259.

International Preliminary Report on Patentability, PCT/US2012/066085, dated May 27, 2014.

\* cited by examiner

Catheter Day 3

Tissue Day 3

Catheter Day 14

Tissue Day 14

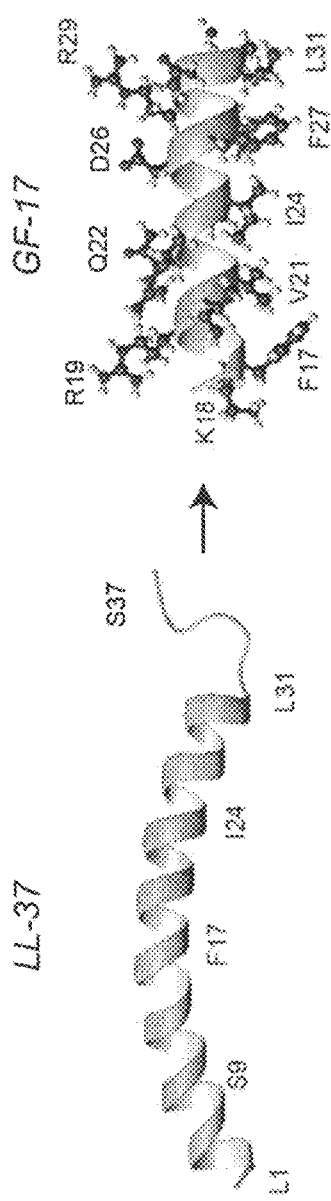
Figure 8A
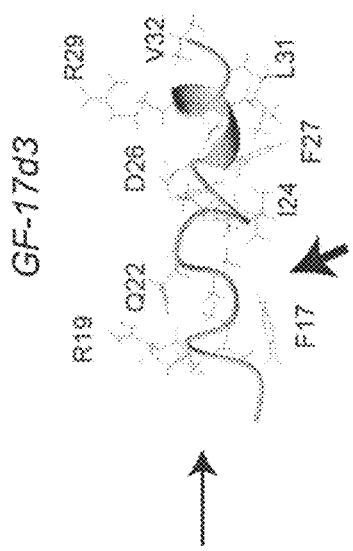
Figure 8B
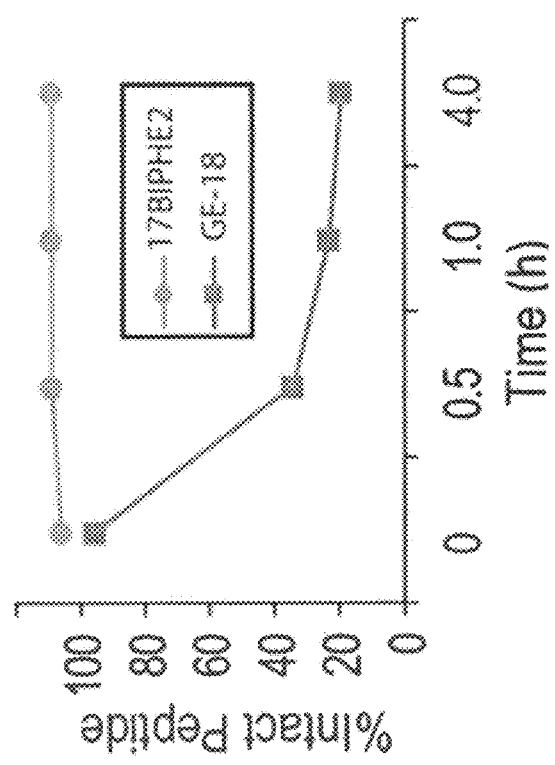
Figure 8C
Figure 8E
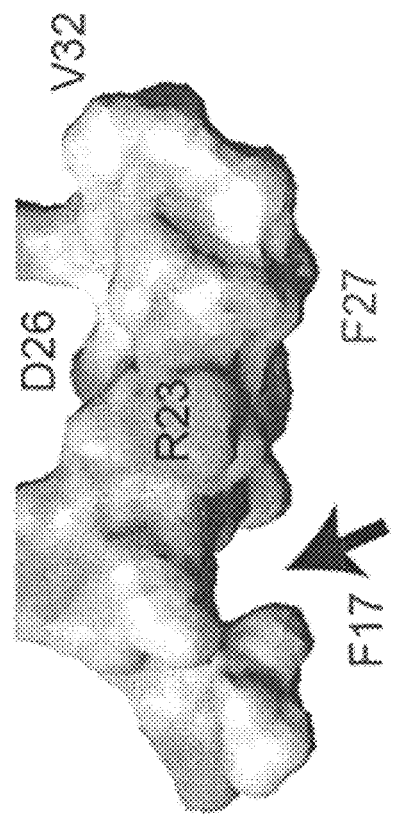
Figure 8D 1  2  3  4  5  6  7  8  9  10  11  12  13  14  15

SEQUENCE LISTING

<160> NUMBER OF SEQ ID NOS: 70

<210> SEQ ID NO 1
<211> LENGTH: 13
<212> TYPE: PRT
<213> ORGANISM: Artificial Sequence
<220> FEATURE:
<223> OTHER INFORMATION: Synthetic sequence

<400> SEQUENCE: 1

Gly Leu Leu Ser Leu Leu Ser Leu Leu Gly Lys Leu Leu
1               5                   10

<210> SEQ ID NO 2
<211> LENGTH: 13
<212> TYPE: PRT
<213> ORGANISM: Artificial Sequence
<220> FEATURE:
<223> OTHER INFORMATION: Synthetic sequence

<400> SEQUENCE: 2

Gly Leu Leu Pro Leu Leu Ser Leu Leu Gly Lys Leu Leu
1               5                   10

<210> SEQ ID NO 3
<211> LENGTH: 13
<212> TYPE: PRT
<213> ORGANISM: Artificial Sequence
<220> FEATURE:
<223> OTHER INFORMATION: Synthetic sequence

<400> SEQUENCE: 3

Gly Ile Ile Pro Ile Ile Ser Ile Ile Gly Lys Ile Ile
1               5                   10

<210> SEQ ID NO 4
<211> LENGTH: 13
<212> TYPE: PRT
<213> ORGANISM: Artificial Sequence
<220> FEATURE:
<223> OTHER INFORMATION: Synthetic sequence

<400> SEQUENCE: 4

Gly Val Val Pro Val Val Ser Val Val Gly Lys Val Val
1               5                   10

<210> SEQ ID NO 5
<211> LENGTH: 13
<212> TYPE: PRT
<213> ORGANISM: Hylarana picturata

<400> SEQUENCE: 5

Phe Phe Gly Ser Val Leu Lys Leu Ile Pro Lys Ile Leu
1               5                   10

<210> SEQ ID NO 6
<211> LENGTH: 13
<212> TYPE: PRT
<213> ORGANISM: Artificial Sequence
<220> FEATURE:
<223> OTHER INFORMATION: Synthetic sequence
<220> FEATURE:
<221> NAME/KEY: MOD_RES
<222> LOCATION: (1)...(13)
<223> OTHER INFORMATION: D-amino acids

<400> SEQUENCE: 6

Phe Phe Gly Ser Val Leu Lys Leu Ile Pro Lys Ile Leu
1               5                   10

<210> SEQ ID NO 7
<211> LENGTH: 13
<212> TYPE: PRT
<213> ORGANISM: Artificial Sequence
<220> FEATURE:
<223> OTHER INFORMATION: Synthetic sequence

<400> SEQUENCE: 7

Phe Phe Gly Ser Leu Leu Lys Leu Leu Pro Lys Leu Leu
1               5                   10

<210> SEQ ID NO 8
<211> LENGTH: 13
<212> TYPE: PRT
<213> ORGANISM: Artificial Sequence
<220> FEATURE:
<223> OTHER INFORMATION: Synthetic sequence

<400> SEQUENCE: 8

Leu Leu Gly Ser Leu Leu Lys Leu Leu Pro Lys Leu Leu
1               5                   10

<210> SEQ ID NO 9
<211> LENGTH: 13
<212> TYPE: PRT
<213> ORGANISM: Artificial Sequence
<220> FEATURE:
<223> OTHER INFORMATION: Synthetic sequence

<400> SEQUENCE: 9

Phe Phe Gly Lys Val Leu Lys Leu Ile Arg Lys Ile Phe
1               5                   10

<210> SEQ ID NO 10
<211> LENGTH: 8
<212> TYPE: PRT
<213> ORGANISM: Pelophylax saharicus

<400> SEQUENCE: 10

Phe Phe Phe Leu Ser Arg Ile Phe
1               5

<210> SEQ ID NO 11
<211> LENGTH: 13
<212> TYPE: PRT
<213> ORGANISM: Rana temporaria

<400> SEQUENCE: 11

Phe Val Gln Trp Phe Ser Lys Phe Leu Gly Arg Ile Leu
1               5                   10

<210> SEQ ID NO 12
<211> LENGTH: 13
<212> TYPE: PRT
<213> ORGANISM: Rana temporaria

<400> SEQUENCE: 12

Phe Phe Pro Val Ile Gly Arg Ile Leu Asn Gly Ile Leu
1               5                   10

<210> SEQ ID NO 13
<211> LENGTH: 14
<212> TYPE: PRT

<213> ORGANISM: Rana luteiventris

<400> SEQUENCE: 13

Asn Phe Leu Gly Thr Leu Ile Asn Leu Ala Lys Lys Ile Met
1               5                   10

<210> SEQ ID NO 14
<211> LENGTH: 13
<212> TYPE: PRT
<213> ORGANISM: Rana temporaria

<400> SEQUENCE: 14

Phe Leu Pro Leu Ile Gly Arg Val Leu Ser Gly Ile Leu
1               5                   10

<210> SEQ ID NO 15
<211> LENGTH: 13
<212> TYPE: PRT
<213> ORGANISM: Rana temporaria

<400> SEQUENCE: 15

Phe Leu Pro Leu Ile Gly Lys Val Leu Ser Gly Ile Leu
1               5                   10

<210> SEQ ID NO 16
<211> LENGTH: 13
<212> TYPE: PRT
<213> ORGANISM: Rana temporaria

<400> SEQUENCE: 16

Val Leu Pro Ile Ile Gly Asn Leu Leu Asn Ser Leu Leu
1               5                   10

<210> SEQ ID NO 17
<211> LENGTH: 10
<212> TYPE: PRT
<213> ORGANISM: Rana temporaria

<400> SEQUENCE: 17

Leu Ser Pro Asn Leu Leu Lys Ser Leu Leu
1               5                   10

<210> SEQ ID NO 18
<211> LENGTH: 13
<212> TYPE: PRT
<213> ORGANISM: Rana temporaria

<400> SEQUENCE: 18

Leu Leu Pro Ile Val Gly Asn Leu Asn Ser Leu Leu
1               5                   10

<210> SEQ ID NO 19
<211> LENGTH: 13
<212> TYPE: PRT
<213> ORGANISM: Rana temporaria

<400> SEQUENCE: 19

Leu Leu Pro Ile Val Gly Asn Leu Leu Lys Ser Leu Leu
1               5                   10

<210> SEQ ID NO 20
<211> LENGTH: 10
<212> TYPE: PRT
<213> ORGANISM: Rana temporaria

```
<400> SEQUENCE: 20

Leu Leu Pro Asn Leu Leu Lys Ser Leu Leu
1               5                   10

<210> SEQ ID NO 21
<211> LENGTH: 13
<212> TYPE: PRT
<213> ORGANISM: Rana temporaria

<400> SEQUENCE: 21

Leu Leu Pro Ile Leu Gly Asn Leu Leu Asn Gly Leu Leu
1               5                   10

<210> SEQ ID NO 22
<211> LENGTH: 15
<212> TYPE: PRT
<213> ORGANISM: Palomena prasina

<400> SEQUENCE: 22

Val Asp Lys Pro Asp Tyr Arg Pro Arg Pro Arg Pro Pro Asn Met
1               5                   10                  15

<210> SEQ ID NO 23
<211> LENGTH: 14
<212> TYPE: PRT
<213> ORGANISM: Rana catesbeiana

<400> SEQUENCE: 23

Phe Leu Phe Pro Leu Ile Thr Ser Phe Leu Ser Lys Val Leu
1               5                   10

<210> SEQ ID NO 24
<211> LENGTH: 14
<212> TYPE: PRT
<213> ORGANISM: Vespa mandarinia

<400> SEQUENCE: 24

Ile Asn Leu Lys Ala Ile Ala Ala Leu Ala Lys Lys Leu Leu
1               5                   10

<210> SEQ ID NO 25
<211> LENGTH: 14
<212> TYPE: PRT
<213> ORGANISM: Phyllomedusa hypochondrialis

<400> SEQUENCE: 25

Phe Arg Pro Ala Leu Ile Val Arg Thr Lys Gly Thr Arg Leu
1               5                   10

<210> SEQ ID NO 26
<211> LENGTH: 18
<212> TYPE: PRT
<213> ORGANISM: Apis mellifera

<400> SEQUENCE: 26

Gly Asn Asn Arg Pro Val Tyr Ile Pro Gln Pro Arg Pro Pro His Pro
1               5                   10                  15

Arg Ile

<210> SEQ ID NO 27
<211> LENGTH: 19
<212> TYPE: PRT
<213> ORGANISM: Drosophila melanogaster
```

-continued

```
<400> SEQUENCE: 27

Gly Lys Pro Arg Pro Tyr Ser Pro Arg Pro Thr Ser His Pro Arg Pro
1               5                   10                  15

Ile Arg Val

<210> SEQ ID NO 28
<211> LENGTH: 21
<212> TYPE: PRT
<213> ORGANISM: Xenopus laevis

<400> SEQUENCE: 28

Gly Met Ala Ser Lys Ala Gly Ala Ile Ala Gly Lys Ile Ala Lys Val
1               5                   10                  15

Ala Leu Lys Ala Leu
            20

<210> SEQ ID NO 29
<211> LENGTH: 23
<212> TYPE: PRT
<213> ORGANISM: Styela clava

<400> SEQUENCE: 29

Val Phe Gln Phe Leu Gly Arg Ile Ile His His Val Gly Asn Phe Val
1               5                   10                  15

His Gly Phe Ser His Val Phe
            20

<210> SEQ ID NO 30
<211> LENGTH: 21
<212> TYPE: PRT
<213> ORGANISM: Bufo bufo

<400> SEQUENCE: 30

Thr Arg Ser Ser Arg Ala Gly Leu Gln Phe Pro Val Gly Arg Val His
1               5                   10                  15

Arg Leu Leu Arg Lys
            20

<210> SEQ ID NO 31
<211> LENGTH: 19
<212> TYPE: PRT
<213> ORGANISM: Styela clava

<400> SEQUENCE: 31

Gly Phe Gly Lys Ala Phe His Ser Val Ser Asn Phe Ala Lys Lys His
1               5                   10                  15

Lys Thr Ala

<210> SEQ ID NO 32
<211> LENGTH: 24
<212> TYPE: PRT
<213> ORGANISM: Pachycondyla goeldii

<400> SEQUENCE: 32

Leu Leu Lys Glu Leu Trp Thr Lys Ile Lys Gly Ala Gly Lys Ala Val
1               5                   10                  15

Leu Gly Lys Ile Lys Gly Leu Leu
            20

<210> SEQ ID NO 33
<211> LENGTH: 25
```

```
<212> TYPE: PRT
<213> ORGANISM: Pseudacanthotermes spiniger

<400> SEQUENCE: 33

His Val Asp Lys Lys Val Ala Asp Lys Val Leu Leu Leu Lys Gln Leu
1               5                   10                  15

Arg Ile Met Arg Leu Leu Thr Arg Leu
            20                  25

<210> SEQ ID NO 34
<211> LENGTH: 22
<212> TYPE: PRT
<213> ORGANISM: Morone saxatilis

<400> SEQUENCE: 34

Phe Phe His His Ile Phe Arg Gly Ile Val His Val Gly Lys Thr Ile
1               5                   10                  15

His Arg Leu Val Thr Gly
            20

<210> SEQ ID NO 35
<211> LENGTH: 24
<212> TYPE: PRT
<213> ORGANISM: Pseudis paradoxa

<400> SEQUENCE: 35

Gly Leu Asn Thr Leu Lys Lys Val Phe Gln Gly Leu His Glu Ala Ile
1               5                   10                  15

Lys Leu Ile Asn Asn His Val Gln
            20

<210> SEQ ID NO 36
<211> LENGTH: 21
<212> TYPE: PRT
<213> ORGANISM: Misgurnus anguillicaudatus

<400> SEQUENCE: 36

Arg Gln Arg Val Glu Glu Leu Ser Lys Phe Ser Lys Lys Gly Ala Ala
1               5                   10                  15

Ala Arg Arg Arg Lys
            20

<210> SEQ ID NO 37
<211> LENGTH: 25
<212> TYPE: PRT
<213> ORGANISM: Hogna carolinensis

<400> SEQUENCE: 37

Ile Trp Leu Thr Ala Leu Lys Phe Leu Gly Lys His Ala Ala Lys His
1               5                   10                  15

Leu Ala Lys Gln Gln Leu Ser Lys Leu
            20                  25

<210> SEQ ID NO 38
<211> LENGTH: 19
<212> TYPE: PRT
<213> ORGANISM: Parasilurus asotus

<400> SEQUENCE: 38

Lys Gly Arg Gly Lys Gln Gly Gly Lys Val Arg Ala Lys Ala Lys Thr
1               5                   10                  15

Arg Ser Ser
```

```
<210> SEQ ID NO 39
<211> LENGTH: 21
<212> TYPE: PRT
<213> ORGANISM: Lithobates septentrionalis

<400> SEQUENCE: 39

Gly Ile Trp Asp Thr Ile Lys Ser Met Gly Lys Val Phe Ala Gly Lys
1               5                   10                  15

Ile Leu Gln Asn Leu
            20

<210> SEQ ID NO 40
<211> LENGTH: 21
<212> TYPE: PRT
<213> ORGANISM: Litoria eucnemis

<400> SEQUENCE: 40

Gly Leu Leu Gly Leu Leu Gly Ser Val Val Ser His Val Val Pro Ala
1               5                   10                  15

Ile Val Gly His Phe
            20

<210> SEQ ID NO 41
<211> LENGTH: 20
<212> TYPE: PRT
<213> ORGANISM: Lachesana tarabaevi

<400> SEQUENCE: 41

Ser Trp Lys Ser Met Ala Lys Lys Leu Lys Glu Tyr Met Glu Lys Leu
1               5                   10                  15

Lys Gln Arg Ala
            20

<210> SEQ ID NO 42
<211> LENGTH: 25
<212> TYPE: PRT
<213> ORGANISM: Lactobacillus plantarum

<400> SEQUENCE: 42

Gly Ala Trp Lys Asn Phe Trp Ser Ser Leu Arg Lys Gly Phe Tyr Asp
1               5                   10                  15

Gly Glu Ala Gly Arg Ala Ile Arg Arg
            20                  25

<210> SEQ ID NO 43
<211> LENGTH: 19
<212> TYPE: PRT
<213> ORGANISM: Ascaphus truei

<400> SEQUENCE: 43

Gly Phe Lys Asp Leu Leu Lys Gly Ala Ala Lys Ala Leu Val Lys Thr
1               5                   10                  15

Val Leu Phe

<210> SEQ ID NO 44
<211> LENGTH: 19
<212> TYPE: PRT
<213> ORGANISM: Crinia deserticola

<400> SEQUENCE: 44

Gly Leu Ala Asp Phe Leu Asn Lys Ala Val Gly Lys Val Val Asp Phe
```

```
1               5                   10                  15

Val Lys Ser

<210> SEQ ID NO 45
<211> LENGTH: 18
<212> TYPE: PRT
<213> ORGANISM: Melecta albifrons

<400> SEQUENCE: 45

Gly Phe Leu Ser Ile Leu Lys Lys Val Leu Pro Lys Val Met Ala His
1               5                   10                  15

Met Lys

<210> SEQ ID NO 46
<211> LENGTH: 23
<212> TYPE: PRT
<213> ORGANISM: Bos taurus

<400> SEQUENCE: 46

Arg Pro Lys His Pro Ile Lys His Gln Gly Leu Pro Gln Glu Val Leu
1               5                   10                  15

Asn Glu Asn Leu Leu Arg Phe
            20

<210> SEQ ID NO 47
<211> LENGTH: 14
<212> TYPE: PRT
<213> ORGANISM: Artificial Sequence
<220> FEATURE:
<223> OTHER INFORMATION: Synthetic sequence

<400> SEQUENCE: 47

Ile Lys Trp Lys Lys Leu Leu Arg Ala Ala Lys Arg Ile Leu
1               5                   10

<210> SEQ ID NO 48
<211> LENGTH: 13
<212> TYPE: PRT
<213> ORGANISM: Artificial Sequence
<220> FEATURE:
<223> OTHER INFORMATION: Synthetic sequence

<400> SEQUENCE: 48

Gly Trp Phe Asp Val Val Lys His Ile Ala Lys Arg Phe
1               5                   10

<210> SEQ ID NO 49
<211> LENGTH: 25
<212> TYPE: PRT
<213> ORGANISM: Artificial Sequence
<220> FEATURE:
<223> OTHER INFORMATION: Synthetic sequence

<400> SEQUENCE: 49

Asn Leu Val Ser Gly Leu Ile Glu Ala Arg Lys Tyr Leu Glu Gln Leu
1               5                   10                  15

His Arg Lys Leu Lys Asn Arg Lys Val
            20                  25

<210> SEQ ID NO 50
<211> LENGTH: 17
<212> TYPE: PRT
<213> ORGANISM: Artificial Sequence
<220> FEATURE:
```

<223> OTHER INFORMATION: Synthetic sequence

<400> SEQUENCE: 50

Ser Leu Ser Arg Phe Leu Arg Phe Leu Lys Ile Val Tyr Arg Arg Ala
1               5                   10                  15
Phe

<210> SEQ ID NO 51
<211> LENGTH: 22
<212> TYPE: PRT
<213> ORGANISM: Artificial Sequence
<220> FEATURE:
<223> OTHER INFORMATION: Synthetic sequence

<400> SEQUENCE: 51

Ile Trp Leu Thr Ala Leu Lys Phe Leu Gly Lys His Ala Ala Lys His
1               5                   10                  15

Leu Ala Lys Gln Gln Leu
            20

<210> SEQ ID NO 52
<211> LENGTH: 18
<212> TYPE: PRT
<213> ORGANISM: Artificial Sequence
<220> FEATURE:
<223> OTHER INFORMATION: Synthetic sequence

<400> SEQUENCE: 52

Ile Trp Leu Thr Ala Leu Lys Phe Leu Gly Lys His Ala Ala Lys His
1               5                   10                  15

Leu Leu

<210> SEQ ID NO 53
<211> LENGTH: 13
<212> TYPE: PRT
<213> ORGANISM: Artificial Sequence
<220> FEATURE:
<223> OTHER INFORMATION: Synthetic sequence

<400> SEQUENCE: 53

Phe Phe Gly Arg Val Leu Arg Leu Ile Arg Arg Ile Phe
1               5                   10

<210> SEQ ID NO 54
<211> LENGTH: 22
<212> TYPE: PRT
<213> ORGANISM: Artificial Sequence
<220> FEATURE:
<223> OTHER INFORMATION: Synthetic sequence

<400> SEQUENCE: 54

Lys Ile Gly Lys Glu Phe Lys Arg Ile Val Gln Arg Ile Lys Asp Phe
1               5                   10                  15

Leu Arg Asn Leu Val Pro
            20

<210> SEQ ID NO 55
<211> LENGTH: 21
<212> TYPE: PRT
<213> ORGANISM: Artificial Sequence
<220> FEATURE:
<223> OTHER INFORMATION: Synthetic sequence

<400> SEQUENCE: 55

```
Gly Lys Glu Phe Lys Arg Ile Val Gln Arg Ile Lys Asp Phe Leu Arg
1               5                   10                  15

Asn Leu Val Pro Arg
            20
```

<210> SEQ ID NO 56
<211> LENGTH: 17
<212> TYPE: PRT
<213> ORGANISM: Artificial Sequence
<220> FEATURE:
<223> OTHER INFORMATION: Synthetic sequence

<400> SEQUENCE: 56

```
Gly Phe Lys Arg Ile Val Gln Arg Ile Lys Asp Phe Leu Arg Asn Leu
1               5                   10                  15

Val
```

<210> SEQ ID NO 57
<211> LENGTH: 17
<212> TYPE: PRT
<213> ORGANISM: Artificial Sequence
<220> FEATURE:
<223> OTHER INFORMATION: Synthetic sequence
<220> FEATURE:
<221> NAME/KEY: MOD_RES
<222> LOCATION: 5, 9, 13
<223> OTHER INFORMATION: D-amino acid

<400> SEQUENCE: 57

```
Gly Phe Lys Arg Ile Val Gln Arg Ile Lys Asp Phe Leu Arg Asn Leu
1               5                   10                  15

Val
```

<210> SEQ ID NO 58
<211> LENGTH: 17
<212> TYPE: PRT
<213> ORGANISM: Artificial Sequence
<220> FEATURE:
<223> OTHER INFORMATION: Synthetic sequence
<220> FEATURE:
<221> NAME/KEY: MOD_RES
<222> LOCATION: 2, 12
<223> OTHER INFORMATION: Xaa = any amino acid

<400> SEQUENCE: 58

```
Gly Xaa Lys Arg Leu Val Gln Arg Leu Lys Asp Xaa Leu Arg Asn Leu
1               5                   10                  15

Val
```

<210> SEQ ID NO 59
<211> LENGTH: 17
<212> TYPE: PRT
<213> ORGANISM: Artificial Sequence
<220> FEATURE:
<223> OTHER INFORMATION: Synthetic sequence
<220> FEATURE:
<221> NAME/KEY: MOD_RES
<222> LOCATION: 5, 9, 13
<223> OTHER INFORMATION: D-amino acid

<400> SEQUENCE: 59

```
Gly Phe Lys Arg Leu Val Gln Arg Leu Lys Asp Phe Leu Arg Asn Leu
1               5                   10                  15

Val
```

```
<210> SEQ ID NO 60
<211> LENGTH: 17
<212> TYPE: PRT
<213> ORGANISM: Artificial Sequence
<220> FEATURE:
<223> OTHER INFORMATION: Synthetic sequence
<220> FEATURE:
<221> NAME/KEY: MOD_RES
<222> LOCATION: 2
<223> OTHER INFORMATION: CF3-substituted phenylalanine
<220> FEATURE:
<221> NAME/KEY: MOD_RES
<222> LOCATION: 5, 9, 13
<223> OTHER INFORMATION: D-amino acid

<400> SEQUENCE: 60

Gly Xaa Lys Arg Leu Val Gln Arg Leu Lys Asp Phe Leu Arg Asn Leu
1               5                   10                  15

Val

<210> SEQ ID NO 61
<211> LENGTH: 17
<212> TYPE: PRT
<213> ORGANISM: Artificial Sequence
<220> FEATURE:
<223> OTHER INFORMATION: Synthetic sequence
<220> FEATURE:
<221> NAME/KEY: MOD_RES
<222> LOCATION: 2
<223> OTHER INFORMATION: Xaa = biphenylalanine
<220> FEATURE:
<221> NAME/KEY: MOD_RES
<222> LOCATION: 5, 9, 13
<223> OTHER INFORMATION: D-amino acid

<400> SEQUENCE: 61

Gly Xaa Lys Arg Leu Val Gln Arg Leu Lys Asp Phe Leu Arg Asn Leu
1               5                   10                  15

Val

<210> SEQ ID NO 62
<211> LENGTH: 17
<212> TYPE: PRT
<213> ORGANISM: Artificial Sequence
<220> FEATURE:
<223> OTHER INFORMATION: Synthetic sequence
<220> FEATURE:
<221> NAME/KEY: MOD_RES
<222> LOCATION: 2, 12
<223> OTHER INFORMATION: Xaa = biphenylalanine
<220> FEATURE:
<221> NAME/KEY: MOD_RES
<222> LOCATION: 5, 9, 13
<223> OTHER INFORMATION: D-amino acid

<400> SEQUENCE: 62

Gly Xaa Lys Arg Leu Val Gln Arg Leu Lys Asp Xaa Leu Arg Asn Leu
1               5                   10                  15

Val

<210> SEQ ID NO 63
<211> LENGTH: 13
<212> TYPE: PRT
<213> ORGANISM: Artificial Sequence
<220> FEATURE:
<223> OTHER INFORMATION: Synthetic sequence
<220> FEATURE:
<221> NAME/KEY: MOD_RES
<222> LOCATION: 1-4, 7, 10, 11
<223> OTHER INFORMATION: Xaa = any amino acid
```

<400> SEQUENCE: 63

Xaa Xaa Xaa Xaa Leu Leu Xaa Leu Leu Xaa Xaa Leu Leu
1               5                   10

<210> SEQ ID NO 64
<211> LENGTH: 20
<212> TYPE: PRT
<213> ORGANISM: Artificial Sequence
<220> FEATURE:
<223> OTHER INFORMATION: Synthetic Sequence

<400> SEQUENCE: 64

Phe Lys Arg Ile Val Gln Arg Ile Lys Asp Phe Leu Arg Asn Leu Val
1               5                   10                  15

Pro Arg Thr Glu
            20

<210> SEQ ID NO 65
<211> LENGTH: 20
<212> TYPE: PRT
<213> ORGANISM: Artificial Sequence
<220> FEATURE:
<223> OTHER INFORMATION: Synthetic Sequence

<400> SEQUENCE: 65

Glu Lys Ile Gly Lys Glu Phe Lys Arg Ile Val Gln Arg Ile Lys Asp
1               5                   10                  15

Phe Leu Arg Asn
            20

<210> SEQ ID NO 66
<211> LENGTH: 16
<212> TYPE: PRT
<213> ORGANISM: Artificial Sequence
<220> FEATURE:
<223> OTHER INFORMATION: Synthetic Sequence

<400> SEQUENCE: 66

Gly Phe Lys Arg Ile Val Gln Arg Ile Lys Asp Phe Leu Arg Asn Leu
1               5                   10                  15

<210> SEQ ID NO 67
<211> LENGTH: 18
<212> TYPE: PRT
<213> ORGANISM: Artificial Sequence
<220> FEATURE:
<223> OTHER INFORMATION: Synthetic Sequence

<400> SEQUENCE: 67

Gly Arg Phe Lys Arg Phe Arg Lys Lys Phe Lys Lys Leu Phe Lys Lys
1               5                   10                  15

Leu Ser

<210> SEQ ID NO 68
<211> LENGTH: 17
<212> TYPE: PRT
<213> ORGANISM: Artificial Sequence
<220> FEATURE:
<223> OTHER INFORMATION: Synthetic sequence
<220> FEATURE:
<221> NAME/KEY: MOD_RES
<222> LOCATION: 12
<223> OTHER INFORMATION: 2-naphthylalanine
<220> FEATURE:
<221> NAME/KEY: MOD_RES

```
<222> LOCATION: 5, 9, 13
<223> OTHER INFORMATION: D-amino acid

<400> SEQUENCE: 68

Gly Phe Lys Arg Leu Val Gln Arg Leu Lys Asp Xaa Leu Arg Asn Leu
1               5                   10                  15
Val

<210> SEQ ID NO 69
<211> LENGTH: 17
<212> TYPE: PRT
<213> ORGANISM: Artificial Sequence
<220> FEATURE:
<223> OTHER INFORMATION: Synthetic sequence
<220> FEATURE:
<221> NAME/KEY: MOD_RES
<222> LOCATION: 2
<223> OTHER INFORMATION: CF3-substituted phenylalanine
<220> FEATURE:
<221> NAME/KEY: MOD_RES
<222> LOCATION: 12
<223> OTHER INFORMATION: 2-naphthylalanine
<220> FEATURE:
<221> NAME/KEY: MOD_RES
<222> LOCATION: 5, 9, 13
<223> OTHER INFORMATION: D-amino acid

<400> SEQUENCE: 69

Gly Xaa Lys Arg Leu Val Gln Arg Leu Lys Asp Xaa Leu Arg Asn Leu
1               5                   10                  15
Val

<210> SEQ ID NO 70
<211> LENGTH: 17
<212> TYPE: PRT
<213> ORGANISM: Artificial Sequence
<220> FEATURE:
<223> OTHER INFORMATION: Synthetic sequence
<220> FEATURE:
<221> NAME/KEY: MOD_RES
<222> LOCATION: 12
<223> OTHER INFORMATION: CF3-substituted phenylalanine
<220> FEATURE:
<221> NAME/KEY: MOD_RES
<222> LOCATION: 2
<223> OTHER INFORMATION: 2-naphthylalanine
<220> FEATURE:
<221> NAME/KEY: MOD_RES
<222> LOCATION: 5, 9, 13
<223> OTHER INFORMATION: D-amino acid

<400> SEQUENCE: 70

Gly Xaa Lys Arg Leu Val Gln Arg Leu Lys Asp Xaa Leu Arg Asn Leu
1               5                   10                  15
Val
```

ANTI-MICROBIAL PEPTIDES AND METHODS OF USE THEREOF

This application is a continuation-in-part application of U.S. patent application Ser. No. 14/358,340, filed May 15, 2014, which is a § 371 of PCT/US12/66085, filed Nov. 20, 2012, which claims priority under 35 U.S.C. § 119(e) to U.S. Provisional Patent Application No. 61/561,990, Nov. 21, 2011. This application also claims priority under 35 U.S.C. § 119(e) to U.S. Provisional Patent Application No. 61/986,191, filed on Apr. 30, 2014. The foregoing applications are incorporated by reference herein.

This invention was made with government support under 1R56 AI081975-01A2 awarded by the National Institutes of Health. The government has certain rights in the invention.

FIELD OF THE INVENTION

The present invention relates to the field of antimicrobial peptides and the treatment of microbial infections. More specifically the invention provides anti-microbial peptides, methods of identifying the same, and methods of using such peptides for the treatment of microbial infections, particularly by ESKAPE pathogens.

BACKGROUND OF THE INVENTION

In the United States, methicillin-resistant *Staphylococcus aureus* (MRSA) caused 94,360 serious infections and 18,650 deaths in 2005. The number of annual deaths caused by MRSA infection is now higher than that caused by HIV/AIDS (Klevens et al. (2007) Public Health Rep., 122: 160-166). Bacterial resistance rendered traditional antibiotics ineffective, adding an unwanted burden to medical care. As a consequence, it is critical to develop a new generation of antibiotics that can eliminate superbugs such as MRSA by a mechanism different from those of traditional antibiotics.

SUMMARY OF THE INVENTION

In accordance with one aspect of the instant invention, anti-microbial peptides are provided. In a particular embodiment, the anti-microbial peptide has at least 90% homology with SEQ ID NO: 58 or any anti-microbial peptide disclosed herein. Compositions comprising at least one anti-microbial peptide of the instant invention and at least one pharmaceutically acceptable carrier are also provided. The compositions may further comprise at least one other anti-microbial compound (e.g., antibiotic).

In accordance with another aspect of the instant invention, method for inhibiting, treating, and/or preventing a microbial infection in a subject are provided. The methods comprise administering to a subject at least one peptide of the instant invention, particularly as a composition with a carrier. In a particular embodiment, the methods further comprise the administration at least one other anti-microbial treatment, such as the administration of at least one additional antibiotic.

In accordance with another aspect of the instant invention, methods for creating anti-microbial peptides are provided.

BRIEF DESCRIPTIONS OF THE DRAWING

Figure 1E:
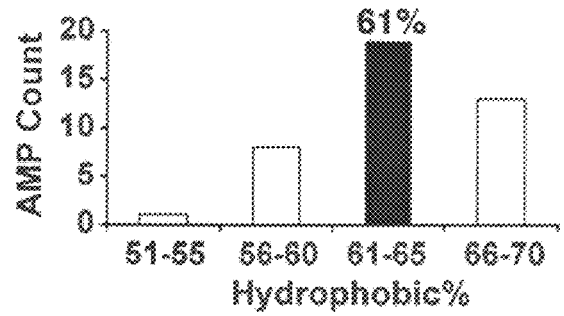
Figure 1F:
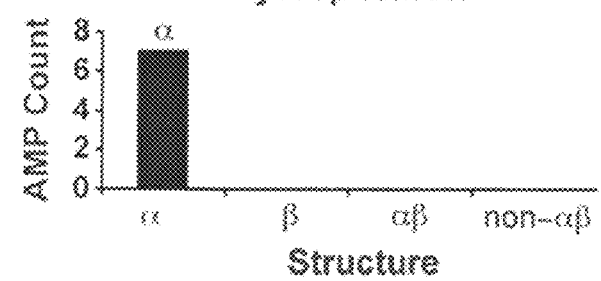
Figure 1G:
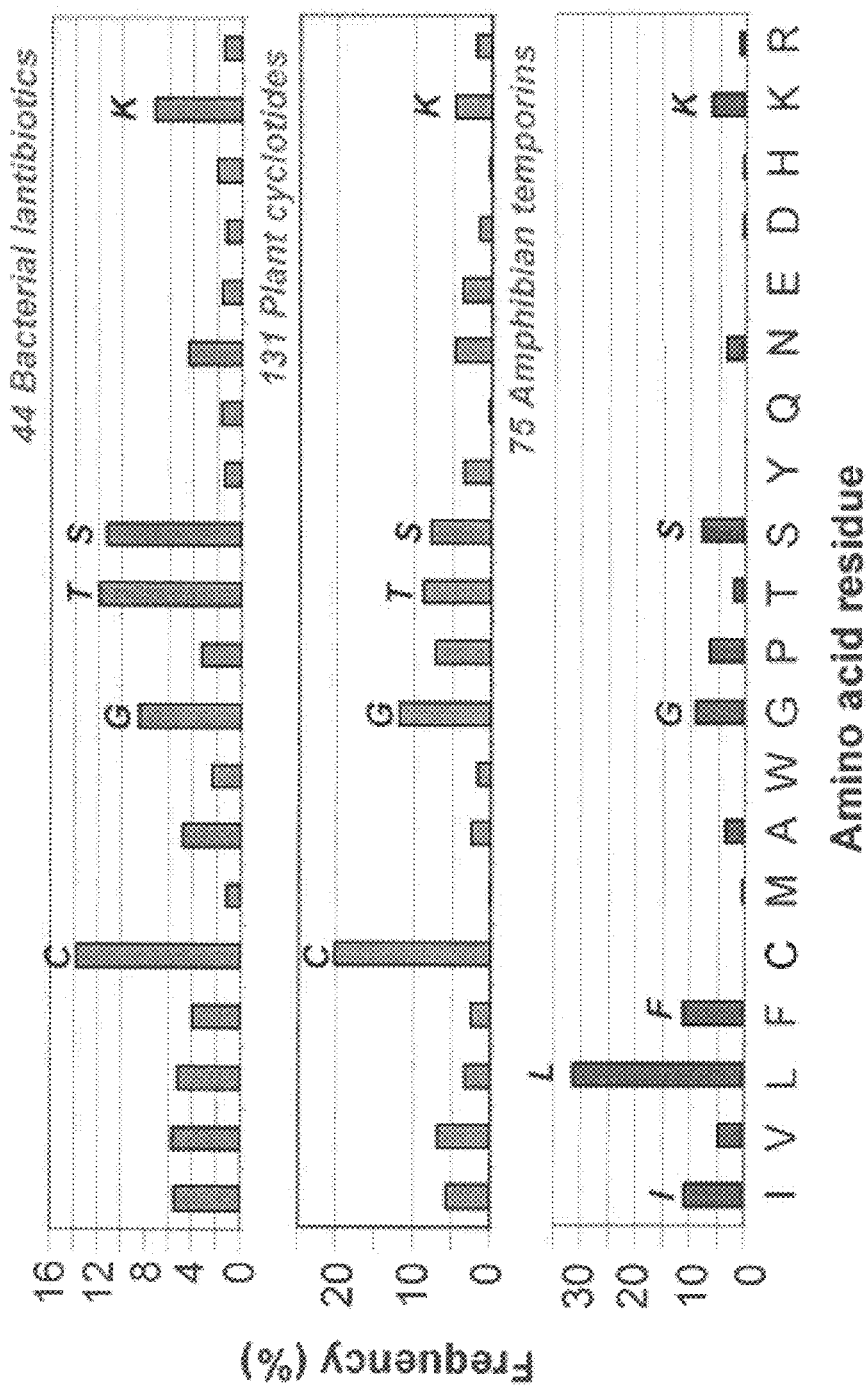

FIGS. 1A-1F show the database filtering technology (FIG. 1A) and the determination of peptide length (FIG. 1B), amino acids (FIG. 1C), charge (FIG. 1D), hydrophobic content (FIG. 1E), and structure type (FIG. 1F). Key parameters required for peptide design were obtained stepwise as depicted in FIG. 1A. The final peptide designed in this manner was referred to as DFTamP1 (i.e. database filtering technology-designed antimicrobial peptide 1). FIG. 1G shows that residues G, K, and S are shared frequently occurring residues in natural AMPs. Plotted are sequence profiles for 44 lantibiotics from bacteria, 131 cyclotides from plants, and 75 temporins from amphibians. Although these peptides adopt different structural scaffolds and kill bacteria in different mechanisms, G, S, and K are abundant in these three peptide groups from different life kingdoms, indicative of their universal importance in natural AMPs.

Figure 2A:
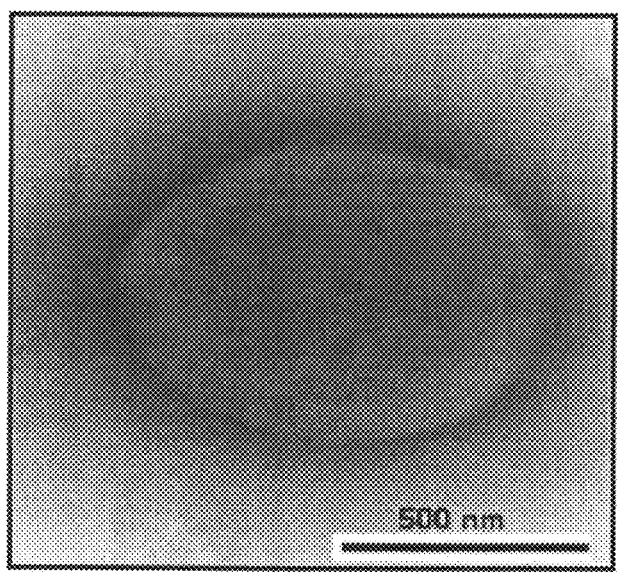
Figure 2B:
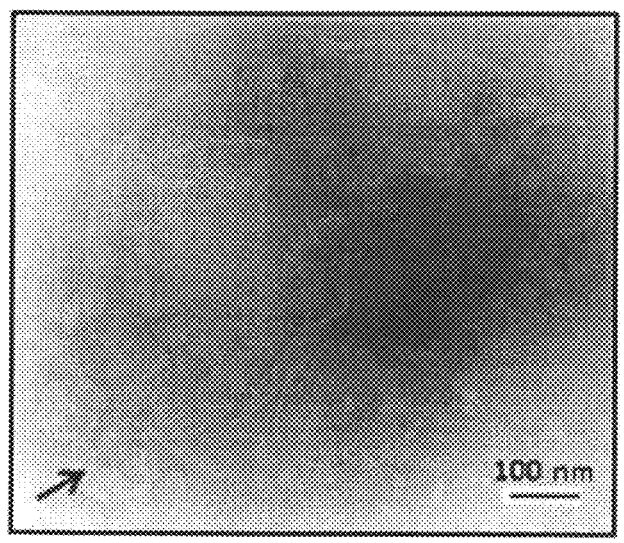
Figure 2C:
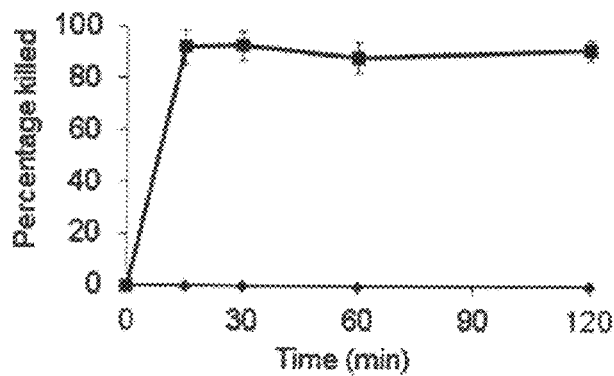
Figure 2D:
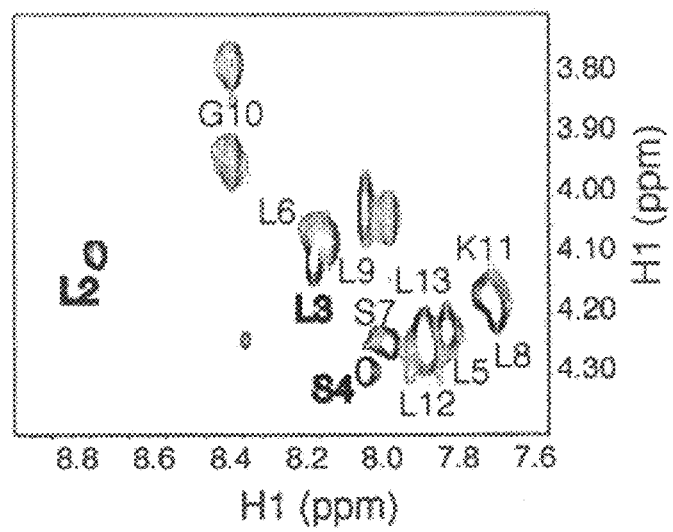
Figure 2E:
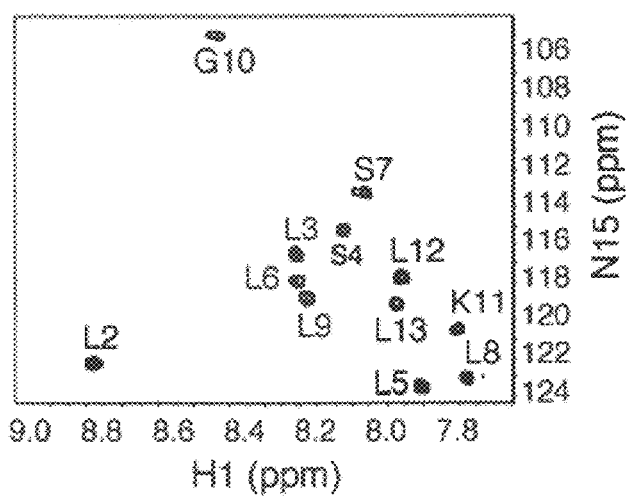
Figure 2F:
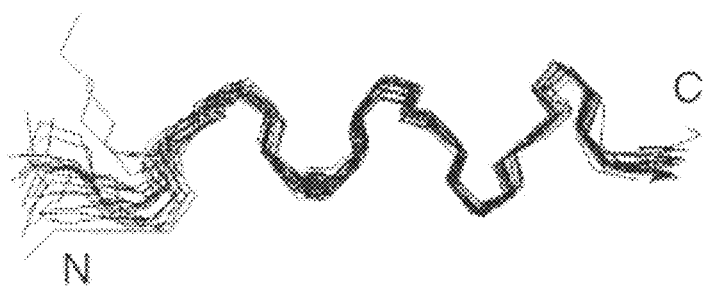
Figure 2G:
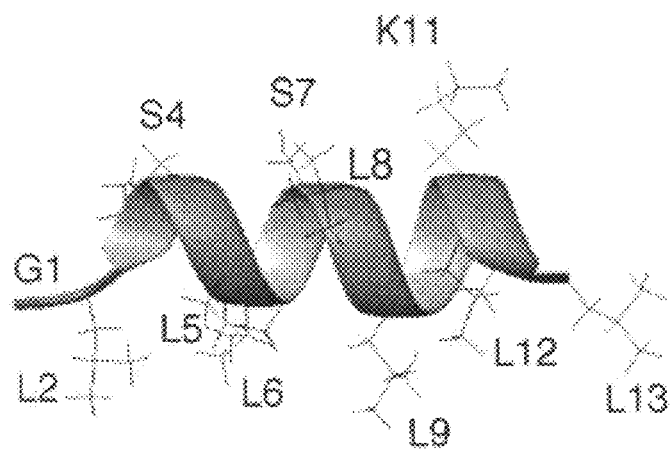
Figure 2H:
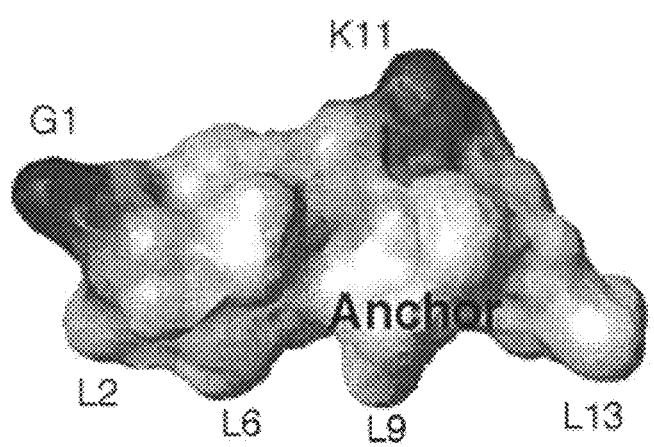
Figure 2I:
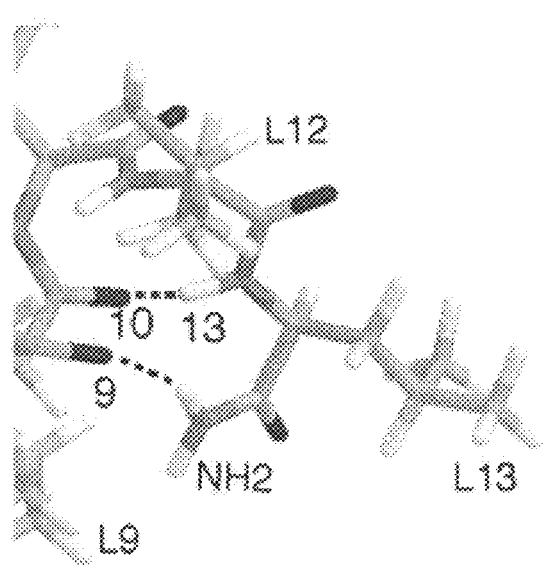
Figure 2J:
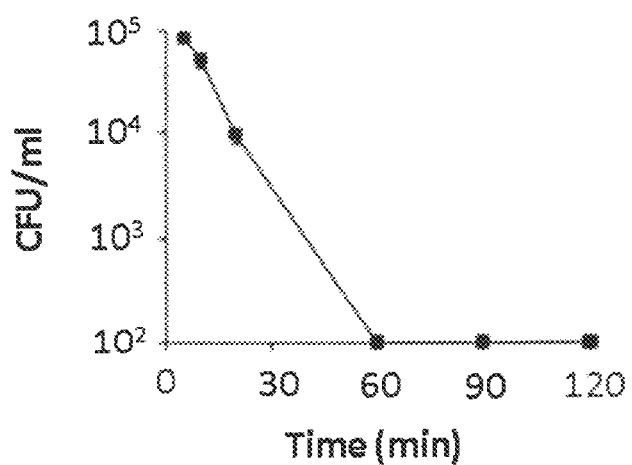

FIGS. 2A-2J show the structure and activity of DFTamP1. Shown are transmission electron microscopy images of MRSA USA300 before (FIG. 2A) and after peptide treatment (FIG. 2B), rapid killing of the $10^8$ colony-forming units of *S. aureus* USA300 by 2×MIC followed by flow cytometry (FIG. 2C), and NMR studies (FIGS. 2D and 2E) that enabled one to view the active conformation of the peptide (FIGS. 2F-2I). DFTamP1 has the highest content of leucines (61.5%) compared to natural temporins. Despite this difficulty, the cross peaks of these leucines are resolved in the natural abundance 2D $^1$H and $^{15}$N correlated NMR spectrum of DFTamP1 in complex with 40-fold deuterated sodium dodecyl sulfate at 25° C. and pH 5.4 (FIG. 2E). Displayed structural views of membrane-bound DFTamP1 are superimposed backbone structures (FIG. 2F), a ribbon diagram indicating a clear segregation of hydrophilic (residues S4, S7, and K11) and hydrophobic leucine side chains (FIG. 2G), potential surface (FIG. 2H), and local structure at the C-terminus indicating hydrogen bonding between the C-terminal amide $NH_2$ and the carbonyl atom of residue L9 of the peptide (FIG. 2I). FIG. 2J shows that the rapid killing of *S. aureus* USA300 by DFTamP1 is also supported by traditional killing kinetics. The experiments were set up in the same manner as the antibacterial assays above with the following additions. Bacteria ($10^5$ colony forming units of *S. aureus* USA300) were treated at a peptide level of 2×MIC). Aliquots were taken at 15, 30, 50, 90, and 120 minutes, plated after 100-fold dilution, and the colonies were counted after overnight incubation at 37° C.

Figure 3A:
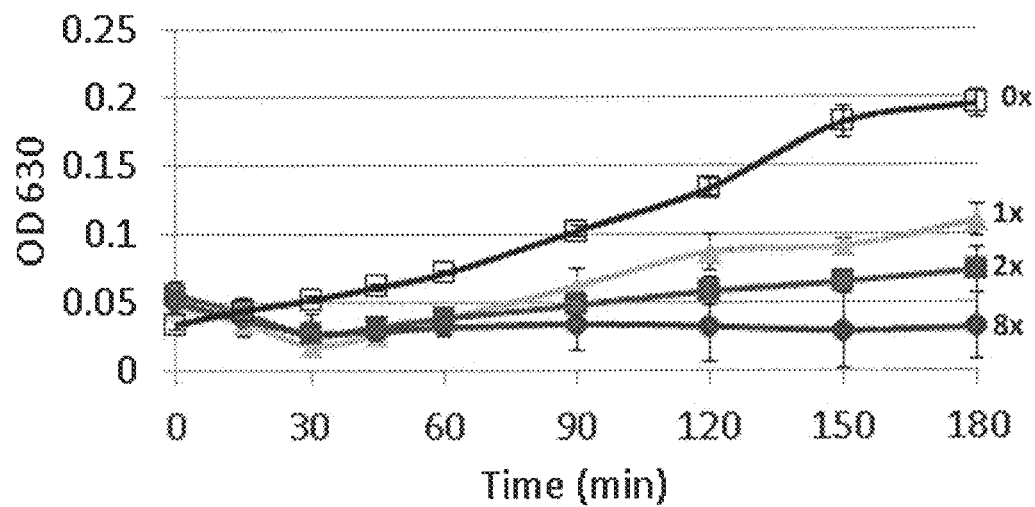
Figure 3B:
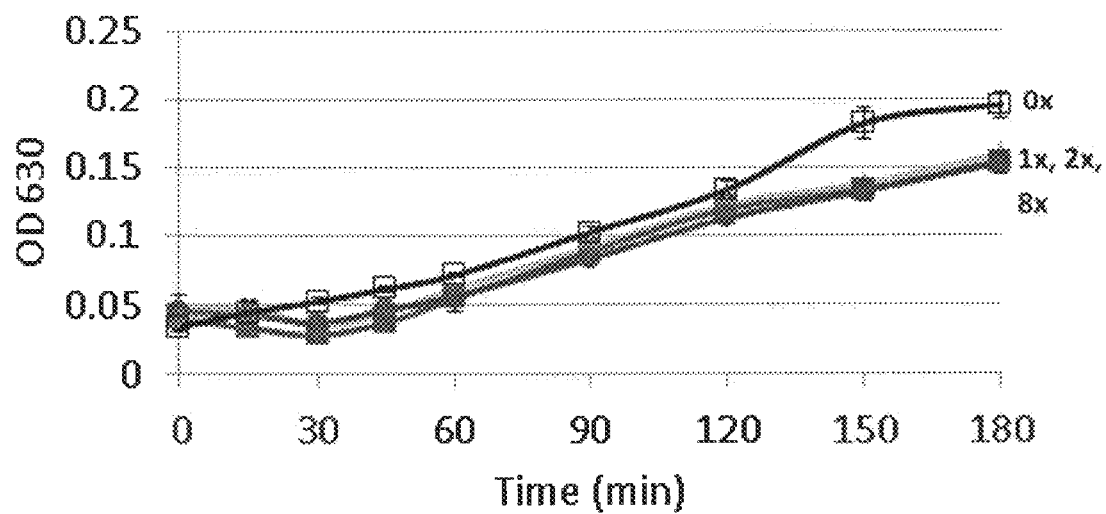

FIGS. 3A and 3B show the real time killing of *S. aureus* USA300 by DFTamP1 (FIG. 3A) and its mutant DFTamP1-pv (FIG. 3B). In the plots, bacterial growth or killing curves treated with 0, 1, 2, or 8×MICs of DFTamP1 are shown. For clarity, the curve at 4×MIC was not displayed since it is similar to that of 8×MIC. The microplate was incubated in a shaker at 100 rpm and 37° C. This figure indicates that the designed peptide DFTamP1 is able to lyse and inhibit MRSA USA300 at 8×MICs, whereas DFTamP1-pv was unable to even at four-fold the corresponding concentrations of DFTamP1.

Figure 4:
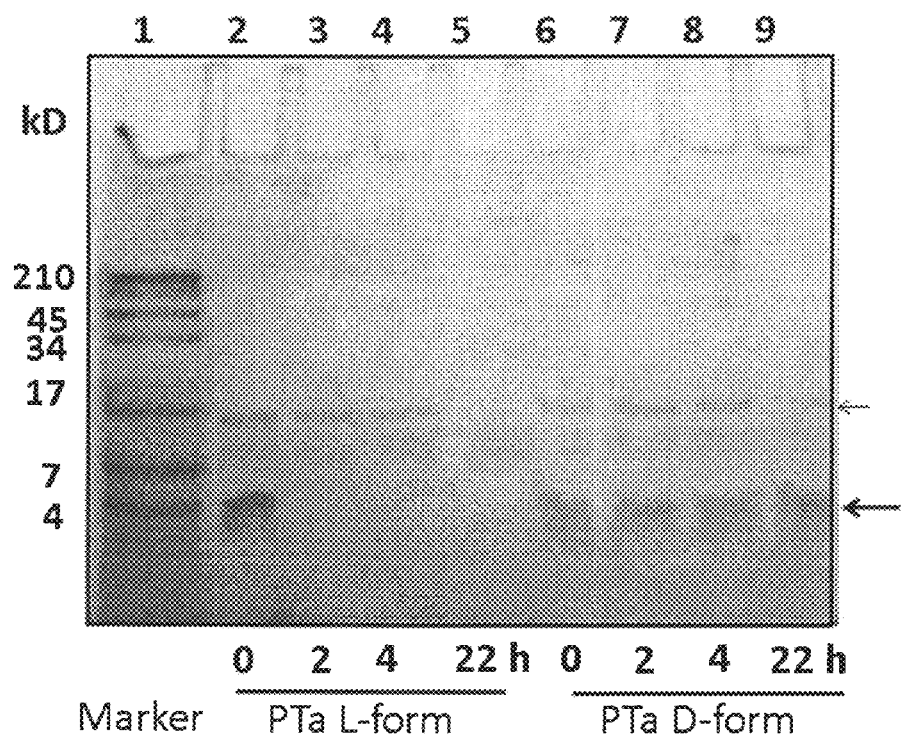

FIG. 4 shows a stability comparison of the L- and D-forms of temporin-PTa in the presence of chymotrypsin. A solution (100 µl) of the peptide and 12.5 µM chymotrypsin (peptide/protein molar ratio, 40:1) in 10 mM PBS buffer (pH 8) was incubated at 37° C. Aliquots (10 µl) of the reaction solutions were taken at 0, 2, 4, and 22 hours and immediately mixed with 20 µl of 2×SDS loading buffer to stop the reaction. For the gel analysis, 10 µl of each sample was loaded to the well of a 5% stacking/18% resolving tricine gel. The samples in the lanes are: 1, protein marker; 2, temporin-PTa L-form at 0 hour; 3, 2 hours; 4, 4 hours; 5, 22 hours; 6, temporin-PTa D-form at 0 hour; 7, 2 hours; 8, 4 hours; 9, 22 hours. In the gel, the bands for the peptide and chymotrypsin were indicated with large and small arrows, respectively. Note that the peptide bands were not detected in lanes 3-5 due to protease cleavage but remained essentially constant in lanes 7-9. This figure indicates that in the presence of chymotrypsin, the L-form of temporin-PTa was degraded within 2 hours (lanes 3-5), while the D-form was stable for at least 22 hours (lanes 7-9).

FIG. 5A-5D show the impact of DASamP1 on *S. aureus* biofilms in vivo. Mice received DASamP1 injections at 0, 24, and 48 hours following *S. aureus* infection and were sacrificed at days 3 (FIGS. 5A, 5B) and 14 (FIGS. 5C, 5D) following infection, whereupon catheters (FIGS. 5A, 5C) and surrounding host tissue (FIGS. 5B, 5D) were recovered to quantitate bacterial burdens. Results are expressed as the number of cfu per ml for catheters or cfu per mg tissue to correct for differences in tissue sampling size. Significant differences inn bacterial burdens between PBS and peptide-treated mice are denoted by asterisk (*, p<0.05) with results presented from individual animals with bars representing the mean of each group.

Figure 6:
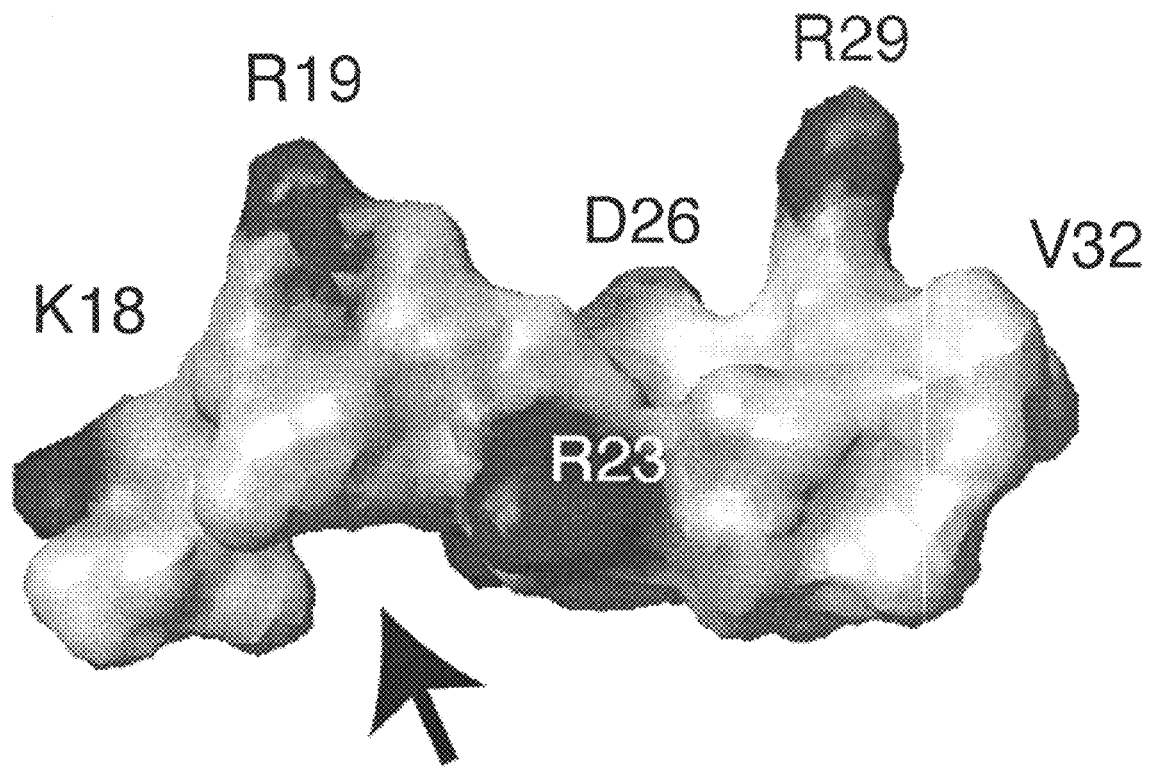

FIG. 6 shows the hydrophobic defect (pointed by an arrow) in the potential surface of GF-17d3 determined by NMR spectroscopy (Li et al. (2006) J. Am. Chem. Soc. 128:5776-5785). This structure forms the basis for designing various antimicrobial peptides by filling this structural defect with a variety of hydrophobic groups.

Figure 7:
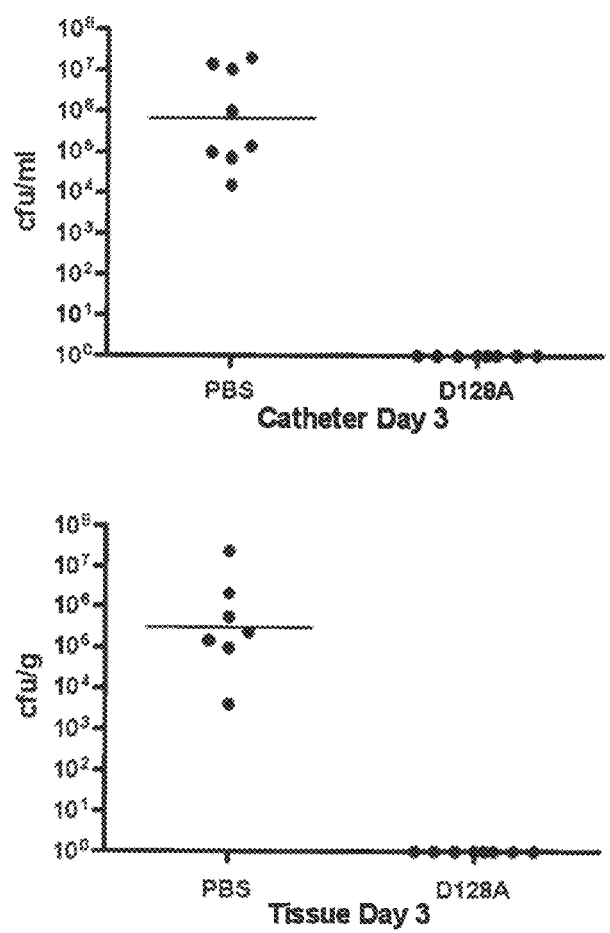
Figure 8F:
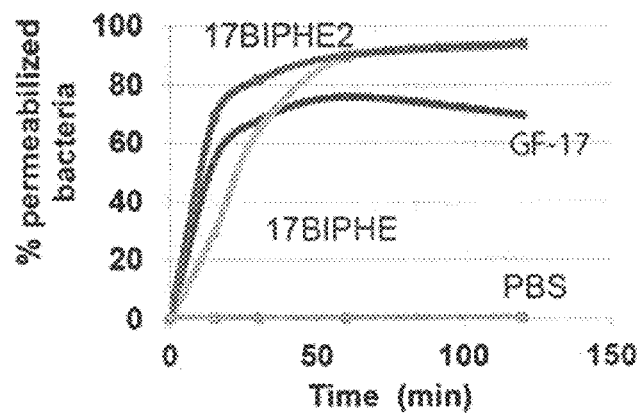
Figure 8G:
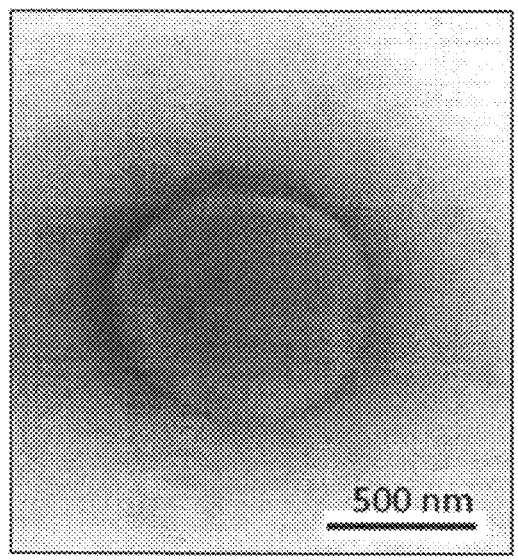

FIG. 7 shows that the LL-37 peptide derivative D128A demonstrates long-term efficacy at reducing *S. aureus* biofilm infections in vivo. C57BL/6 mice received 4 injections (200 μg each) of D128A or PBS vehicle at 12, 24, and 48 hours following *S. aureus* infection, whereupon bacterial titers associated with infected catheters and surrounding tissues were quantitated at day 3 or 14 post-infection. Each symbol represents data from an individual animal. Significant differences are denoted by asterisks (*, p<0.001).

FIGS. 8A-8I show the structure-based design of potent peptides to combat ESKAPE pathogens. Shown are NMR structures of human LL-37 (FIG. 8A); its peptides GF-17 (FIG. 8B) and GF-17d3 (FIGS. 8C and 8D) bound to membrane-mimetic micelles; peptide degradation kinetics (FIG. 8E); flow cytometry of *S. aureus* USA300 after treatments with 40 μM GF-17, 17BIPHE, or 17BIPHE2 peptides (FIG. 8F); transmission electron microscopy images of *S. aureus* USA300 before (FIG. 8G) and after (FIG. 8H) peptide treatment; and DNA retardation (FIG. 8) by the peptides in Table 10. Each peptide was evaluated by a 1% agarose gel (casted with 1 μg/mL ethidium bromide) at two concentrations, first at 6 and then 12 μM (lane 1: 75 ng pUC19 DNA plasmid itself; lanes 2 and 3: 17F2; lanes 4 and 5: 17mF-F; lanes 6 and 7: 17F-Naph; lanes 8 and 9: 17mF-Naph; lanes 10 and 11: 17Naph-mF; lanes 12 and 13: 17BIPHE; lanes 14 and 15: 17BIPHE2). Structural images were generated using MOLMOL (Koradi et al. (1996) J. Mol. Graphics 14:51-55).

Figure 9A:
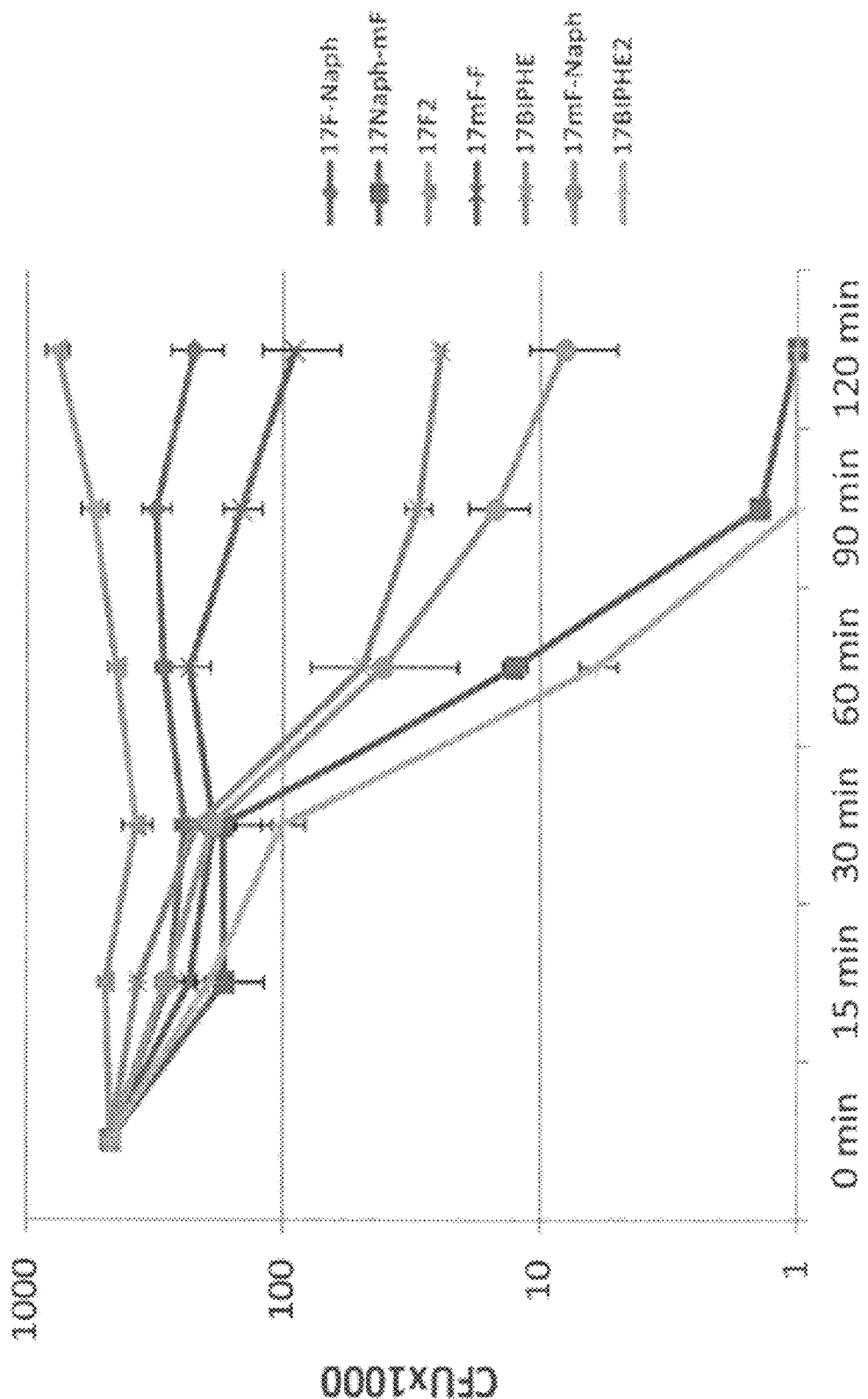
Figure 9B:
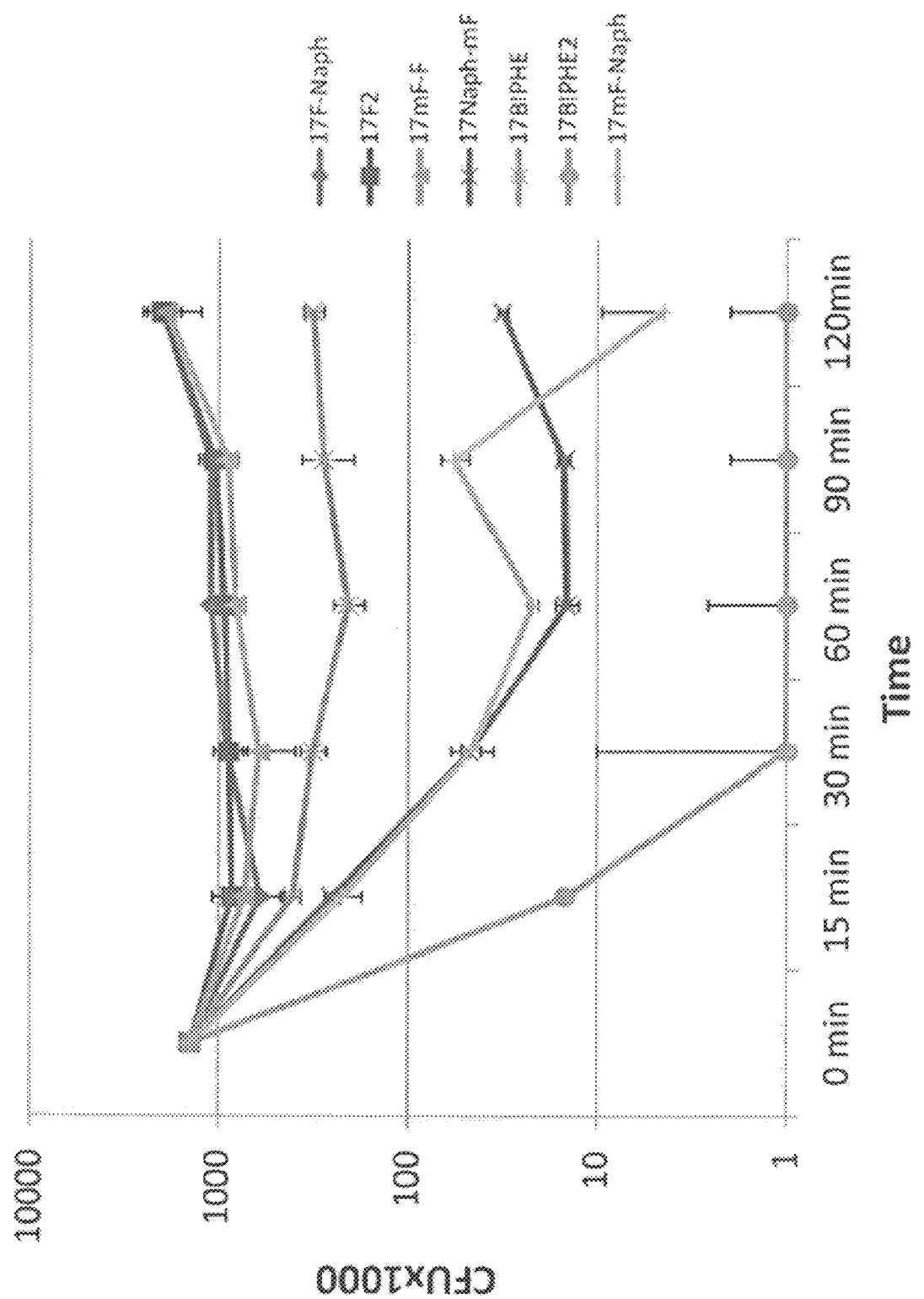

FIGS. 9A and 9B provide the killing kinetics of a family of antimicrobial compounds designed based on the 3D structure of a human cathelicidin LL-37 derived peptide. *S. aureus* USA300 LAC (FIG. 9A) or *P. aeruginosa* PAO1 (FIG. 9B) (~$10^6$ colony forming units) were treated at the same concentration for all the seven peptides. Aliquots were taken at 15, 30, 60, 90, and 120 minutes, plated on LB agar plates after 100-fold dilution, and the colonies (CFU) were counted after overnight incubation at 37° C.

Figure 10:
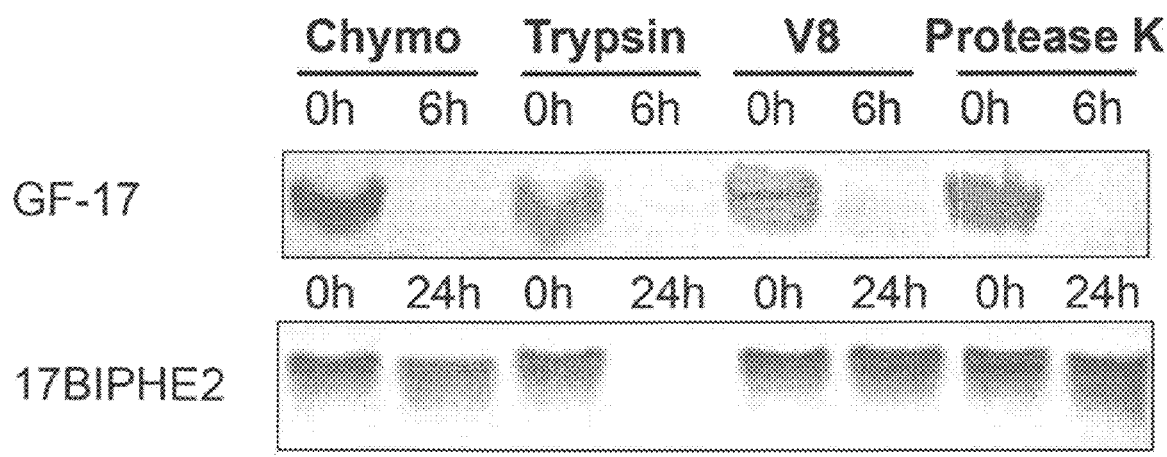

FIG. 10 provides a stability comparison of synthetic 17BIPHE2 with GF-17 in the presence of bovine chymotrypsin, porcine trypsin, *S. aureus* protease V8, and fungal protease K. Two samples were analyzed in this gel for each protease: 0 and 6 hours for GF-17 and 0 and 24 hours for 17BIPHE2.

Figure 11:
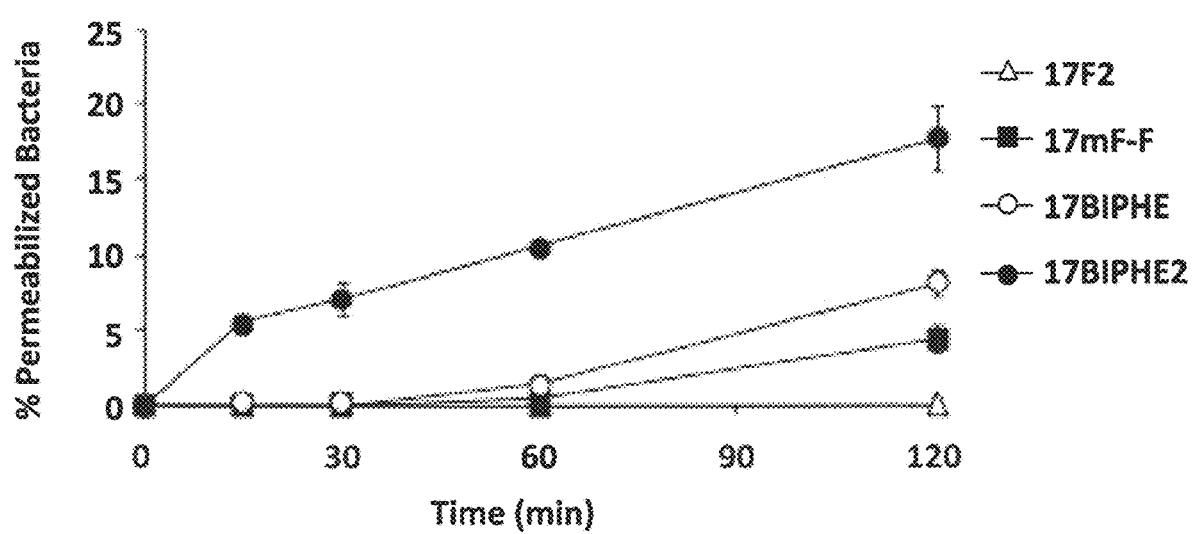

FIG. 11 shows the membrane permeation of *S. aureus* USA300 followed by flow cytometry with four tested peptides at 20 μM (17BIPHE2, 17BIPHE, 17mF-F, and 17F2). For clarity, the membrane permeation curve in PBS buffer (i.e., without peptide treatment) was not displayed since it overlapped with that of 17F2.

Figure 12:
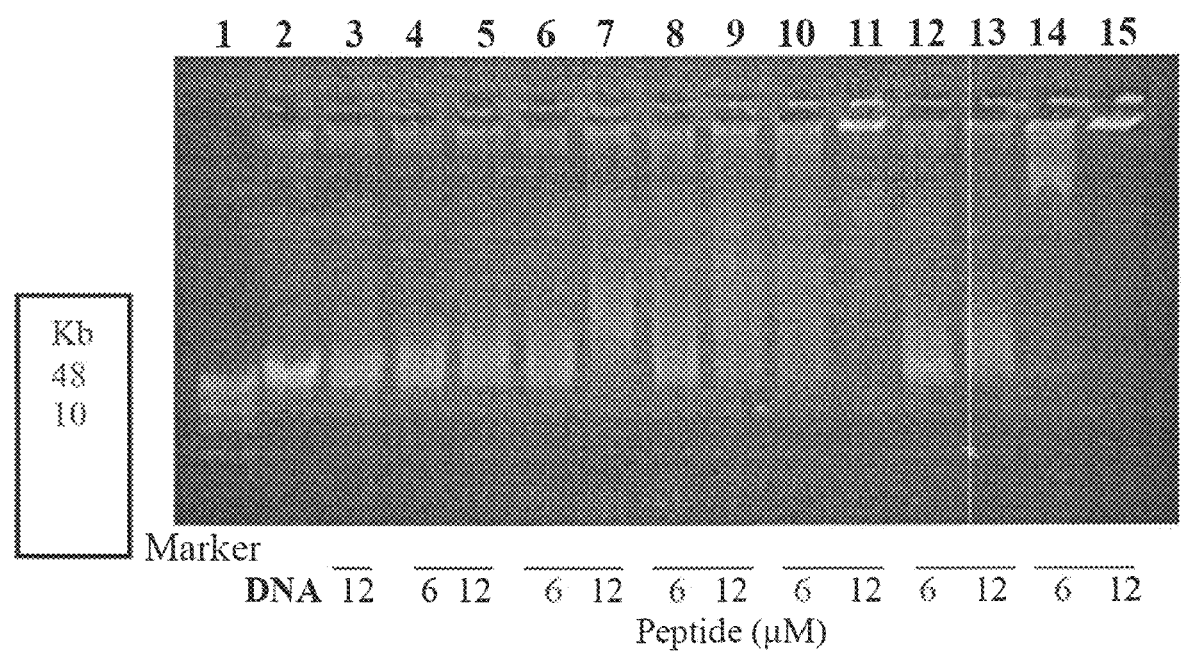

FIG. 12 provides an image of DNA retardation by a family of human cathelicidin LL-37-derived peptides using *P. aeruginosa* PAO1 DNA. 0.5% agarose gel was casted with ethidium bromide (0.3 μg/mL). The DNA was extracted without the use of cetyltrimethyl ammonium bromide (CTAB). Lane 1: DNA ladder; lane 2: 100 ng *P. aeruginosa* DNA; lane 3: 100 ng DNA and 12 μM 17F2; lane 4: 100 ng DNA and 6 μM 17mF-F; lane 5: 100 ng DNA and 12 μM 17mF-F; lane 6: 100 ng DNA and 6 μM 17F-Naph; lane 7: 100 ng DNA and 12 μM 17F-Naph; lane 8, 100 ng DNA and 6 μM 17mF-Naph; lane 9: 100 ng DNA and 12 μM 17mF-Naph; lane 10: 100 ng DNA and 6 μM 17Naph-mF; lane 11: 100 ng DNA and 12 μM 17Naph-mF; lane 12: 100 ng DNA and 6 μM 17BIPHE; lane 13: 100 ng DNA and 12 μM 17BIPHE; lane 14: 100 ng DNA and 6 μM 17BIPHE2; and lane 15: 100 ng DNA and 12 μM 17BIPHE2.

Figure 13A:
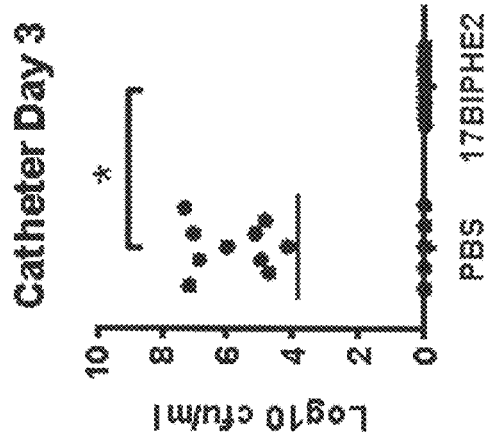
Figure 13B:
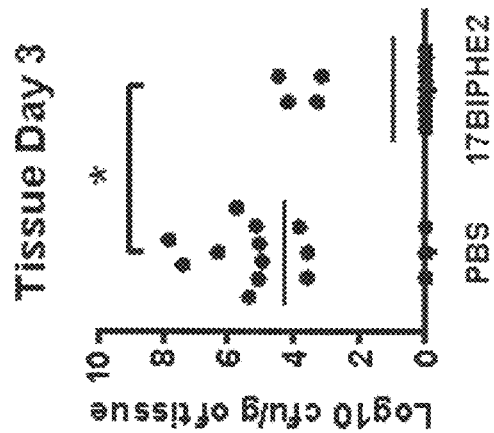
Figure 13C:
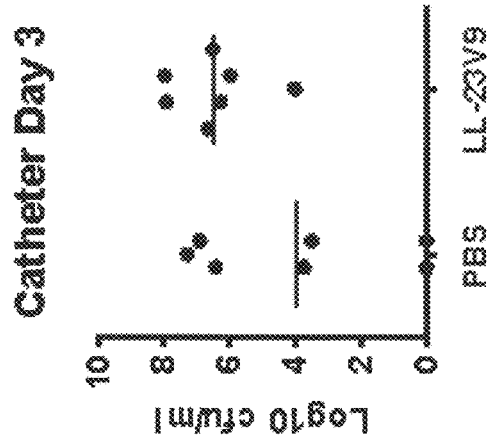
Figure 13D:
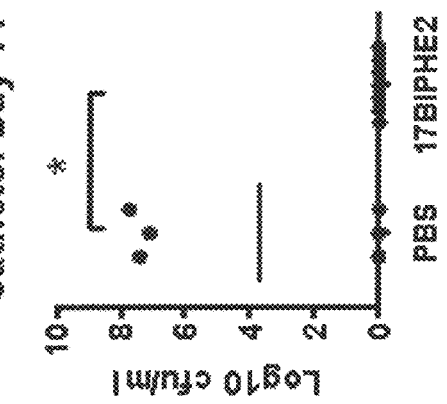
Figure 13E:
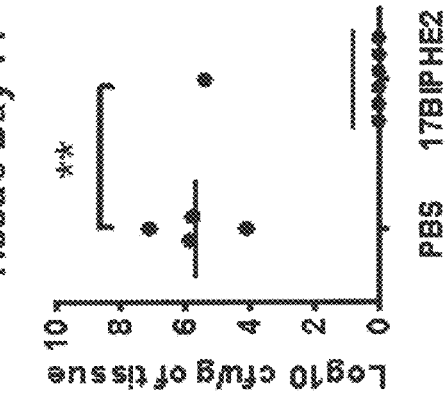
Figure 13F:
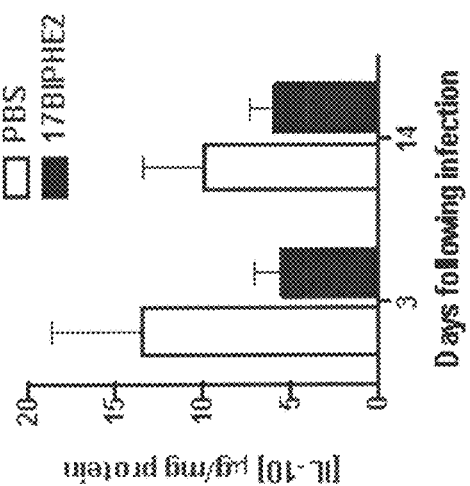
Figure 13I:
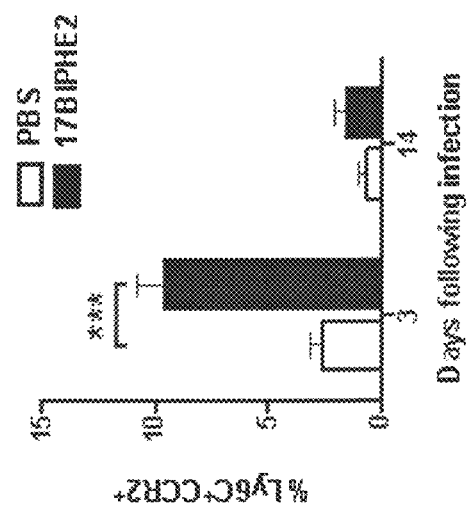

FIGS. 13A-13I show that prophylactic 17BIPHE2 treatment reduced bacterial burdens in *S. aureus* catheter-associated biofilms in vivo (FIGS. 13A-13E), down-regulated IL-10 (FIG. 13F), up-regulated CCL2 (FIG. 13G) and CXCL10 (FIG. 13H), and recruited monocytes (FIG. 13I). Mice received 200 μg injections of 17BIPHE2 (FIGS. 13A, 13B, 13D, and 13E) and LL-23V9 (FIG. 13C) directly into the catheter at the time of infection (time 0) followed by 200 μg peptide injected subcutaneously at four different sites around the catheter, 24 and 48 hours following infection. Animals were sacrificed at days 3 (FIGS. 13A, 13B, and 13C) and 14 (FIGS. 13D and 13E) following *S. aureus* exposure, whereupon catheters (FIGS. 13A, 13C, and 13D) and surrounding host tissues (FIGS. 13B and 13E) were recovered to quantitate bacterial burdens. Results are expressed as the number of CFU/mL for catheters or CFU/mg tissue, to correct for differences in tissue sampling size. Significant differences in bacterial burdens between PBS and peptide-treated mice are denoted by asterisks (*, p<0.05; **, p<0.01) with results presented from individual animals and bars representing the mean of each group (13A and 13B: n=16/group; 13C, 13D, and 13E: n=8/group).

DETAILED DESCRIPTION OF THE INVENTION

Natural antimicrobial peptides are promising candidates to be developed into a new generation of antimicrobials due to their potency for millions of years. To effectively exploit these molecules, the antimicrobial peptide database (aps.unmc.edu/AP) has been constructed. A unique approach dubbed database filtering technology (DFT) is provided herein that enables one to design ab initio potent anti-MRSA peptides systematically. DFTamP1, the first antimicrobial peptide designed using DFT, has numerous desired features: short (cost effective to synthesize), stable (the D-form is resistant to proteases), and effective in vivo. Additionally, further compounds were obtained by combining the findings from previous database screens and the current ab initio design. Therefore, the instant invention covers both novel methods for peptide design and novel anti-MRSA compounds.

I. DEFINITIONS

The term "isolated" is not meant to exclude artificial or synthetic mixtures with other compounds or materials, or the presence of impurities that do not interfere with the fundamental activity, and that may be present, for example, due to incomplete purification, or the addition of stabilizers.

The term "substantially pure" refers to a preparation comprising at least 50-60% by weight of a given material (e.g., nucleic acid, oligonucleotide, protein, etc.). More preferably, the preparation comprises at least 75% by weight, and most preferably 90-95% or more by weight of the given compound. Purity is measured by methods appropriate for the given compound (e.g. chromatographic methods, agarose or polyacrylamide gel electrophoresis, HPLC analysis, and the like).

"Pharmaceutically acceptable" indicates approval by a regulatory agency of the Federal or a state government or listed in the U.S. Pharmacopeia or other generally recognized pharmacopeia for use in animals, and more particularly in humans.

A "carrier" refers to, for example, a diluent, adjuvant, preservative (e.g., Thimersol, benzyl alcohol), anti-oxidant (e.g., ascorbic acid, sodium metabisulfite), solubilizer (e.g., Tween™ 80, Polysorbate 80), emulsifier, buffer (e.g., Tris HCl, acetate, phosphate), antimicrobial, bulking substance (e.g., lactose, mannitol), excipient, auxiliary agent or vehicle with which an active agent of the present invention is administered. Pharmaceutically acceptable carriers can be sterile liquids, such as water and oils, including those of petroleum, animal, vegetable or synthetic origin. Water or aqueous saline solutions and aqueous dextrose and glycerol solutions are preferably employed as carriers, particularly for injectable solutions. Suitable pharmaceutical carriers are described in "Remington's Pharmaceutical Sciences" by E. W. Martin (Mack Publishing Co., Easton, Pa.); Gennaro, A. R., Remington: The Science and Practice of Pharmacy, 20th Edition, (Lippincott, Williams and Wilkins), 2000; Liberman, et al., Eds., Pharmaceutical Dosage Forms, Marcel Decker, New York, N.Y., 1980; and Kibbe, et al., Eds., Handbook of Pharmaceutical Excipients ($3^{rd}$ Ed.), American Pharmaceutical Association, Washington, 1999.

A "therapeutically effective amount" of a compound or a pharmaceutical composition refers to an amount effective to prevent, inhibit, treat, and/or lessen the symptoms of a particular disorder or disease. The treatment of a microbial infection (e.g., *S. aureus* infection) herein may refer to an amount sufficient to inhibit microbial growth or kill the microbe and/or curing, relieving, and/or preventing the microbial infection, the symptom of it, or the predisposition towards it.

As used herein, the term "antibiotic" refers to antimicrobial agents for use in mammalian, particularly human, therapy. Antibiotics include, without limitation, beta-lactams (e.g., penicillin, ampicillin, oxacillin, cloxacillin, methicillin, and cephalosporin), carbacephems, cephamycins, carbapenems, monobactams, aminoglycosides (e.g., gentamycin, tobramycin), glycopeptides (e.g., vancomycin), quinolones (e.g., ciprofloxacin), moenomycin, tetracyclines, macrolides (e.g., erythromycin), fluoroquinolones, oxazolidinones (e.g., linezolid), lipopetides (e.g., daptomycin), aminocoumarin (e.g., novobiocin), co-trimoxazole (e.g., trimethoprim and sulfamethoxazole), lincosamides (e.g., clindamycin and lincomycin), polypeptides (e.g., colistin), and derivatives thereof.

II. PEPTIDES

The anti-microbial peptides of the present invention may be prepared in a variety of ways, according to known methods. The anti-microbial peptides of the instant invention may also be chemically synthesized. For example, the peptides may be synthesized using a liquid-phase method or solid-phase method. The chemically synthesized peptides may then be purified (e.g., by HPLC).

The anti-microbial peptides may also be purified from appropriate sources (e.g., bacterial or animal cultured cells or tissues, optionally transformed) by immunoaffinity purification. The availability of nucleic acid molecules encoding the anti-microbial peptides enables production of the protein using in vitro expression methods and cell-free expression systems known in the art.

Larger quantities of anti-microbial peptides may be produced by expression in a suitable prokaryotic or eukaryotic system. For example, part or all of a DNA molecule encoding for an anti-microbial peptide may be inserted into a plasmid vector adapted for expression in a bacterial cell, such as *E. coli*. Such vectors comprise the regulatory elements necessary for expression of the DNA in the host cell positioned in such a manner as to permit expression of the DNA in the host cell. Such regulatory elements required for expression include promoter sequences, transcription initiation sequences and, optionally, enhancer sequences.

Anti-microbial peptides produced by gene expression in a recombinant prokaryotic or eukaryotic system may be purified according to methods known in the art. A commercially available expression/secretion system can be used, whereby the recombinant protein is expressed and thereafter secreted from the host cell, and readily purified from the surrounding medium. If expression/secretion vectors are not used, an alternative approach involves purifying the recombinant protein by affinity separation, such as by immunological interaction with antibodies that bind specifically to the recombinant protein or nickel columns for isolation of recombinant proteins tagged with 6-8 histidine residues at their N-terminus or C-terminus. Alternative tags may comprise the FLAG epitope or the hemaglutinin epitope. Such methods are commonly used by skilled practitioners.

Anti-microbial peptides of the invention, prepared by the aforementioned methods, may be analyzed and verified according to standard procedures. For example, such protein may be subjected to amino acid sequence analysis, according to known methods.

Anti-microbial peptides are provided in the examples hereinbelow. Indeed, the instant invention encompasses any anti-microbial peptide described herein and their derivatives/variants, e.g., those derivatives/variants generated by sequence truncation, mutation, reversal, or shuffling. For example, the anti-microbial peptide of the instant invention may comprise any one of SEQ ID NOs: 1-63, particularly SEQ ID NOs: 1-9 and 22-63. As stated hereinbelow, the peptides may or may not comprise modifications (e.g., amidation or D-amino acids) and the provided SEQ ID NOs may encompass the base sequence with or without the modifications. In a particular embodiment, the anti-microbial peptide of the instant invention comprises SEQ ID NO: 1 (DFTamP1), SEQ ID NO: 2 (DFTamP1-p), SEQ ID NO: 5 (temporin-PTa), SEQ ID NO: 6 (temporin-PTa, D-form), SEQ ID NO: 7 (temporin-PTa6L), SEQ ID NO: 8 (temporin-PTa8L), SEQ ID NO: 9 (DASamP1), SEQ ID NO: 34 (piscidin 1), SEQ ID NO: 37 (lycotoxin I), SEQ ID NO: 40 (maculatin 1.3), SEQ ID NO: 43 (ascaphin-8), SEQ ID NO: 47 (DASamP2), SEQ ID NO: 48 (DASamP5), SEQ ID NO: 50 (DASamP5), SEQ ID NO: 51 (DASamP6), SEQ ID NO: 52 (DASamP7), SEQ ID NO: 53 (DASamP8), SEQ ID NO: 59 (A128A), SEQ ID NO: 60 (B128A), SEQ ID NO: 61 (C128A), or SEQ ID NO: 62 (D128A). In a particular embodiment, the anti-microbial peptide of the instant invention (particularly in methods of inhibiting a microbial infection) comprises SEQ ID NO: 5 (temporin-PTa), SEQ ID NO: 34 (piscidin 1), SEQ ID NO: 37 (lycotoxin I), SEQ ID NO: 40 (maculatin 1.3), or SEQ ID NO: 43 (ascaphin-8), particularly SEQ ID NO: 5 (temporin-PTa) or SEQ ID NO: 40 (maculatin 1.3). In another embodiment, the anti-microbial peptide of the instant invention comprises SEQ ID NO: 1 (DFTamP1), SEQ ID NO: 6 (temporin-PTa, D-form), SEQ ID NO: 7 (temporin-PTa6L), SEQ ID NO: 8 (temporin-PTa8L), SEQ ID NO: 9 (DASamP1), SEQ ID NO: 47 (DASamP2), SEQ ID NO: 51 (DASamP6), SEQ ID NO: 52 (DASamP7), SEQ ID NO: 53 (DASamP8), or SEQ ID NO: 62 (D128A). In another embodiment, the anti-microbial peptide of the instant invention comprises SEQ ID NO: 1, 2, 6, 7, 8, 9, 48, 50, 51, 52, 53, 59, 60, 61, or 62. In another embodiment, the anti-microbial peptide of the instant invention comprises SEQ ID NO: 1, 2, 6, 7, 8, 59, 60, 61, or 62. In a particular embodiment, the anti-microbial peptide of the instant invention comprises SEQ ID NO: 58 or 63. In a particular embodiment, the anti-microbial peptide of the instant invention comprises SEQ ID NO: 1 (DFTamP1).

In a particular embodiment of the instant invention, the peptide comprises the sequence: $X_1X_2X_3X_4LLX_5LLX_6X_7LL$ (SEQ ID NO: 63), wherein $X_1$-$X_7$ are any amino acid or derivative thereof. In a particular embodiment, $X_1$, $X_2$, $X_3$, and $X_4$ comprise two consecutive hydrophobic amino acids (e.g., Ile, Leu, Val, Tip, or Phe) and two hydrophilic amino acids (e.g., Asn, Ser, Gln, Thr, Gly, Pro, His, Lys, or Arg) and $X_5$, $X_6$, and $X_7$ are each a hydrophilic amino acid.

In one embodiment, $X_4$ is Ser, $X_7$ is Lys, $X_1$, $X_2$, and $X_3$ comprise two consecutive hydrophobic amino acids, particularly Leu or Phe. In a particular embodiment, the non-hydrophobic amino acid of $X_1$, $X_2$, and $X_3$ is Gly. In a particular embodiment, $X_5$ is a polar or positively charged amino acid, particularly Ser or Lys. In a particular embodiment, $X_6$ is Pro or Gly.

In another embodiment, $X_1$ and $X_2$ are Leu and $X_3$-$X_7$ are hydrophilic amino acids. In a particular embodiment, $X_3$ is Gly. In a particular embodiment, $X_4$ is a polar or positively charged amino acid, particularly Ser or Lys. In a particular embodiment, $X_5$ is a polar or positively charged amino acid, particularly Ser or Lys. In a particular embodiment, $X_6$ is Pro or Gly. In a particular embodiment, $X_7$ is a polar or positively charged amino acid, particularly Ser or Lys.

In yet another embodiment, $X_1$ and $X_2$ are Phe and $X_3$-$X_7$ are hydrophilic amino acids. In a particular embodiment, $X_3$ is Gly. In a particular embodiment, $X_4$ is a polar or positively charged amino acid, particularly Ser or Lys. In a particular embodiment, $X_5$ is a polar or positively charged amino acid, particularly Ser or Lys. In a particular embodiment, $X_6$ is Pro or Gly. In a particular embodiment, $X_7$ is a polar or positively charged amino acid, particularly Ser or Lys.

In yet another embodiment, at least one of the Leu residues of the peptide of SEQ ID NO: 63 are replaced with another hydrophobic amino acid (e.g., Ile, Leu, Val, Trp, or Phe).

In a particular embodiment of the instant invention, the peptide comprises the sequence: $GX_1KRLVQRLKDX_2LRNLV$ (SEQ ID NO: 58), wherein $X_1$ and $X_2$ are any amino acid or derivative (e.g., analog), particularly any hydrophobic amino acids (e.g., Ile, Leu, Val, Trp, or Phe). In a particular embodiment, the Leu at positions 5, 9, and 13 are D-amino acids. In a particular embodiment, either one or both of the Leu at positions 5 and 9 are substituted with isoleucine (e.g., D-Ile). $X_1$ and $X_2$ may be a hydrophobic amino acid (inclusive of derivatives and analogs) that is larger than phenylalanine and/or more hydrophobic than phenylalanine. In a particular embodiment, $X_1$ and $X_2$ are independently selected from the group consisting of phenylalanine, trifluoromethylphenylalanine, napthylalanine, biphenylalanine, methylphenylalanine, ethylphenylalanine, benzoylphenylalanine, t-butylphenylalanine, sulfomethylphenylalanine, hydroxyphenylalanine, methoxyphenylalanine, and hydroxymethylphenylalanine. The recited substituents may be located at any position of the aromatic ring of phenylalanine, particularly at position 4. In a particular embodiment, $X_1$ and $X_2$ are independently selected from the group consisting of phenylalanine, trifluoromethylphenylalanine (e.g., 4-trifluoromethylphenylalanine), napthylalanine (e.g., 2-napthylalanine), and biphenylalanine (e.g., 4-phenyl-phenylalanine). In a particular embodiment, neither $X_1$ nor $X_2$ are phenylalanine. In a particular embodiment, the peptide comprises SEQ ID NO: 59, 60, 61, 62, 68, 69, or 70.

The amino acid sequence of the anti-microbial peptide of the instant invention may have at least 75%, 80%, 85%, 90%, 95%, 97%, 99%, or 100% homology with the above sequences, particularly at least 90% homology (e.g., the sequence may contain additions, deletions, and/or substitutions). In a particular embodiment, the anti-microbial peptide of the instant invention may extend beyond the above sequences at the amino and/or carboxy terminus by 1, 2, 3, 4, 5, 6, 7, 8, 9, or 10 amino acids, particularly by 1, 2, 3, 4, or 5 amino acids, particularly by 1, 2, or 3 amino acids. In yet another embodiment, the anti-microbial inhibitory peptides of the instant invention may also be in reverse orientation. In a particular embodiment, the peptides of the instant invention have fewer than about 50 amino acids, fewer than about 25 amino acids, fewer than about 20 amino acids, fewer than about 17 amino acids, or fewer than about 15 amino acids. In a particular embodiment, the peptides of the instant invention have more than about 5 amino acids, more than about 7 amino acids, or more than about 10 amino acids.

As stated hereinabove, the anti-microbial peptide of the instant invention may contain substitutions for the amino acids of the provided sequence. These substitutions may be similar to the amino acid (i.e., a conservative change) present in the provided sequence (e.g., an acidic amino acid in place of another acidic amino acid, a basic amino acid in place of a basic amino acid, a large hydrophobic amino acid in place of a large hydrophobic, etc.). The substitutions may also comprise amino acid analogs and mimetics. In a particular embodiment, the substitutions are predicted to promote helicity or helix formation.

The anti-microbial peptide of the instant invention may have capping, protecting and/or stabilizing moieties at the C-terminus and/or N-terminus. Such moieties are well known in the art and include, without limitation, amidation and acetylation. The peptide template may also be lipidated or glycosylated at any amino acid (i.e., a glycopeptide). In particular, these peptides may be PEGylated to improve druggability. The number of the PEG units ($NH_2(CH_2CH_2O)CH_2CH_2CO$) may vary, for example, from 1 to about 50.

The anti-microbial peptide of the instant invention may also comprise at least one D-amino acid instead of the native L-amino acid. The anti-microbial peptide may comprise only D-amino acids. In a particular embodiment, the anti-microbial peptides comprise D-amino acids which are spaced apart by about 1, 2, 3, and/or 4 (e.g., 3) consecutive L-amino acids.

The microbe-inhibitory peptides of the instant invention may contain at least one derivative of standard amino acids, such as, without limitation, fluorinated residues or nonstandard amino acids (e.g., beta-amino acids). In yet another embodiment, the peptide may also be circulated head to tail or locally involving a few residues.

The present invention also encompasses nucleic acids encoding the peptides and pharmaceutical compositions comprising at least one antimicrobial peptide of the instant invention and at least one pharmaceutically acceptable carrier (see below). The present invention also encompasses methods for preventing, inhibiting, and/or treating microbial infections (as explained hereinbelow). The pharmaceutical compositions of the instant invention can be administered to an animal, in particular a mammal, more particularly a human, in order to treat/inhibit/prevent a microbial (e.g., *E. coli*, MRSA, etc.) infection (e.g., the composition may be administered before, during, and/or after a microbial infection). The pharmaceutical compositions of the instant invention may also comprise at least one other antimicrobial agent (e.g., an antibiotic). The additional antimicrobial agent may also be administered in a separate composition from the antimicrobial peptides of the instant invention. The compositions may be administered at the same time or at different times (e.g., sequentially). The composition(s) comprising at least one anti-microbial peptide of the instant invention and the composition(s) comprising at least one additional antibiotic may be contained within a kit.

III. NUCLEIC ACID MOLECULES

Nucleic acid molecules encoding the anti-microbial peptides of the invention may be prepared by any method known in the art such as (1) synthesis from appropriate nucleotide triphosphates or (2) isolation and/or amplification from biological sources. The availability of nucleotide sequence information enables preparation of an isolated nucleic acid molecule of the invention by oligonucleotide synthesis. Indeed, knowledge of the amino sequence is sufficient to determine an encoding nucleic acid molecule. Synthetic oligonucleotides may be prepared by the phosphoramidite method employed in the Applied Biosystems 38A DNA Synthesizer or similar devices. The resultant construct may be purified according to methods known in the art, such as gel electrophoresis or high performance liquid chromatography (HPLC).

Nucleic acids of the present invention may be maintained in any convenient vector, particularly an expression vector. Different promoters may be utilized to drive expression of the nucleic acid sequences based on the cell in which it is to be expressed. Antibiotic resistance markers are also included in these vectors to enable selection of transformed cells. Anti-microbial peptide encoding nucleic acid molecules of the invention include cDNA, genomic DNA, RNA, and fragments thereof which may be single- or double-stranded. Thus, this invention provides oligonucleotides having sequences capable of hybridizing with at least one sequence of a nucleic acid molecule of the present invention.

Also encompassed in the scope of the present invention are oligonucleotide probes which specifically hybridize with the anti-microbial peptide nucleic acid molecules of the invention. Primers capable of specifically amplifying anti-microbial peptides encoding nucleic acids described herein are also contemplated herein. Such oligonucleotides are useful as probes and primers for detecting, isolating or amplifying anti-microbial peptide encoding nucleic acids.

IV. USES OF THE ANTI-MICROBIAL PEPTIDES

The present invention also encompasses pharmaceutical compositions comprising at least one anti-microbial peptide of the instant invention and at least one pharmaceutically acceptable carrier. Such a pharmaceutical composition may be administered, in a therapeutically effective amount, to a patient in need thereof. The pharmaceutical compositions of the present invention can be administered by any suitable route, for example, by injection (e.g., parenteral, intramuscular, intravenous, or intraperitoneal administration), by oral, pulmonary, nasal, topical, or other modes of administration such as controlled release devices. The composition may be directly administered (e.g., by injection) to the site of microbial infection. In general, pharmaceutical compositions and carriers of the present invention comprise, among other things, pharmaceutically acceptable diluents, preservatives, stabilizing agents, solubilizers, emulsifiers, adjuvants and/or carriers. Such compositions can include diluents of various buffer content (e.g., saline, Tris HCl, acetate, phosphate), pH and ionic strength; and additives such as detergents and solubilizing agents (e.g., Tween™ 80, Polysorbate 80), anti oxidants (e.g., ascorbic acid, sodium metabisulfite), preservatives (e.g., Thimersol, benzyl alcohol) and bulking substances (e.g., lactose, mannitol). The compositions can be incorporated into particulate preparations of polymeric compounds such as polylactic acid, polyglycolic acid, etc., or into liposomes. Such compositions may influence the physical state, stability, rate of in vivo release, and rate of in vivo clearance of components of a pharmaceutical composition of the present invention. Exemplary pharmaceutical compositions and carriers are provided, e.g., in "Remington's Pharmaceutical Sciences" by E. W. Martin (Mack Pub. Co., Easton, Pa.) and "Remington: The Science And Practice Of Pharmacy" by Alfonso R. Gennaro (Lippincott Williams & Wilkins) which are herein incorporated by reference. The pharmaceutical composition of the present invention can be prepared, for example, in liquid form, or can be in pill or dried powder form (e.g., lyophilized).

In yet another embodiment, the pharmaceutical compositions of the present invention can be delivered in a controlled release system, such as using an intravenous infusion, an implantable osmotic pump, a transdermal patch, liposomes, or other modes of administration. In a particular embodiment, a pump may be used (see Langer, supra; Sefton, CRC Crit. Ref. Biomed. Eng. (1987) 14:201; Buchwald et al., Surgery (1980) 88:507; Saudek et al., N. Engl. J. Med. (1989) 321:574). In another embodiment, polymeric materials may be employed (see Medical Applications of Controlled Release, Langer and Wise (eds.), CRC Press: Boca Raton, Fla. (1974); Controlled Drug Bioavailability, Drug Product Design and Performance, Smolen and Ball (eds.), Wiley: New York (1984); Ranger and Peppas, J. Macromol. Sci. Rev. Macromol. Chem. (1983) 23:61; see also Levy et al., Science (1985) 228:190; During et al., Ann. Neurol. (1989) 25:351; Howard et al., J. Neurosurg. (1989) 71:105).

The present invention also encompasses methods for preventing, inhibiting, and/or treating microbial infections (e.g., viral or bacterial), particularly *S. aureus* infections (e.g., MRSA). In a particular embodiment, the microbe is an antibiotic-resistant bacteria or an ESKAPE pathogen. In a particular embodiment, the microbe is selected from the group consisting of *Enterococcus faecium, Staphylococcus aureus, Klebsiella pneumoniae, Acinetobacter baumanii, Pseudomonas aeruginosa,* and *Enterobacter* species. The pharmaceutical compositions of the instant invention can be administered to an animal, in particular a mammal, more particularly a human, in order to treat/inhibit/prevent a microbial infection (e.g., the composition may be administered before, during, and/or after a microbial infection). The pharmaceutical compositions of the instant invention may also comprise at least one other anti-microbial agent, particularly at least one other antibiotic. The additional anti-microbial agent may also be administered in a separate composition from the anti-microbial peptides of the instant invention. The compositions may be administered at the same time and/or at different times (e.g., sequentially).

Bacterial infections that may be treated using the present methods include Gram-positive bacterial infection. In a particular embodiment, the bacteria is a staphylococcal strain. In yet another embodiment, the bacteria is *Staphylococcus aureus*. More particularly, the bacteria is MRSA. In a particular embodiment, the bacteria is an antibiotic-resistant bacteria or an ESKAPE pathogen. In a particular embodiment, the bacteria is selected from the group consisting of *Enterococcus faecium, Staphylococcus aureus, Klebsiella pneumoniae, Acinetobacter baumanii, Pseudomonas aeruginosa,* and *Enterobacter* species.

The dosage ranges for the administration of the compositions of the invention are those large enough to produce the desired effect (e.g., curing, relieving, treating, and/or preventing the microbial infection, the symptoms of it, or the predisposition towards it). The dosage should not be so large as to cause adverse side effects, such as unwanted cross-reactions, anaphylactic reactions, and the like. Generally, the dosage will vary with the age, condition, sex and extent of the disease in the patient and can be determined by one of skill in the art. The dosage can be adjusted by the individual physician in the event of any counter indications.

V. METHODS FOR GENERATING ANTI-MICROBIAL PEPTIDES

The instant invention also encompasses methods for generating anti-microbial peptides. In a particular embodiment, the method comprises 1) identifying a set of peptides having inhibitory activity against a microbe; 2) determining the most common length of the peptides within the set; 3) determining the most common amino acids (e.g., the most common 2, 3, 4, 5, or 6 amino acids (particularly the most common 4, 5, or 6 amino acids)) within the peptides within the set; 4) determining the most common net charge of the peptides within the set; 5) determining the most common range of hydrophobicity (e.g., within 5% ranges) of the peptides within the set; 6) determining the most common structure (e.g., α-helix, β-sheet, random, etc.) of the peptides in the set; and 7) designing the anti-microbial peptide which satisfies the criteria determined in steps 2) through 6). In a particular embodiment, the method further comprises identifying the most common motifs (e.g., 3 or 4 amino acid motifs) present in the peptides in the set and incorporating those motifs into the anti-microbial peptide. The methods may further comprise synthesizing the designed peptide and testing the peptide for the desired anti-microbial properties.

In one embodiment, the peptides may be obtained from the antimicrobial peptide database (aps.unmc.edu/AP/main.html). In a particular embodiment, the anti-microbial activity of the designed peptide is compared to the anti-microbial activity of the peptides within the set. The anti-microbial activity of the modified peptides may be measured by any method, such as measuring the ability of the peptide to kill the microbe.

In accordance with another aspect of the instant invention, the method for generating an anti-microbial peptide comprises 1) determining the three dimensional structure of a test peptide (e.g., by NMR structural analysis), 2) identifying hydrophobic defects within the three dimensional structure (e.g., identifying hydrophobic cavities causing reduced hydrophobicity of the peptide), and 3) replacing the amino acid(s) at the hydrophobic cavities with larger hydrophobic amino acids (inclusive of derivatives or analogs). Examples of larger hydrophobic amino acids are set forth hereinabove. The methods may further comprise synthesizing the designed peptide and testing the peptide for the desired anti-microbial properties. For example, the peptide may be tested for stability (e.g., resistance to proteases (e.g., chymotrypsin) and for anti-microbial activity (e.g., activity against one or more antibiotic-resistant pathogen or ESKAPE pathogen).

In another embodiment, the anti-microbial peptides are generated by filing the hydrophobic defect(s) within SEQ ID NO: 58. In a particular embodiment, the method comprises inserting a hydrophobic moiety at position $X_1$ and/or $X_2$ and testing the peptide for the desired anti-microbial properties. For example, the peptide may be tested for stability (e.g., resistance to proteases (e.g., chymotrypsin) and for anti-microbial activity (e.g., activity against one or more antibiotic-resistant pathogen or ESKAPE pathogen). In a particular embodiment, the hydrophobic moiety inserted at position $X_1$ and/or $X_2$ is larger than phenylalanine and/or is more hydrophobic than phenylalanine.

The following examples describe illustrative methods of practicing the instant invention and are not intended to limit the scope of the invention in any way.

Example 1

Natural antimicrobial peptides (AMPs) represent excellent antimicrobial candidates (Wang, G. (2010) Antimicrobial Peptides: Discovery, Design and Novel Therapeutic Strategies, CABI, England). Candidates from the antimicrobial peptide database have been screened and several anti-HIV peptides have been identified (Wang et al. (2004) Nucleic Acid Res., 32:D590-D592; Wang et al. (2009) Nucleic Acids Res., 37:D933-D937; Wang et al. (2010) Antimicrob. Agents Chemother., 54:1343-1346). Here, an ab initio design of potent anti-MRSA peptides is provided. All the parameters (e.g. peptide length, charge, and amino acid composition) for peptide design from the beginning were determined by database filtering technology (DFT). DFTamP1, the first AMP designed using this technology, consists merely of four types of frequently occurring amino acids (glycines, leucines, lysines, and serines). The peptide caused bacterial surface damage and killed community-associated MRSA USA300 rapidly. Structural determination of DFTamP1 by NMR spectroscopy revealed an eight-leucine membrane-targeting surface essential for killing Gram-positive MRSA. A combination of ab initio design with database screen led to novel peptides with enhanced potency. The designed peptides are also attractive leads because of their simple composition, short length, stability to proteases, and membrane targeting. All these advantages of the designed compounds make them ideal novel anti-MRSA therapeutics.

Natural antimicrobial peptides (AMPs) are essential host defense molecules discovered in bacteria, plants, and animals (Zasloff, M. (2002) Nature 415:389-395; Hancock et al. (2006) Nat. Biotechnol., 24:1551-1557; Brogden, K. A. (2005) Nat. Rev. Microbiol., 3:238-250). These polypeptides can adopt a variety of three-dimensional structures and constitute excellent templates for engineering a new generation of antimicrobials. Numerous methods have been developed for peptide design (Wang, G. (2010) Antimicrobial Peptides: Discovery, Design and Novel Therapeutic Strategies, CABI, England). The first method is natural template optimization via truncation or substitution (Wang, G. (2008) J. Biol. Chem., 283:32637-32643; Monincova et al. (2010) Amino Acids 39:763-775). The second method is sequence shuffling, i.e. changing the positions of amino acids in the sequence. This spans from sequence reversal to combinatorial library, where all the residues may be optimized (Cherkasov et al. (2009) ACS Chem. Biol., 4:65-74; Merrifield et al. (1995) Proc. Natl. Acad. Sci., 92:3449-3453; Li et al. (2006) Biochim. Biophys. Acta, 1758:1203-1214; Monroe et al. (2006) Peptides 27:2575-2584). The third method is motif hybridization. Examples include early cecropin-melittin hybrids to recent "Grammar"-generated peptides (Merrifield et al. (1995) Proc. Natl. Acad. Sci., 92:3449-3453; Haney et al. (2012) Biochim. Biophys. Acta 1818:762-775; Loose et al. (2006) Nature 443:867-869). Finally, novel AMPs can also be de novo or rationally designed from a few amino acids (e.g. KL peptides) (Blondelle et al. (1992) Biochemistry 31:12688-12694; Kang et al. (2009) J. Pept. Sci., 15:583-588; Chen et al. (2005) J. Biol. Chem., 280:12316-12329; Mangoni et al. (2011) Cell. Mol. Life Sci., 68:2267-2280).

Experimental Section

The Antimicrobial Peptide Database (aps.unmc.edu/AP/main.html)

To facilitate search, prediction, and design of AMPs, the APD was established in 2003 (Wang et al. (2010) Antimicrob. Agents Chemother., 54:1343-1346). The first version of the database contained 525 entries. The second version reported 1280 AMPs. As of February 2012, the updated APD registered 1954 AMPs. Natural peptides (<100 amino acids) will be collected into the database if their amino acid sequences and biological activity have been determined. The APD enabled a systematic search of peptide information, including peptide name, amino acid sequence, length, charge, hydrophobic content, structure, and biological activity. Users can search antibacterial, antifungal, antiviral (anti-HIV), anti-parasital, anticancer, spermicidal, insecticidal, and chemotactic data. These structure and activity filters in the APD provide a solid basis for this ab initio design.

Peptides and Hydrophobicity Measurements.

The peptides were chemically synthesized and purified (>95%) by GeneMed Synthesis, TX. One of the methods to estimate peptide hydrophobicity is to measure its retention time by HPLC (Chen et al. (2005) J. Biol. Chem., 280: 12316-12329; Wang et al. (2012) Biochemistry 51:653-664). This was done on a Waters HPLC system equipped with an analytical reverse-phase Vydac C18 column (250× 4.6 mm). The peptide was eluted by a linear gradient of acetonitrile (containing 0.1% TFA) from 5% to 95% at a flow rate of 1 ml/minute. The peptide peak was detected by UV at 220 nm.

Organisms and Antibacterial Activity Assays.

The bacterial strains used in the study are *Bacillus subtilis* 168, methicillin-resistant *Staphylococcus aureus* USA300 LAC (Gram-positive), *Escherichia coli* K12, and *Pseudomonas aeruginosa* PAO1 (Gram negative). The antibacterial activities of the peptides were determined using the standard broth microdilution method (Wang et al. (2005) J. Biol. Chem., 280:5803-5811). In brief, the bacterial culture (90 μL) was treated with a series of peptide solutions (10 μL), each with two-fold dilution. After overnight incubation at 37° C., the microplate was read on a ChroMate® 4300 Microplate Reader at 630 nm (GMI, Ramsey, Minn.). The MIC was defined as the lowest peptide concentration that fully inhibited bacterial growth.

Measurements of the Minimal Hemolytic Concentration.

Peptide hemolysis was assayed using an established protocol (Malmsten et al. (2011) PLoS One 6:e16400). In brief, fresh blood, obtained from the UNMC Blood Bank, was washed three times with PBS buffer and made into a 5% solution. To 90 μL of this solution, 10 μL of a peptide solution was added and incubated at 37° C. for one hour. After centrifugation at 13,000 rpm, aliquots of the supernatant were transferred to a fresh 96 well microplate. The absorbance of the solutions was measured at 545 nm to detect the amount of hemoglobin released. The percent lysis was calculated by assuming 100% release when treated with 2% Triton X-100 and no lysis (0%) when treated with PBS buffer. $HL_{50}$ was the peptide concentration that caused 50% lysis of human erythrocytes. The cell selectivity (CS) indexes were calculated as the ratio of $HL_{50}$ to the MIC of the peptide against *S. aureus* USA300.

Transmission Electron Microscopy.

*S. aureus* USA300 were grown in LB medium at 37° C. to the mid-logarithmic phase. Five mL of the culture was treated with the peptide DFTamp1 at 2× or 8×MIC for 1 hour. After washing with PBS, cells were fixed with a solution of 2% paraformaldehyde and 2% glutaraldehyde in 0.1 M PBS. The untreated control sample was processed in the same way. Ten μL of the bacterial suspension was adsorbed onto 200 mesh copper grids coated with formvar and silicon monoxide for 2 min, dried with the help of a blotting paper and then negatively stained by two drops of Nanovan® (Nanoprobes). Samples were observed in FEI Technai G2 TEM operated at 80 kV accelerating voltage.

Flow Cytometry.

Membrane permeation measurements were performed as described (Wang et al. (2012) Antimicrob. Agents Chemother., 56:845-856) using BacLight™ bacterial membrane potential kit (Molecular probes, Invitrogen) and a DNA-binding dye TO-PRO3 according to the manufacturer's guidelines on a FACSAria™ Flow Cytometer (BD Biosciences, San Jose, Calif.).

NMR Spectroscopy.

The NMR sample (0.3 mL) contained 2 mM peptide, 80 mM deuterated sodium dodecylsulfate (SDS), and 10% $D_2O$ as the field-locking signal. The pH of the NMR sample was adjusted to 5.4. Spectra were recorded on a 600-MHz Varian INOVA NMR spectrometer equipped with a triple-resonance cryogenic probe with a z-axis gradient capability. A set of 2D spectra, including NOESY, TOCSY, DQF-COSY, and natural abundance HSQC spectra, was recorded with the $^1H$, $^{15}N$, and $^{13}C$ carriers set at 4.77, 118.27, and 36.37 ppm, respectively. Thirty increments (128 scans) and 80 increments (256 scans) were collected for the $^{15}N$ (spectral width 2,200 Hz) and aliphatic $^{13}C$ (spectral width 12,000 Hz) dimensions, respectively. Chemical shifts were referenced as recommended (Markley et al. (1998) J. Biomol. NMR 12:1-23). Data were processed on a Silicon Graphics Octane workstation using NMRPipe (Delaglio et al. (1995) J. Biomol. NMR 6:277-293) and analyzed by PIPP (Garrett et al. (1991) J. Magn. Reson., 95:214-220).

Structure Calculations.

For structural calculations, major NMR restraints were derived from 2D NOESY spectra (Wüthrich, K. (1986)

NMR of proteins and nucleic acids, Wiley, New York, N.Y.) and converted to distance restraints 1.8-2.8, 1.8-3.8, 1.8-5.0, and 1.8-6.0 Å corresponding to strong, medium, weak, and very weak types of NOE peaks, respectively. Backbone angles were predicted based on $^1H\alpha$, $^{15}N$, $^{13}C\alpha$, and $^{13}C\beta$ chemical shifts as described (Wang et al. (2005) J. Biol. Chem., 280:5803-5811). An extended covalent structure was used as starting coordinates. In total, 100 structures were calculated using the simulated annealing protocol in the Xplor-NIH program (Schwieters et al. (2003) J. Magn. Reson., 160:65-73). Twenty structures were accepted and analyzed (Wang et al. (2012) Biochemistry 51:653-664).

Peptide Stability to Proteases.

Peptide stability was evaluated using standard SDS-PAGE (described in FIG. 5).

Results

Herein, a novel database-derived technology that enables one to design potent antimicrobials from the beginning is described. Peptide information in peptide databases allows users to effectively retrieve peptides with defined properties. In addition, peptides can be sorted according to key parameters such as length, charge and hydrophobicity. This feature makes it possible to locate the maximum in each case (FIG. 1, filled columns). These maxima represent the most probable parameters that determine the properties of natural AMPs. It is demonstrated here that these parameters can be merged to design novel peptides from the beginning. Because no assumption is taken in the design, this innovative approach is referred to as ab initio rather than de novo. A clear advantage of this ab initio approach is that the designed peptide is likely antimicrobial because it utilizes the most probable parameters of natural AMPs.

FIG. 1 depicts a pipeline of database search functions (or filters), each defining one parameter for the peptide. For short, this may be called pipeline database filtering technology. To illustrate this technology, novel compounds to combat Gram-positive bacteria (G+), especially MRSA, were designed due to its growing threat to the public health. At the time of the design, the activity filter selected 268 AMPs with anti-G+ activity from the APD. This set of AMPs was utilized as models to derive design parameters. To determine the peptide length, the number of peptides in a defined length group (step size 5) was plotted. The anti-G+ peptides with 11-15 residues were found to be dominant. A further analysis revealed that the majority of these peptides had a peptide length of 13 (FIG. 1B), which was thus determined as the most probable peptide length for the design. The third filter was used to determine the type of amino acids. To simplify the design, four representative amino acids (leucines, L; glycines, G; serines, S; and lysines, K) with the highest frequencies were selected (FIG. 1C). The general importance of G, S, and K can be appreciated from their high frequencies in the averaged amino acid profiles of 44 bacterial lantibiotics, 131 plant cyclotides, and 75 amphibian temporins (see FIG. 1G).

A fourth filter was introduced to determine the number of charged residues. A plot of peptide entries as a function of net charge showed that the largest anti-G+ group had a net charge of +1 (FIG. 1D), leading to the choice of one lysine. In addition to positive charge, hydrophobicity is another essential element in natural AMPs. Therefore, the hydrophobic content for the peptide was subsequently determined. FIG. 1E showed that most peptides possessed hydrophobic contents in the 61-65% range, which corresponded to eight leucines for a 13-residue peptide. With one K and eight L residues determined, there were only four additional residues (G or S) to be assigned. Two G and two S amino acids were assigned owing to their similar frequencies in FIG. 1C. Taken together, this 13-residue peptide designed here comprised 1K, 2G, 2S, and 8L.

There are numerous ways of combining this set of residues into unique peptide sequences. To reduce the possibilities, additional filters were utilized. FIG. 1F presented structure distribution of the anti-G+ peptides with 11-15 residues. All the known structures were helical. Therefore, the sixth filter suggested a helical conformation for the designed peptide. The seventh filter was introduced to help one decide on the model to build the helix. To reduce the possible combinations, a structure filter was utilized. FIG. 1F presents the number of anti-G+ peptides that form different secondary structures. The dominance of the α-helical conformation in this group indicated a similar structure for the designed peptide. In general, there are two models for building an amphipathic helix. In the first model, all hydrophobic residues are clustered at one end and all hydrophilic residues at the opposite side. In the second model, hydrophobic residues are interspersed with hydrophilic residues at every 2-3 residues. The motif search function was utilized in the APD to help to decide on the helix model. Motifs are a cluster of amino acid residues that occur frequently in natural AMPs. Because there was no peptide in this database that contained four or more leucines in a row, it is unlikely that the eight leucines could all appear at one end of the peptide sequence. This allowed for rejection of the first model and the design of the peptide according to the second model. The construction of a unique peptide sequence in the helical family requires the use of the motif filter (FIG. 1A). Table 1 provides further details. As the combinations LL, LLL, and LLLL occurred in 449, 11, and 0 AMP sequences in the APD, respectively, it is best to split the eight leucines into four pairs (i.e. LL-LL-LL-LL). To place G, S, and K into this leucine pattern, the three residue motifs were compared and it was found that GLL, KLL, and SLL are all well represented in the AMP database (GLL, 147; KLL, 69; and SLL, 58). Alternatives such as LLG, LLK, and LLS were rejected to avoid the generation of a string of LLLL, which does not occur in the APD. If three 3-residue motifs (GLL, KLL, and SLL) are chosen, a 4-residue motif is also possible to reach the 13-residue limit. The frequencies of possible 4-residue motifs were compared and GKLL was found to have the highest occurrence in the database. This led to four highly occurring motifs GLL, SLL, SLL, and GKLL that match the amino acid composition of the designed peptide. Logically, two peptide sequences are possible depending on whether the four motifs are connected in ascending (increase in frequency) or descending (decrease in frequency) order. Sequence 1 was arranged in the ascending order GKLL(41)-SLL(58)-SLL(58)-GLL(147), whereas sequence 2 was assembled in the descending order GLL (147)-SLL(58)-SLL(58)-GKLL(41) (frequency in parenthesis). Random combinations were rejected because they are in conflict with the spirit of the "rational design." Additional motifs were investigated that define the optimal connections between the above four motifs. There are three possible joints between the four motifs in each sequence. Two joints are identical (LL-S or L-SL) and only the C-terminal joints differ (LL-G or L-GL for sequence 1 and LL-G or L-GK for sequence 2). Because the linking motif LGK appeared more frequently in the database (89 counts) than LGL (31 counts), sequence 2 that contains LGK was thus established as the final sequence. Therefore, a novel peptide was obtained by selecting the most probable AMP parameters in each step of the design. The whole DFT pipeline arrived at the unique peptide sequence: GLLSLLSLLGKLL (SEQ ID NO: 1). This is the first antimicrobial peptide designed using DFT (hereinafter referred to as DFTamP1). This peptide is designed to target Gram-m positive bacteria by adopting a helical conformation. Hereinbelow, proof for both structure and activity of DFTamP1 are provided.

TABLE 1

Database motifs and their application in peptide design.

| Motifs | Maximum hits in the APD |
|---|---|
| I. The leucine motifs | |
| LL | 449 |
| LLL | 11 |
| LLLL | 0 |
| II. The 3-residue motifs containing "LL" | |
| GLL | 147 |
| LLG | 75 |
| SLL | 58 |
| LLS | 90 |
| KLL | 69 |
| LLK | 58 |
| III. The 4-residue motifs | |
| GKLL | 41 |
| KGLL | 6 |
| GSLL | 18 |

TABLE 1-continued

Database motifs and their application in peptide design.

| Motifs | Maximum hits in the APD |
|---|---|
| SGLL | 19 |
| GGLL | 25 |
| KSLL | 7 |
| SKLL | 1 |
| SSLL | 1 |
| IV. The joining motifs | |
| LLG | 75 |
| LLS | 90 |
| LSL | 37 |
| LGL | 31 |
| LGK | 89 |

Updated data were obtained from the antimicrobial peptide database (aps.unmc.edu/AP) (total AMP entries: 1954). These hits changed little during the peptide design. Motifs incorporated into DFTamP1 were underlined.

The in vitro activities of DFTamP1 were assayed using the standard microdilution method (Wang et al. (2005) J. Biol. Chem., 280:5803-5811). The peptide was found to be active against *S. aureus* USA300 with a minimal inhibitory concentration (MIC) of 3.1 µM. However, the peptide did not inhibit the growth of *B. subtilis*, *E. coli* or *P. aeruginosa* until 120 µM (Table 2). In the presence of DFTamP1, the continuous and round surface of *S. aureus* USA300 (FIG. 2A) was damaged and cell leakage (blebs) was detected by transmission electron microscopy (FIG. 2B, arrow). This cell leakage agreed with the results of flow cytometry (FIG. 2C), because surface damage by the peptide enabled the entrance of the DNA-binding dye into bacteria, leading to a steep fluorescence buildup in 30 minutes. Rapid killing of MRSA USA300 is also supported by killing kinetics experiments (FIG. 2J). These results indicate that the peptide acted on bacterial membranes (Wang et al. (2012) Antimicrob. Agents Chemother., 56:845-856).

TABLE 2

Bacterial minimal inhibitory concentration (MIC), selectivity index and hydrophobicity of database-derived anti-MRSA peptides. SA: *S. aureus* USA300; BS: *B. subtilis*; EC: *E. coli* K12; PA: *P. aeruginosa*.

| Peptide | Sequence[a] (SEQ ID NO) | MIC (µM) | | | | CS[b] | $t^{RP}$ (min)[c] |
|---|---|---|---|---|---|---|---|
| | | SA | BS | EC | PA | | |
| DFTamP1 | GLLSLLSLLGKLL (1) | 3.12 | >120 | >120 | >120 | 3.3 | 19.79 |
| DFTamP1-p | GLLPLLSLLGKLL (2) | 1.56 | 3.12 | 25 | >100 | 1.3 | 18.716 |
| DFTamP1-pi | GIIPIISIIGKII (3) | >34 | >30 | >34 | >30 | NA[d] | 17.565 |
| DFTamP1-pv | GVVPVVSVVGKVV (4) | >100 | >100 | >100 | >100 | NA | 12.364 |
| Temporin-PTa | FFGSVLKLIPKIL (5) | 3.12 | 6.25 | 25 | >100 | 40 | 14.498 |

TABLE 2-continued

Bacterial minimal inhibitory concentration (MIC), selectivity index and hydrophobicity of database-derived anti-MRSA peptides. SA: S. aureus USA300; BS: B. subtilis; EC: E. coli K12; PA: P. aeruginosa.

| Peptide | Sequence[a] (SEQ ID NO) | MIC (μM) | | | | CS[b] | t[RP] (min)[c] |
|---|---|---|---|---|---|---|---|
| | | SA | BS | EC | PA | | |
| Temporin-PTa (D-form) | FFGSVLKLIPKIL (6) | 3.12 | 6.25 | 25 | >100 | NA | 14.483 |
| Temporin-PTa6L | FFGSLLKLLPKLL (7) | 0.78-1.56 | 3.12 | 12.5 | 50-100 | 32 | 15.393 |
| Temporin-PTa8L | LLGSLLKLLPKLL (8) | 0.78-1.56 | 3.12 | 12.5 | >100 | 32 | 15.427 |
| DASamP1[e] | FFGKVLKLIRKIF (9) | 3.12 | >100 | >100 | >100 | 8 | 14.923 |

[a]The C-termini of the peptides are amidated.
[b]Cell selectivity index of the peptide.
[c]The HPLC retention time of the peptide.
[d]Not available.
[e]Database screening obtained antimicrobial peptide 1, which is a mutant of temporin-PTa (Conlon et al. (2008) Toxicon 52: 465-473).

To provide insight into the mechanism of membrane targeting, the three-dimensional structure of DFTamP1 was determined in membrane-mimetic micelles (Wûthrich, K. (1986) NMR of proteins and nucleic acids, Wiley, New York, N.Y.). In addition to 2D homonuclear NMR data (FIG. 2D), a natural abundance heteronuclear $^1$H and $^{15}$N correlated NMR spectrum was recorded (FIG. 2E). The heteronuclear data were very helpful in this case because of a high content of leucines in the peptide (61.5%). The data enabled both the substantiation of spectral assignments and structural refinement (Wang et al. (2005) Biol. Chem., 280:5803-5811). DFTamP1 was found to adopt an amphipathic helical structure (FIG. 2F), where hydrophilic and hydrophobic side chains were clustered on opposite faces (FIG. 2G,H). The C-terminal amide protons formed hydrogen bonds with the carbonyl oxygen of residue L9 (FIG. 2I). Statistics of the structure is summarized in Table 3. The fraying N-terminus of DFTamP1 (FIG. 2F) is consistent with sharp spectral lines for residues L2 to S4 (FIG. 2D). These dynamic data implied that residues L5-L13 of the peptide were more important for membrane binding. Collectively, the experimental data substantiated both the structure and activity of DFTamP1.

TABLE 3

Structural statistics of the designed peptide DFTamP1 in complex with sodium dodecylsulfate micelles.

| Structural restraints | DFTamP1 |
|---|---|
| no. of NOE restraints (total) | 99 |
| intra-residue | 38 |
| sequential | 38 |
| short-range | 23 |
| no. of backbone angles[a] | 20 |
| Structure and quality | |
| helical region | 3-12 |
| backbone rmsd (Å)[b] | 0.36 |
| NOE-derived distance violations (Å) | 0.3 |
| dihedral angle violations (deg) | 5 |

TABLE 3-continued

Structural statistics of the designed peptide DFTamP1 in complex with sodium dodecylsulfate micelles.

| Structural restraints | DFTamP1 |
|---|---|
| Ramachandran plot[c] | |
| residues in the most favored region (%) | 93.75 |
| residues in the additionally allowed region (%) | 3.75 |
| residues in the generously allowed region (%) | 2.50 |

[a]Predicted by the updated version of the TALOS program (Cornilescu et al. (1999) J. Biomol. NMR, 13: 289-302).
[b]Calculated by MOLMOL (Koradi et al. (1996) J. Mol. Graphics, 14: 51-55) when residues 2-20 of the accepted ensemble of 20 structures were superimposed.
[c]Calculated by Procheck (Laskowski et al. (1996) J. Biomol. NMR, 8: 477-486). Since ~94% of residues are in the most favored region, the structures have been determined to high quality.

Database analysis revealed that the sequence of DFTamP1 resembled amphibian temporins (Mangoni et al. (2011) Cell. Mol. Life Sci., 68:2267-2280), where position 3 is usually a proline residue (Table 4). When amino acid S4 was changed to a proline (i.e. DFTamP1-p), the peptide gained activity against B. subtilis and E. coli, underscoring the important role of this proline in determining the activity spectrum of the peptide (also cf. temporin-PTa and DASamP1, Table 2). To confirm the importance of the leucine surface of DFTamP1 (FIG. 2E) for bacterial targeting, the eight leucines were substituted with isoleucines or valines (Table 2). The isoleucine analog (DFTamP1-pi) was poorly soluble and showed no activity at the maximal concentration achieved. The valine analog (DFTamP1-pv) was also inactive. The results from real time bacterial killing confirmed that the valine analog was unable to kill MRSA even at a concentration 32-fold of the MIC of DFTamP1, while DFTamP1 showed killing at its MIC and bacteria were lysed and inhibited at 8-fold the MIC (FIG. 3). Thus, the leucine surface of DFTamP1 is critical for membrane targeting (FIG. 2H) and MRSA killing. The reduced activity of these peptide mutants could be attributed to a decrease in hydrophobicity (Table 2) (Chen et al. (2005) J. Biol. Chem., 280:12316-12329; Wang et al. (2012) Biochemistry 51:653-664).

TABLE 4

Sequence alignment, physical parameters and activity of the major types of Temporins.

| APD ID | Peptide name | Sequence Alignments | AA | P | L | Pho | RK | G+/G- | SEQ ID NO |
|---|---|---|---|---|---|---|---|---|---|
| 1534 | Temporin-SHf | ----FF--FLSRIF | 8 | 0 | 1 | 75 | 1 | Y/Y | 10 |
| 99 | Temporin L | -FVQWFSKFLGRIL | 13 | 0 | 2 | 61 | 2 | Y/Y | 11 |
| 101 | Temporin G | -FFPVIGRILNGIL | 13 | 1 | 2 | 61 | 1 | Y/Y | 12 |
| 110 | Temporin-1Lb | NFLGTLINLAKKIM | 14 | 0 | 3 | 57 | 2 | Y/N | 13 |
| 94 | Temporin A | -FLPLIGRVLSGIL | 13 | 1 | 4 | 61 | 1 | Y/N | 14 |
| 98 | Temporin F | -FLPLIGKVLSGIL | 13 | 1 | 4 | 61 | 1 | Y/Y | 15 |
| 97 | Temporin E | -VLPIIGNLLNSLL | 13 | 1 | 5 | 61 | 0 | Y/N | 16 |
| 859 | Temporin H | -LSP---NLLKSLL | 10 | 1 | 5 | 50 | 1 | Y/N | 17 |
| 858 | Temporin D | -LLPIVGNLLNSLL | 13 | 1 | 6 | 61 | 0 | n.f.[b] | 18 |
| 95 | Temporin B | -LLPIVGNLLKSLL | 13 | 1 | 6 | 61 | 1 | Y/N | 19 |
| 100 | Temporin K | -LLP---NLLKSLL | 10 | 1 | 6 | 60 | 1 | Y/N | 20 |
| 96 | Temporin C | -LLPILGNLLNGLL | 13 | 1 | 7 | 61 | 0 | Y/N | 21 |
| N.A.[b] | DFTamP1 | GLLSLL-SLLGKLL | 13 | 0 | 8 | 61 | 1 | Y/N | 1 |

[a]Leucines (L) are shaded, prolines (P) are underlined, and positively charged residues in italics. Alignment gaps (i.e. missing residues) are represented with dashes (-).
[b]Peptide sequences, their physical parameters and activity data were obtained from the APD. Additional information, including the original source, can be obtained by searching each entry in the database as well.
AA: number of amino acid residues; P: number of prolines; L: number of leucines; Pho: percent hydrophobic residues; RK, the sum of R and K residues;
G+, activity against Gram-positive bacteria; G-, activity against Gram-negative bacteria; Y, Yes; N, No; n.f.: not found;
N.A., not available.

To further test the importance of leucines, amphibian temporin-PTa was also used as a model peptide. The antimicrobial activity of temporin-PTa was not reported due to a limited amount of material (Conlon et al. (2008) Toxicon., 52:465-473). DASamP1, a temporin-PTa analog (Table 2), showed anti-MRSA activity both in vitro and in vivo. Here, it was found that temporin-PTa displayed an antibacterial spectrum comparable to DFTamP1-p. Furthermore, a D-form of temporin-PTa, consisting of all D-amino acids, was equally potent against MRSA, *E. coli*, and *B. subtilis*, substantiating a non-chiral bacterial target (Merrifield et al. (1995) Proc. Natl. Acad. Sci., 92:3449-3453). To mimic the leucine anchor of DFTamP1 (FIG. 2H), additional leucines were incorporated into temporin-PTa to obtain the 6L and 8L analogs (Table 2). These two leucine-rich analogs displayed improved antibacterial activity and retained a cell selectivity index of 32. In contrast, increasing positively charged residues did not improve peptide potency but reduced cell selectivity of DASamP1 (Table 2). Hence, mimicking the leucine anchor of DFTamP1 offers a useful strategy to enhance anti-MRSA potency.

In conclusion, potent anti-MRSA peptides were identified based on either database screening or ab intio design. The screen approach is costly due to the need to synthesize numerous peptides followed by antibacterial assays, whereas this DFT technology is cost effective since only the designed peptide was made. By combining these two database approaches, the anti-MRSA potency of the peptide was enhanced (MIC 0.78 μM) while retaining a cell selectivity index of 32. The practices not only uncovered the basics for peptide engineering but also led to the discovery of novel anti-MRSA candidates. Such peptides (Table 2) possess several attractive features. First, they have short sequences and simple amino acid compositions, allowing for cost-effective chemical synthesis. Second, membrane targeting of these peptides enabled us to synthesize an all D-amino acid analog, which showed equal antibacterial activities (Table 2) but superior stability to chymotrypsin. In FIG. 4, the band intensity of the D-form of the peptide changed little after 22 hour incubation, whereas the L-form was rapidly degraded in 2 hours. Third, a high hydrophobicity but low positive charge of these compounds constitutes another advantage because MRSA strains are known to deploy positive charges on their surface to evade the action of cationic AMPs (Andra et al. (2011) J. Biol. Chem., 286:18692-18700). Finally, the in vivo efficacy of DASamP1, an analog of temporin-PTa, in preventing biofilm formation in a mouse model is demonstrated herein. Therefore, these peptides are effective anti-MRSA drugs and also constitute useful templates for developing further anti-MRSA drugs. Note that partial database information was previously used to design novel antimicrobial peptides against E. coli (Wang et al. (2009) Nucleic Acids Res., 37:D933-D937) or HIV-1 (Wang et al. (2010) Antimicrob. Agents Chemother., 54:1343-1346; Wang et al. (2011) J. AIDS Clinical Res., S2:003). Therefore, the database tool can be harnessed to design novel antimicrobial agents against a variety of microbial pathogens.

Example 2

Based on database screening, six antimicrobial peptides (Ascaphin-8, DASamP1, DASamP2, lycotoxin I, maculatin 1.3, and piscidin 1) were identified that are highly potent against methicillin-resistant *Staphylococcus aureus* (MRSA) USA300. Among them, DASamP1 (database screened AMP 1) displayed bacteria-specific killing of MRSA in vitro, but not *Escherichia coli* K12, *Bacillus subtilis*, or *Pseudomonas aeruginosa*. Maculatin 1.3 showed Gram-specific activity against only Gram-positive bacteria tested. In addition, DASamP2, ascaphin-8, piscidin 1, and lycotoxin I displayed a broad-spectrum activity against both Gram-positive and Gram-negative bacteria. This is the first study that documents the activity of lycotoxin I against MRSA USA300. In addition, DASamP1 demonstrated in vivo efficacy in a mouse model of catheter-associated MRSA biofilm infection, where early biofilm establishment was suppressed.

Naturally occurring antimicrobial peptides (AMPs) are universal host defense molecules that have remained potent throughout the years (Boman, H. G. (2000) Immunol. Rev., 173:5-16; Hancock et al. (1998) Trends Biotechnol., 16:82-8; Lehrer, R. I. (2007) Curr. Opin. Hematol., 14:16-21; Zasloff, M. (2002) Nature 415:359-365). The Antimicrobial Peptide Database (APD, aps.unmc.edu/AP/main.html) collects a variety of such peptides from bacteria, fungi, plants, and animals (Wang et al. (2004) Nucleic Acids Res., 32:D590-2; Wang et al. (2009) Nucleic Acids Res., 37:D933-7). These peptides have been shown to be selectively or broadly active against bacteria, fungi, viruses, and/or parasites. Because AMPs rapidly eliminate microbes usually via membrane disruption, it is difficult or rare for them to develop resistance (Epand et al. (1999) Biochim. Biophys. Acta., 1462:11-28; Kamysz et al. (2003) Acta Biochim. Pol., 50:461-9; Hancock et al. (1998) Trends Biotechnol., 16:82-8). As a consequence, these natural peptides constitute promising templates for developing a new generation of antimicrobial agents.

To identify potent templates against MRSA, a group of 30 peptides selected from the APD was screened (Table 5). These peptides were chosen based on the following properties: First, the peptides are relatively short (<25 amino acid residues) and do not contain cysteines, allowing for cost effective chemical synthesis costs. Second, the peptides have a net positive charge. Cationic peptides are generally more active than anionic peptides because bacteria possess negatively charged surfaces. Third, the peptides are linear. Fourth, they do not have reported toxicity to mammalian cells. Finally, their effects on MRSA USA300 have not been tested. All the peptides used in this study were synthesized chemically and purified to >95% (GeneMed, TX). The quality of these peptides was verified prior to antimicrobial assays by RP-HPLC and concentrations were determined by UV spectroscopy.

TABLE 5

Antimicrobial peptides and their MICs (µM) against S. aureus USA300 and E. coli K12. SA: S. aureus USA300; EC: E. coli K12.

| Name (source) | Peptide sequence (SEQ ID NO) | SA | EC |
|---|---|---|---|
| Metalnikowin I (insect) | VDKPDYRPRPRPPNM (22) | >100 | >100 |
| Ranatuerin 9 (frog) | FLFPLITSFLSKVL (23) | 50 | >100 |
| Mastoparan M (insect) | INLKAIAALAKKLL (24) | >100 | 25 |
| Hyposin-5 (frog) | FRPALIVRTKGTRL (25) | >30 | >30 |
| Apidaecin IA (insect) | GNNRPVYIPQPRPPHPRI (26) | >100 | >100 |
| Drosocin (insect)[a] | GKPRPYSPRPTSHPRPIRV (27) | >100 | >100 |
| PGLa (frog) | GMASKAGAIAGKIAKVALKAL-NH$_2$[k] (28) | 25 | 25 |
| Clavanin B (tunicate) | VFQFLGRIIHHVGNFVHGFSHVF (29) | >100 | >100 |
| Buforin II (toad) | TRSSRAGLQFPVGRVHRLLRK (30) | >71 | >71 |
| Styelin A (tunicate) | GFGKAFHSVSNFAKKHKTA-NH$_2$ (31) | >100 | >100 |
| Ponericin L2 (insect) | LLKELWTKIKGAGKAVLGKIKGLL (32) | 85 | >25 |
| Spinigerin (insect) | HVDKKVADKVLLLKQLRIMRLLTRL (33) | >81 | >81 |

TABLE 5-continued

Antimicrobial peptides and their MICs (µM) against S. aureus USA300 and E. coli K12. SA: S. aureus USA300; EC: E. coli K12.

| Name (source) | Peptide sequence (SEQ ID NO) | SA | EC |
|---|---|---|---|
| Piscidin 1 (fish) | FFHHIFRGIVHVGKTIHRLVTG (34) | 3.1 | 12.5 |
| Pseudin 1 (frog) | GLNTLKKVFQGLHEAIKLINNHVQ (35) | >100 | 100 |
| Misgurin (fish) | RQRVEELSKFSKKGAAARRRK (36) | >84 | >84 |
| Lycotoxin I (spider) | IWLTALKFLGKHAAKHLAKQQLSKL (37) | 3.1 | 25 |
| Parasin I (fish) | KGRGKQGGKVRAKAKTRSS (38) | >84 | >84 |
| Brevinin-2-related (frog) | GIWDTIKSMGKVFAGKILQNL-NH$_2$ (39) | 25 | 25 |
| Maculatin 1.3 (frog) | GLLGLLGSVVSHVVPAIVGHF-NH$_2$ (40) | 6.2 | >100 |
| Latarcin 3a (spider) | SWKSMAKKLKEYMEKLKQRA (41) | >100 | >100 |
| Plantaricin chainA (bacteria)[b] | GAWKNFWSSLRKGFYDGEAGRAIRR (42) | >38.9 | >38.9 |
| Ascaphin-8 (frog) | GFKDLLKGAAKALVKTVLF-NH$_2$ (43) | 3.1 | 12.5 |
| Desertcolin 1 (frog) | GLADFLNKAVGKVVDFVKS-NH$_2$ (44) | >100 | >100 |
| Melectin (insect) | GFLSILKKVLPKVMAHMK-NH$_2$ (45) | 12.5-25 | 12.5-25 |
| Isracidin (cow) | RPKHPIKHQGLPQEVLNENLLRF (46) | >100 | >100 |
| DASamP1 (synthetic)[c] | FFGKVLKLIRKIF-NH$_2$ (9) | 3.1 | >100 |
| DASamP2 (synthetic)[d] | IKWKKLLRAAKRIL-NH$_2$ (47) | 6.2 | 3.1 |
| DASamP3 (synthetic)[e] | GWFDVVKHIAKRF-NH$_2$ (48) | 50 | 12.5 |
| DASamP4 (synthetic)[f] | NLVSGLIEARKYLEQLHRKLKNRKV (49) | >92 | >92 |
| DASamP5 (synthetic)[g] | SLSRFLRFLKIVYRRAF-NH$_2$ (50) | 12.5 | 25 |
| DASamP6[h] (synthetic) | IWLTALKFLGKHAAKHLAKQQL-NH$_2$ (51) | 3.1 | 12.5 |
| DASamP7[i] (synthetic) | IWLTALKFLGKHAAKHLL-NH$_2$ (52) | 1.6 | 12.5 |
| Temporin-PTa | FFGSVLKLIPKIL-NH$_2$ (5) | 3.1 | NE |
| DASamP9[j] (synthetic) | FFGRVLRLIRRIF-NH$_2$ (53) | 6.2 | NE |

[a] Residue T11 is not O glycosylated.
[b] The sequence of this peptide corresponds to chain A of plantaricin JK.
[c] A peptide mutant of temporin-PTa with S4K, P10R, and L13F mutations.
[d] A peptide mutant of polybia-MPI with the following mutations: D2K, D8R, and Q12R.
[e] This peptide was obtained by changing the last three residues SAV of uperin 7.1 to KRF.
[f] The sequence of this peptide corresponds to chain A of distinctin with residue C23 changed to R.
[g] A mutant of temporin-LTc with three mutations: S7R, P14R, and P15R.
[h] A mutant of lycotoxin I with C-terminal residues 23-25 deleted.
[i] A mutant of lycotoxin I with C-terminal residues 19-25 deleted and by changing A18 to L18.
[j] A analogue of DASamP1 where the K residues were replaced by R residues.
[k] The C-terminal amidation is represented by NH$_2$.

For the initial screen, antimicrobial activities of these peptides against S. aureus and E. coli were evaluated using the standard broth microdilution protocol (Wang, G. (2008) J. Biol. Chem., 283:32637-43). Table 1 lists the peptides and their MICs against E. coli K12 and S. aureus USA300. Six peptides, which are DASamP1, DASamP2, piscidin 1, lycotoxin I, maculatin 1.3, and ascaphin-8, were found to be active against S. aureus with an MIC in the range of 3.1 to 6.2 µM. Only two (DASamP1 and maculatin 1.3) of these six peptides failed to kill E. coli up to a concentration of 100 µM. Subsequently, the in vitro activity of these six peptides was evaluated against Bacillus subtilis and Pseudomonas aeruginosa (Table 6). While ascaphin-8, DASamP2, lycotoxin I, and piscidin 1 showed activity against both B.

subtilis and *P. aeruginosa*, maculatin 1.3 was active against *B. subtilis* but not *P. aeruginosa*. Interestingly, DASamP1 was active against neither *B. subtilis* and *P. aeruginosa*. Taken together, it was concluded that ascaphin-8, DASamP2, lycotoxin I, and piscidin 1 are wide-spectrum AMPs that are active against all of the Gram-positive and Gram-negative bacteria tested here. While maculatin 1.3 is active against two Gram-positive but not two Gram-negative bacterial strains, DASamP1 is species-specific since it active only against *S. aureus*. The finding that ascaphin-8, maculation 1.3, and piscidin 1 are wide-spectrum AMPs agrees with the literature (Apponyi et al. (2004) Peptides 25:1035-1054; Conlon et al. (2004) Biochem. Biophys. Res. Commun., 320:170-175; Silphaduang et al. (2001) Nature 414: 268-269; Souza et al. (2005) J. Immunol., 186:6585-6596). For lycotoxin I, it was previously found to active against Gram-negative *E. coli* and yeast (Yan et al. (1998) J. Biol. Chem., 273:2059-2066). This study, however, revealed its activity against Gram-positive *S. aureus*. There was no antibacterial data available for DASamP1, its wild-type peptide temporin-PTa (Conlon et al. (2008) Toxicon., 52:465-473) or DASamP2 (a peptide mutant of polybia-MPI (Souza et al. (2005) Peptides 26:2157-2164)) prior to the instant study.

TABLE 6

Antimicrobial and hemolytic activities of the six database-derived peptides.

| Peptide | Gram+ ($\mu M$)[1] | | Gram− ($\mu M$) | | $HL_{50}^2$ ($\mu M$) | $TI^3$ |
| --- | --- | --- | --- | --- | --- | --- |
| | $SA^1$ | BS | EC | PA | | |
| DASamP1 | 3.1 | >100 | >100 | >100 | 25 | 8 |
| DASamP2 | 6.2 | 12.5 | 3.1 | 6.25 | 75 | 12 |
| Piscidin 1 | 3.1 | 12.5 | 12.5 | 50 | 20 | 7 |
| Lycotoxin I | 3.1 | 6.25 | 25 | 25 | 125 | 40 |
| Maculatin 1.3 | 6.2 | 25 | >100 | >100 | 25 | 4 |
| Ascaphin-8 | 3.1 | 6.25 | 12.5 | 12.5 | 45 | 15 |

[1]Bacteria used are: SA, *S. aureus* USA300; BS, *B. subtilis*; EC, *E. coli* K12; and PA, *P. aeruginosa*. Bacterial minimal inhibitory concentrations are represented in MIC in $\mu M$.
[2]Concentration at which 50% red blood cells are lysed.
[3]Therapeutic index (TI) for *S. aureus* was calculated as $HL_{50}$/MIC.

The hemolytic effects of the six peptides were also compared on human red blood cells (hRBC) using an established protocol (Malmsten et al. (2011) PLoS One 6:e16400). The hemolytic activity of these peptides is in the following order: piscidin 1>DASamP1~maculatin 1.3>ascaphin-8>DASamP2>lycotoxin I. The therapeutic indexes (TI) of the six peptides were also calculated by taking the ratio between $HL_{50}$ and the MIC of the peptide against *S. aureus* USA300 (Table 6). A high TI indicates good cell selectivity. Lycotoxin I was observed to have the highest TI of 40. DASamP1, DASamP2, ascaphin-8, and piscidin 1 have a TI of approximately 10.

Because bacterial species specificity is an important feature in order to exempt probiotic bacteria from the killing list, additional analogs of DASamP1 were synthesized. When all the lysines were changed to arginines, the activity of DASamP8 increased slightly (Table 5). As a comparison, temporin-PTa itself showed an identical activity against MRSA to DASamP1. This is the first documentation of antimicrobial activity for temporin-PTa. The effect of sequence truncation on antibacterial activity of lycotoxin I was also evaluated. Interestingly, the shortened peptides (DASamP6 and DAsamP7) showed similar anti-MRSA activity to the wild type. Thus, the peptides can be shortened while retaining activity.

Figure 5A:
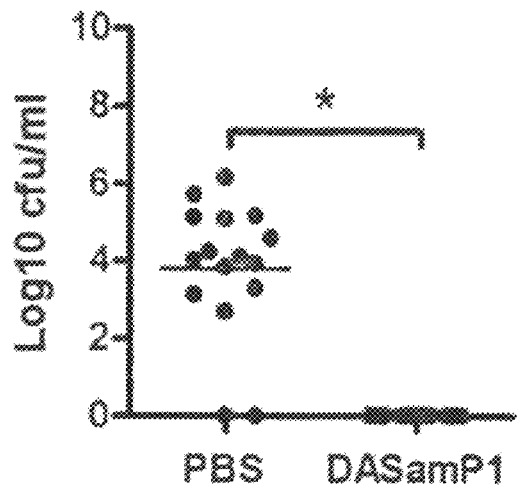
Figure 5B:
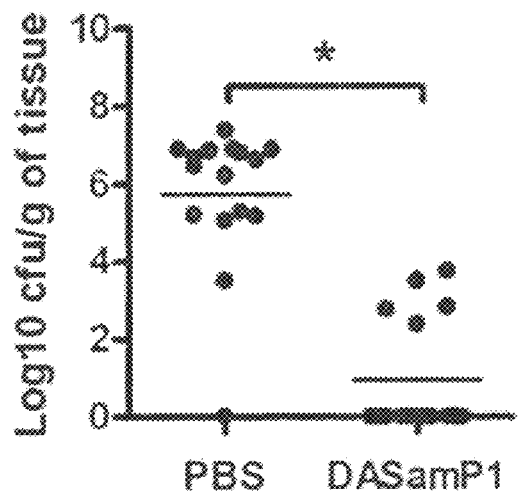
Figure 5C:
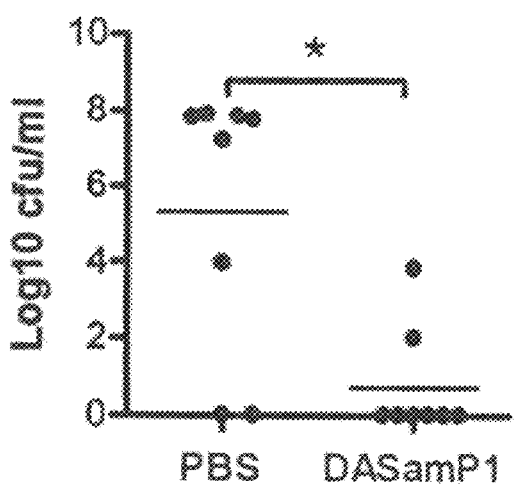
Figure 5D:
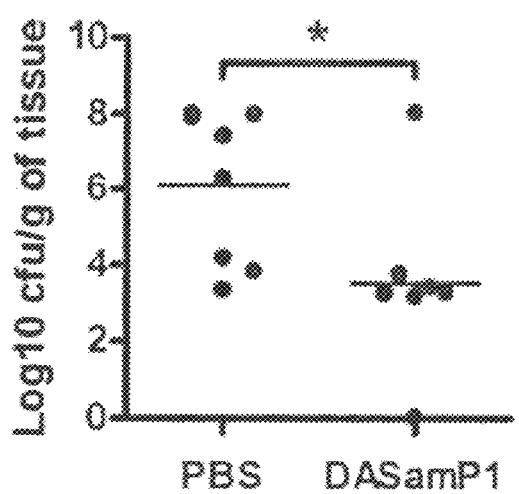

DASamP1 was chosen for further efficacy testing in vivo because this novel peptide is short, easy to synthesize, and displayed species-specific activity. Bacterial specificity is an important consideration in the search for novel antimicrobials to prevent cidal activity against probiotic bacteria. The in vivo efficacy of DAPamP1 against MRSA USA300 LAC was examined using a mouse model of catheter-associated biofilm infection as previously described (Cassat et al. (2007) Methods Mol. Biol., 391:127-144; Rupp et al. (1999) Infect. Immun., 67:2627-2632; Thurlow et al. (2011) J. Immunol., 186:6585-6596). C57BL/6 mice (Day 3, n=16/group; Day 14, n=8/group) were infected with $10^3$ colony forming units (cfu) of USA300 LAC::lux in the lumen of surgically implanted catheters to establish a biofilm infection. Animals were treated with 200 $\mu g$ peptide injected into the catheter at the time of infection (time 0) followed by 800 $\mu g$ peptide delivered at four different sites surrounding the catheter at 24 and 48 hours post-infection. Bacterial titers associated with catheter or surrounding host tissue were evaluated at day 3 (FIGS. 5A, 5B) and day 14 (FIGS. 5C, 5D) post-infection to determine the impact of peptide treatment on bacterial burdens. Mice treated with DASamP1 exhibited a significant decrease in bacterial burdens associated with biofilm-infected catheters (FIGS. 5A, 5C) as well as surrounding tissues compared to vehicle-treated mice (FIGS. 5B, 5D). Collectively, these findings demonstrate that DASamP1 provides an effective means to prophylactically reduce MRSA colonization and biofilm formation on artificial surfaces in vivo.

In conclusion, six potent AMPs against MRSA USA300 have been identified by screening 30 peptides selected from the antimicrobial peptide database. This screening led to the identification of bacteria species-specific peptide DASamP1, Gram-positive specific peptide maculatin 1.3, and broad-spectrum peptides, including DASamP2, ascaphin-8, piscidin 1 and lycotoxin I. Therefore, these peptides represent effective antimicrobials as well as templates for developing further generations of antimicrobials against microbes such as MRSA. In particular, DASamP1, the first database screening-generated AMP against *S. aureus*, is novel, easy to synthesize, and showed a potent effect on MRSA. Such properties made DASamP1 attractive as a template for developing a new generation of antimicrobials against *S. aureus*.

Example 3

One of the hurdles in developing peptide-based antimicrobials is peptide stability to protease (Wang, G. (2010) Antimicrobial Peptides: Discovery, Design and Novel Therapeutic Strategies, CABI, England). To identify useful starting templates, a protocol was developed that allows a simultaneous screening for antimicrobial activity as well as peptide stability. This was done by modifying the standard microdilution antimicrobial assays (Wang, G. (2008) J. Biol. Chem., 283:32637-32643). Specifically, the bacterial wells with a high peptide concentration (e.g. 100 $\mu M$) are duplicated (e.g., two for antimicrobial assays and two for protease stability assays). As an illustration, chymotrypsin was applied to the duplicated wells at a peptide:protease molar ratio of 25:1. Numerous peptides were screened in this manner. All the peptides were chemically synthesized using the solid-phase method and purified by HPLC to >95% (Genemed Synthesis, TX). The results of select peptides are provided in Table 7. KI-22 (Nell et al. (2006) Peptides 27:649-660) and GF-17 (Li et al. (2006) J. Am. Chem. Soc., 128:5776-5785) were found to be active against MRSA while GK-21 (Sigurdardottir et al. (2006) Antimicrob. Agents Chemother., 50: 2983-2989) was found to be weakly active against MRSA. Unfortunately, these peptides were degraded in the presence of chymotrypsin. However, the D-amino acid-containing GF-17 template (GF-17d3; Li et al. (2006) J. Am. Chem. Soc., 128:5776-5785) was resistant to the action of chymotrypsin as indicated by a successful suppression of the growth of *E. coli* K12 even in the presence of the protease.

TABLE 7

Screening for anti-MRSA peptides.

| Name | Peptide sequence[a] | SA[b] MIC (μM) | Stability[c] | SEQ ID NO |
|---|---|---|---|---|
| KI-22 | KIGKEFKRIVQRIKDFLRNLVP | 10 | − | 54 |
| GK-21 | GKEFKRIVQRIKDFLRNLVPR | 40 | − | 55 |
| GF-17 | GFKRIVQRIKDFLRNLV-amide | 2.5 | − | 56 |
| GF-17d3 | GFKRIVQRIKDFLRNLV-amide | − | + | 57 |

[a]Underlined residues are D-amino acids.
[b]SA, *S. aureus* USA300.
[c]All the peptides are active against *E. coli* K12. The sign "+" indicates the inhibition of *E. coli* growth even in the presence of chymotrypsin, where "−" indicates bacterial growth and peptide degradation.

As a consequence, GF-17d3 was chosen here as a template for developing anti-MRSA peptides. In the potential surface models of GF-17d3, a hydrophobic defect was more evident (FIG. 6). It was hypothesized that filling the hydrophobic defect with varying molecular moieties provides a practical approach to modulation of peptide activity. To test this hypothesis, different residues were utilized to replace the two F residues in A128A (Table 8). B128A was obtained by changing the first F of A128A to trifluoromethylphenylalanine. In C128A, however, the first F of A128A was substituted by biphenylalanine. In the case of D128A, both F's were replaced by biphenylalanine residues. Anti-MRSA assays showed that A128A was inactive (MIC>160 μM). However, both B128A and C128A gained activity against *S. aureus* USA300 with an MIC of 40 μM. D128A was most potent (MIC 5 μM) (Table 8). Likewise, anti-*E. coli* activity of the peptide series also increased (Table 8). Therefore, filling the hydrophobic defect with larger hydrophobic moieties indeed improved peptide activity against bacteria. In addition, the second F of A128A could also be altered to further enhanced peptide activity, although this mutation also increased the cytotoxicity of the peptide. In the case of A128A, B128A, and C128A, only 3-5% hemolysis was observed at 160 μM. D128A caused 50% lysis of red blood cells at 150 μM. These data could be converted to a therapeutic index, which equals hemolytic activity/MIC=150/5=30 for D128A. To understand the activity variation of these peptides, their retention times on a Waters reverse-phase HPLC system was also measured (Table 8). Because a longer retention time corresponds to higher hydrophobicity, the designed peptide became more hydrophobic from A128A to D128A (Table 8). It is proposed that the increase in antibacterial and hemolytic activity resulted from increased peptide hydrophobicity.

TABLE 8

Antimicrobial and hemolytic activity of the designed peptides.

| Peptide[a] (SEQ ID NO) | *E. coli* K12 MIC (μM) | *S. aureus* USA 300 MIC (μM) | HL$_{50}$ (μM)[b] | t$_R$ (min) |
|---|---|---|---|---|
| A128A (HC-15) (59) | 10 | >160 | <3% | 9.95 |
| B128A (HC16) (60) | 5 | 40 | <5% | 10.32 |
| C128A (61) | 5 | 40 | <5% | 10.55 |
| D128A (62) | 2.5 | 5 | 150 | 11.26 |

[a]The A128A peptide ($X_1 = X_2 = F$) template, GX$_1$KRLVQRLKDX$_2$LRNLV-amide (SEQ ID NO: 58), was obtained by substituting isoleucines with leucines in GF-17d3. In addition, the three underlined leucines at positions 5, 9, and 13 are D-amino acids. Other peptides were designed by using different combinations of $X_1$ and $X_2$ residues (B128A, $X_1$ = CF$_3$-subtituted phenylalanine (F) and $X_2$ = F; C128A $X_1$ = biphenylalanine and $X_2$ = F; D128A, $X_1 = X_2$ = biphenylalanine).
[b]The peptide concentration at which 50% human red blood cells were lysed.

Finally, the efficacy of the peptides was also shown in vivo. C57BL/6 mice received 4 injections (200 μg each) of D128A or PBS vehicle at 12, 24, and 48 hours following *S. aureus* infection, whereupon bacterial titers associated with infected catheters and surrounding tissues were quantitated at day 3 or 14 post-infection (FIG. 7). In both cases, the growth of the bacterium was entirely inhibited. These experiments demonstrate that D128A is also potent against MRSA in a mouse model.

In conclusion, D128A was engineered based on GF-17d3. D128A differs from GF-17d3 (derived from LL-37) by positions 17, 20, 24, and 27. These alterations improved peptide activity and reduced peptide production cost. By repairing the hydrophobic defect, D128A was found to be potent against both Gram-positive *E. coli* and Gram-positive MRSA USA300 both in vitro and in vivo. The broad-spectrum peptide showed a therapeutic index of 30.

Example 4

A hallmark of emerging difficult-to-treat clinical superbugs is their ability to "escape" the action of multiple traditional antibiotics, in part due to biofilm formation in the host. The ESKAPE pathogens include *Enterococcus faecium, Staphylococcus aureus, Klebsiella pneumoniae, Acinetobacter baumanii, Pseudomonas aeruginosa*, and *Enterobacter* species (Boucher et al. (2009) Clin. Infect. Dis., 48:1-12). According to the Centers for Disease Control and Prevention, the six ESKAPE bacterial species cause two-thirds of health care-associated infections, leading to 99,000 deaths annually in the United States. *S. aureus* infections alone cause a comparable number of deaths as human immunodeficiency virus type 1 (HIV-1) (Klevens et al. (2007) J. Am. Med. Assoc., 298:1763-1771). Antimicrobial peptides (AMPS) are host defense molecules that have maintained antimicrobial activity for millions of years by keeping pace with the evolution of bacterial resistance mechanisms. This feature makes them appealing candidates for developing new antibacterial compounds (Zasloff, M. (2002) Nature 415:389-395; Lai et al. (2009) Trends Immunol., 30:131-141; Hancock et al. (2013) Curr. Opin. Microbiol., 16:519-521).

The protective effect of human LL-37 against infection is underscored by both clinical observations and recent findings from animal models (van der Does et al. (2012) J. Leukocyte Biol., 92:735-742; Putsep et al. (2002) Lancet 360:1144-1149; Chromek et al. (2006) Nat. Med., 12:636-641). Therefore, there is growing interest in its medical use. Interestingly, sunlight triggers the biosynthesis of dihydroxyvitamin D in skin that binds the vitamin D receptor to initiate peptide expression (van der Does et al. (2012) J. Leukocyte Biol., 92:735-742). At the moment, clinical trials of vitamin D as an anti-infective agent have not demonstrated efficacy (Nakatsuj et al. (2012) J. Invest. Dermatol., 132:887-895). Another avenue is to administer LL-37 at infected sites. Cationic LL-37 possesses a long amphipathic helical structure covering residues 2-31 that recognizes and disrupts anionic bacterial membranes (FIG. 8A) (Wang, G. (2008) J. Biol. Chem., 283:32637-32643; Oren et al. (1999) Biochem. J., 341:501-513; Wang et al. (2014) Biochim. Biophys. Acta 1838:2160-2172). To minimize the cost for peptide synthesis, active fragments, including GF-17 corresponding to the major antimicrobial region (residues 17-32), have been reported (Wang et al. (2014) Biochim. Biophys. Acta 1838:2160-2172; Braff et al. (2005) J. Immunol., 174:4271-4278; Nagaoka et al. (2005) Inflammation. Res., 54:66-73; Li et al. (2006) J. Am. Chem. Soc., 128:5776-5785). Since these natural peptides lack sufficient stability to proteases, human LL-37 was re-engineered into peptide analogues with potency, stability, and cell selectivity against superbugs.

Methods

Peptides and Hydrophobicity Measurements

All peptides were chemically synthesized at purity of > 95% (Genemed Synthesis Inc.). Peptide hydrophobicity was estimated by measuring its retention time on a Waters HPLC system equipped with an analytical reverse-phase Vydac® C18 column (250 mm×4.6 mm) (Mishra et al. (2012) J. Am. Chem. Soc., 134:12426-12429). Briefly, the peptide was eluted by a linear gradient of acetonitrile (containing 0.1% TFA) from 5% to 95% at a flow rate of 1 ml/min. The peptide peak was detected by UV at 220 nm.

Antibacterial Activity Assays

The antibacterial activities of the peptides were determined using the standard broth microdilution method (Mishra et al. (2012) J. Am. Chem. Soc., 134:12426-12429; Wang et al. (2005) Biol. Chem., 280:5803-5811). Briefly, the bacterial culture was treated with a series of peptide solutions, each with two-fold dilution. After overnight incubation at 37° C., the microplate was read on a ChroMate® 4300 Microplate Reader at 630 nm (GMI, Ramsey, Minn.). The MIC was defined as the lowest peptide concentration that fully inhibited bacterial growth.

Hemolytic Assays

Peptide hemolysis was assayed using an established protocol (Menousek et al. (2012) Int. J. Antimicrob. Agents 39:402-406; Malmsten et al. (2011) PLoS One 6:e16400). Briefly, blood cells were washed three times with phosphate-buffered saline (PBS) and were diluted to a 5% solution. Following peptide treatment, incubation at 37° C. for 1 hour and centrifugation at 13,000 rpm, aliquots of the supernatant were transferred to a fresh 96-well microplate. To assess peptide cytotoxicity, the amount of hemoglobin released was measured at 545 nm. Percent lysis was calculated by assuming 100% release when human blood cells were treated with 2% Triton X-100 and 0% release when they were incubated with PBS buffer.

Transmission Electron Microscopy (TEM)

*S. aureus* USA300 were grown in LB medium at 37° C. to the mid-logarithmic phase. The samples were prepared (Mishra et al. (2012) J. Am. Chem. Soc., 134:12426-12429) and observed in an FEI Technai™ G2 TEM operated at 80 kV accelerating voltage at the University of Nebraska Medical Center (UNMC).

Flow Cytometry

Membrane permeation analysis was performed by using the BacLight™ bacterial membrane potential kit (Invitrogen) on a FACSAria™ flow cytometer (Wang et al. (2012) Antimicrob. Agents Chemother., 56:845-856). In short, logarithmic growth-phase cultures of *S. aureus* USA300 (0D600, 0.6-1.0), after being washed twice and resuspended in PBS (0.2 µm filter-sterilized) (~5×10$^8$ CFU/mL), were treated at 80 µM concentration of the peptides in FIG. 8F and 20 µM in FIG. 11. Bacteria were then treated for 10 minutes with 3,3'-diethyloxacarbocyanine iodide [DiOC$_2$(3)] (30 µM)/TO-PRO®-3 (100 nM) dye mixture. Data were analyzed with FlowJo software.

Peptide Stability to the Action of Proteases

Peptide stability was evaluated based on a published protocol (Mishra et al. (2012) J. Am. Chem. Soc., 134: 12426-12429) with one modification. Aliquots (10 µL) of the reaction solutions (peptide/protease molar ratio, 40:1) in 10 mM PBS buffer (pH 8) at 37° C. were taken at 0, 6, and 24 hours and immediately mixed with 10 µL of 2×SDS loading buffer followed by boiling for 5 minutes to stop the reaction. Samples were analyzed using 5% stacking/18% resolving tricine gel.

*S. aureus* Biofilm Infection Model

Male C57BL/6 mice, 6-8 weeks old, were anesthetized with tribromoethanol (avertin), and the skin was shaved and scrubbed with povidone-iodine. A small subcutaneous (sc) incision was made in the left flank and a blunt probe was used to create a pocket for insertion of a sterile 14-gauge Teflon catheter 1 cm in length. The incision was sealed and 1,000 CFU USA300 LAC::lux in 20 µL of sterile PBS was slowly injected through the skin into the infected catheter lumen. Animals were initially treated with 200 µg peptide, dissolved in PBS, injected into the catheter at the time of infection (time 0) followed by 200 µg peptide injected subcutaneously at four different sites surrounding the catheter at 24 and 48 hours postinfection. At days 3 and 14 postinfection, catheters were removed in order to quantitate bacterial burdens. Catheters were sonicated in 1 mL of PBS to dissociate the biofilm from the intra- and extraluminal surfaces. The tissue surrounding the catheter was also removed, weighed, and homogenized in 500 µL homogenization buffer. Bacterial titers associated with catheters and surrounding tissues were quantified by plating on blood agar plates. To compare the expression of inflammatory mediators associated with biofilm-infected tissues treated with the novel antimicrobial peptides, a mouse microbead array or ELISA detection kit was utilized according to the manufacturer's instructions. Results were normalized to the amount of total protein recovered to correct for differences in tissue sampling size.

Results

To identify protease-resistant peptide templates, 30 synthetic peptides were screened (Table 9; Wang et al. (2008) Antimicrob. Agents Chemother., 52:3438-3440). A standard microdilution assay protocol (Li et al. (2006) J. Am. Chem. Soc., 128:5776-5785) was modified to include proteases into the duplicated wells with high concentrations of peptide so that both antimicrobial activity and protease stability could be evaluated simultaneously. In this setup, most of the LL-37 peptides showed bactericidal effects in the absence of the protease but became inactive in the presence of chymotrypsin after overnight incubation at 37° C. (peptide: protease molar ratio of 40:1). However, GF-17d3, a GF-17-derived peptide with incorporation of three D-amino acids at positions 20, 24, and 28 (numbered as in LL-37) (Wang et al. (2014) Biochim. Biophys. Acta, 1838:2160-2172), retained antimicrobial activity against *Escherichia coli* K12 (Table 9). In contrast, another two peptide analogues containing one to two D-amino acids at positions 20 or both 20 and 24 were not stable. Peptide stability improvement due to the incorporation of D-amino acids into other peptides has been observed (Papo et al. (2003) Biochemistry 42:9346-9354). Compared to GF-17, GF-17d3 lost antibacterial activity against *S. aureus* USA300 LAC (Epand et al. (2009) Antimicrob. Agents Chemother., 53:3705-3714; Wang et al. (2012) Antimicrob. Agents Chemother., 56:845-856). This protease-resistant template was selected for subsequent engineering of peptides for activity against *S. aureus* as well as other ESKAPE pathogens.

TABLE 9

Simultaneous Screening for Antibacterial and Protease-Resistant Peptides.

| Name | Peptide amino acid sequence[a] | MIC (µM) | Stability[b] | SEQ ID NO |
|---|---|---|---|---|
| FK-21 | FKRIVQRIKDFLRNLVPRTE | 160 | – | 64 |
| GK-21 | GKEFKRIVQRIKDFLRNLVPR | 40 | – | 55 |
| KI-22 | KIGKEFKRIVQRIKDFLRNLVP | 10 | – | 54 |
| EK-20 | EKIGKEFKRIVQRIKDFLRN | >160 | – | 65 |
| GF-17 | GFKRIVQRIKDFLRNLV | 2.5 | – | 56 |
| GF-16 | GFKRIVQRIKDFLRNL | 10 | – | 66 |
| BMAP-18 | GRFKRFRKKFKKLFKKLS | >160 | – | 67 |
| GF-17d3 | GFKRIVQRIKDFLRNLV | >160 | +[c] | 57 |

[a]The C-termini of GF-16, GF-17, and BMAP-18 are amidated.
[b]Peptide stability was obtained during antimicrobial assays in the presence of chymotrypsin (peptide:protease molar ratio 40:1).
[c]For peptides that are inactive against *S. aureus* USA300, the stability to chymotrypsin was evaluated using *E. coli* K12. Amino acids in bold are D-amino acids. Considering the material cost of D-isoleucines, the D-amino acids I20 and I24 in GF-17d3 were replaced with D-leucines. The resulting new peptide template (sequence $GX_1KRLVQRLKDX_2LRNLV$ (SEQ ID NO: 58)) is hereinafter referred to as 17F2 (a 17-residue peptide with two phenylalanines, i.e. $X_1 = X_2 = F$; SEQ ID NO: 59).

A rational design was conducted on the basis of the 3D structure of GF-17d3. NMR structural analysis revealed that the three D-amino acids distorted the regular helical backbone structure of GF-17 (FIG. 8B) (Nagaoka et al. (2005) Inflammation Res., 54:66-73) into a novel nonclassic amphipathic structure of GF-17d3 (FIG. 8C) (Li et al. (2006) J. Am. Chem. Soc., 128:5776-5785). The noncoherent packing of the GF-17d3 side chains caused a hydrophobic defect in the structure (FIGS. 8C and 8D, arrow), leading to reduced hydrophobicity. Accordingly, it was hypothesized that the antimicrobial activity of this peptide 17F2 (sequence $GX_1KRLVQRLKDX_2LRNLV$ (SEQ ID NO: 58), Table 9) could be enhanced by filling in the hydrophobic cavity (FIG. 8D, arrow) with a larger hydrophobic side chain. The antimicrobial activities of these peptide analogues were evaluated using the standard microdilution assays (Mishra et al. (2012) J. Am. Chem. Soc., 134:12426-12429), and the minimal inhibitory concentrations (MIC) against a panel of the ESKAPE pathogens are provided in Table 10. 17F2 inhibited *E. coli*, *A. baumannii*, and *E. cloacae* (MIC 6.2-25 µM) but not *S. aureus*, *E. faecium*, *K pneumoniae*, or *P. aeruginosa* until 100 µM or higher. When $X_1$ was replaced with 4-trifluoromethylphenylalanine (mF), the resultant peptide 17mF-F displayed MICs in the range of 25-50 µM against most of the ESKAPE strains and 3.1-6.2 µM against *A. baumannii*. When $X_2$ of 17F2 was mutated to 2-naphthylalanine (Naph), the new peptide 17F-Naph became active against *E. faecium* and *A. baumannii* (MIC 3.1 µM). When both the above substitutions were made at $X_1$ and $X_2$, the activity of the resultant peptide 17mF-Naph was further increased, especially against MRSA USA300 (MIC 6.2 µM). To compare the two sites, these two substitutions at positions $X_1$ and $X_2$ were swapped to obtain 17Naph-mF. Interestingly, 17mF-Naph and 17Naph-mF have an essentially identical antibacterial activity spectrum based on MICs (Table 10). In addition, biphenylalanines were incorporated at position $X_1$ alone or at both $X_1$ and $X_2$ of the 17F2 template. While 17BIPHE with one replacement was more active against *S. aureus* than 17mF-F, 17BIPHE2 with two replacements showed the highest antibacterial activity against all of the ESKAPE pathogens (MIC 3.1-6.2 µM). Killing kinetics assays revealed that 17BIPHE2 was able to eliminate *P. aeruginosa* PAO1 in 30 minutes and *S. aureus* USA300 in 90 minutes (FIG. 9). The killing abilities of these peptides are essentially proportional to their MIC values as well as retention times (a measure of hydrophobicity) on a reverse-phase HPLC column (Mishra et al. (2012) J. Am. Chem. Soc., 134:12426-12429). Hence, the structure-based design produced a family of antimicrobials against the ESKAPE pathogens (Table 10).

TABLE 10

Minimal Inhibitory Concentration (MIC), Cytotoxicity, and Hydrophobicity of a Series of Peptides Designed Based on Human Cathelicidin LL-37.

| Peptide (SEQ ID NO) | MIC (µM) | | | | | | $HL_{50}$ (µM)[b] | $t_R$ (min)[c] |
|---|---|---|---|---|---|---|---|---|
| | $EF^a$ | SA | KP | AB | PA | EC | | |
| 17F2 (59) | >100 | >100 | >100 | 6.2-12.5 | 100 | 25 | >900 | 9.95 |
| 17mF-F (60) | 25-50 | 25 | 50 | 3.1-6.2 | 25 | 25 | >900 | 10.32 |
| 17F-Naph (68) | 3.1 | 25 | 25 | 3.1 | 12.5 | 12.5 | >900 | 10.56 |
| 17mF-Naph (69) | 3.1 | 6.2 | 12.5 | 3.1 | 6.2-12.5 | 6.2 | 500 | 10.99 |
| 17Naph-mF (70) | 3.1 | 6.2 | 12.5 | 3.1 | 6.2-12.5 | 6.2-12.5 | 950 | 10.94 |
| 17BIPHE (61) | 12.5 | 12.5 | 25 | 3.1 | 12.5 | 12.5 | >900 | 10.55 |
| 17BIPHE2 (62) | 3.1 | 3.1 | 3.1 | 3.1 | 6.2 | 3.1 | 225 | 11.26 |

[a]Abbreviations used: EF, *E. faecium* ATCC51559; SA, *S. aureus* USA300 LAC; KP, *K. pneumonia* ATCC13883; AB, *A. baumannii* B2367-12; PA, *P. aeruginosa* PAO1; EC, *E. cloacae* B2366-12.
[b]The peptide concentration (µM) that causes 50% lysis of human erythrocytes.
[c]HPLC retention time of the peptide.

In developing peptide-based antimicrobials, it is essential to minimize potential cytotoxicity to human cells. It was found that 17F2 and various single substitution variants displayed poor hemolytic ability, with a 50% hemolysis concentration ($HL_{50}$) greater than 900 µM (Table 10). However, the substitution swapped pair, 17mF-Naph and 17Naph-mF, gave different $HL_{50}$ concentrations of 500 and 950 µM, respectively. 17BIPHE2, the most potent peptide, showed an $HL_{50}$ of 225 µM. Relative to the MIC value (3.1 µM) that inhibited the majority of these ESKAPE pathogens, a cell selectivity index (i.e., the ratio between $HL_{50}$ and MIC) of 72 was obtained, meaning that 17BIPHE2 is not cytotoxic at the MIC. If the same MIC of 3.1 µM was used, the cell selectivity indices for 17mF-Naph and 17Naph-mF were 161 and 306, respectively. Notably, 17Naph-mF, with a better selectivity index, is also more efficient in killing MRSA than 17mF-Naph (FIG. 9). Thus, there is an excellent therapeutic window to utilize these novel compounds to treat infections caused by the ESKAPE pathogens.

To validate the stability of the engineered peptides, the degradation kinetics of 17BIPHE2 in the presence of chymotrypsin was studied by SDS-PAGE. While a GF-17 analogue (Wang et al. (2012) Antimicrob. Agents Chemother., 56:845-856) was rapidly digested in 4 hours ($t_{1/2}$<0.5 hour), the level of intact 17BIPHE2 remained constant during this time period (FIG. 8E). Furthermore, 17BIPHE2, but not GF-17, was also stable for at least 24 hours in the presence of S. aureus V8 protease or fungal protease K (FIG. 10). Thus, 17BIPHE2 is stable to the action of several proteases.

Figure 8H:
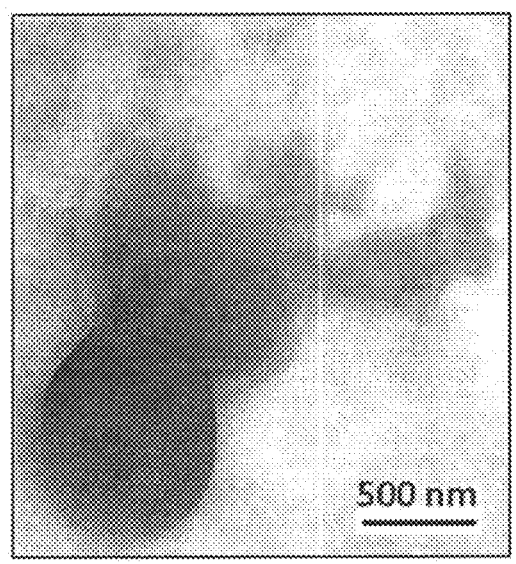

To determine the killing mechanism of 17BIPHE2, flow cytometry studies were conducted. When bacterial membranes are compromised, flow cytometry can follow the cellular entry of the nonpermeable dye TO-PRO®3, which upon binding bacterial DNA leads to a rapid increase in fluorescence (Wang et al. (2012) Antimicrob. Agents Chemother., 56:845-856). At 80 µM, this was indeed the case with 17BIPHE and 17BIPHE2 (FIG. 8F), which were comparable to GF-17, a peptide known to target bacterial membranes. At a lower peptide concentration (20 µM), the killing ability of peptides was found to be inversely proportional to the MIC (FIG. 11). To validate membrane damage, transmission electron microscopy (TEM) was used to directly visualize possible damage to bacteria (Mishra et al. (2012) J. Am. Chem. Soc., 134:12426-12429). While untreated bacteria possessed a uniform membrane architecture (FIG. 8G), the addition of 17BIPHE2 caused bacterial lysis (FIG. 8H).

Figure 8I:
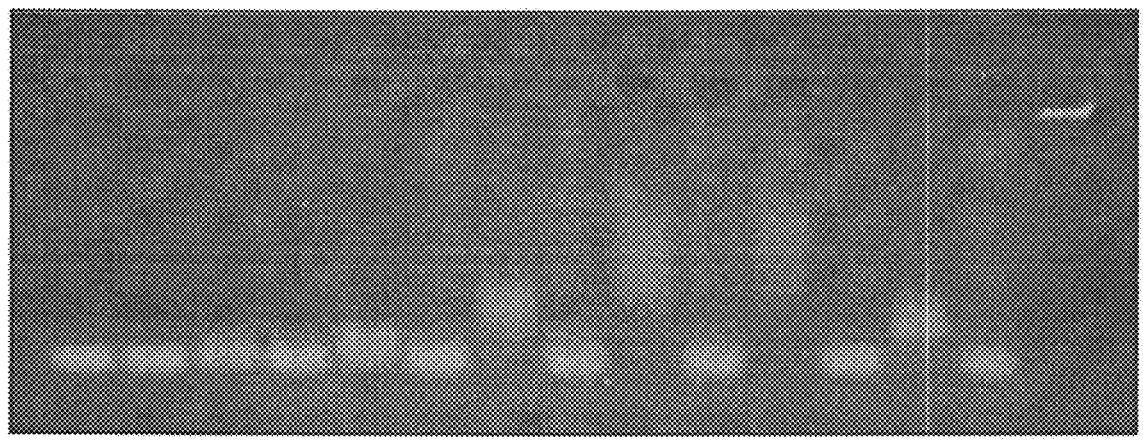

Bacterial membrane damage raised the possibility that 17BIPHE2 might also enter cells and bind DNA. To provide evidence for this, gel retardation experiments were used (Park et al. (1998) Biochem. Biophys. Res. Commun., 244:253-257). While 17F2 did not bind to DNA in this assay, 17BIPHE2 at 12 µM was trapped in the wells (FIG. 8I). At the same concentration, both 17BIPHE and 17F-Naph, with a single substitution, retarded DNA to a similar degree. 17mF-Naph and 17NaphmF, with the two substitutions swapped, behaved similarly. Thus, this family of peptide analogues possesses a wide range of DNA retarding abilities. Interestingly, the extent of DNA retardation (correlating to the amount of peptide associated with DNA) is proportional to bacterial killing ability, with 17BIPHE2 being the strongest and 17F2 the poorest. A similar trend was observed using the DNA purified from P. aeruginosa PAO1 (FIG. 12). These correlations indicate that DNA binding may be part of the mechanism of bacterial killing.

The in vivo efficacy of 17BIPHE2 against S. aureus USA300 LAC was examined using a mouse model of catheter-associated biofilm infection (Menousek, et al. (2012) Int. J. Antimicrob. Agents 39:402-406; Cassat et al. (2007) Methods Mol. Biol., 391:127-144; Heim et al. (2014) Methods Mol. Biol., 1106:183-191; Thurlow et al. (2011) J. Immunol., 186:6585-6596). Animals used in this study were cared for by following institutional guidelines. Peptide treatment was initiated at the time of infection (time 0), by directly injecting 200 µg peptide, dissolved in PBS, into the catheter followed by additional administration of 200 µg peptide injected subcutaneously at four different sites surrounding the catheter at 24 and 48 hours postinfection. Bacterial titers associated with the catheter and surrounding host tissue were evaluated at day 3 (FIG. 13A-13C) and day 14 postinfection (FIG. 13C-13E) to determine the impact of peptide treatment on bacterial burdens. Mice treated with 17BIPHE2 exhibited a significant decrease in bacterial titers on the catheter surfaces (FIGS. 13A and 13D) as well as surrounding tissues compared to vehicle-treated animals (FIGS. 13B and 13D). Importantly, early peptide treatment was key to preventing S. aureus biofilm establishment, since minimal bacterial growth was detected at day 14 following infection even though the last dosing occurred at 48 hours (FIGS. 13B and 13E). As a negative control, LL-23V9, a peptide designed based on the N-terminal 23 residues of LL-37, which is inactive against S. aureus USA300 in vitro (Wang et al. (2012) Biochemistry 51:653-664), was unable to decrease bacterial burdens on biofilm-infected catheters in vivo (FIG. 13C).

Figure 13H:
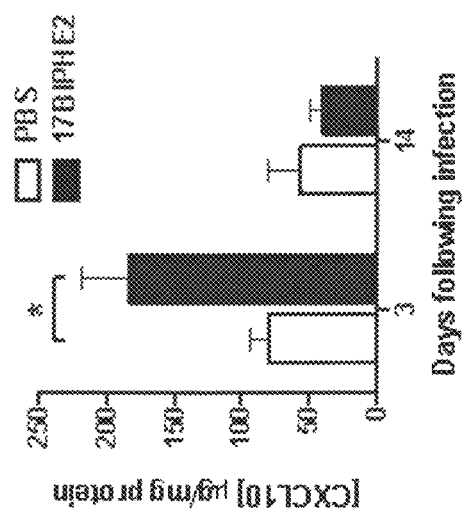
Figure 13G:
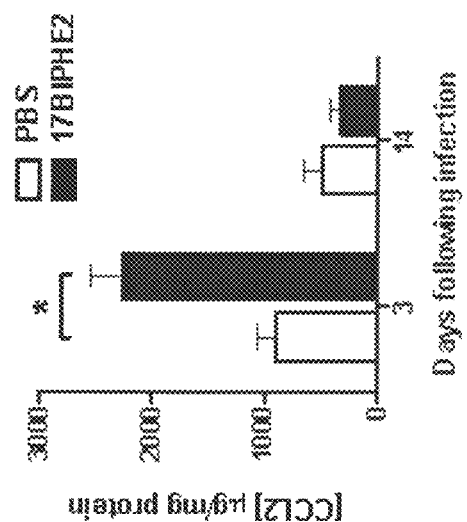

It was then determined whether the peptide had any impact on the host immune response by measuring chemokine levels with and without peptide treatment. 17BIPHE2 significantly increased CCL2 (MCP-1) and CXCL10 (IP-10) expression and reduced IL-10 at day 3 postinfection (FIGS. 13F-13H). This observation is remarkable given that bacterial biofilm formation strongly suppressed CCL2 and increased IL-10 in the same animal model (Thurlow et al. (2011) J. Immunol., 186:6585-6596). Increased CCL2 expression coincided with significantly heightened monocyte recruitment at day 3, which returned to baseline at day 14 postinfection (FIG. 13I). Thus, one mechanism whereby 17BIPHE2 treatment may deter S. aureus biofilm development is through rapid monocyte recruitment. In addition, the expression of CXCL10 might also directly inhibit MRSA based on its known antimicrobial activity (Yung et al. (2011) J. Biol. Chem., 286:5069-5077; Yang et al. (2003) J. Leukocyte Biol., 74:448-455).

In conclusion, human cathelicidin LL-37 was engineered into potent compounds by combining peptide library screening with structure-based design (FIG. 8). The engineered peptides have multiple desired features: in vitro and in vivo efficacy against community-associated MRSA USA300, stability to the action of multiple proteases, and good cell selectivity indices (72-306). The most potent compound 17BIPHE2 appears to kill bacteria by damaging bacterial membranes, which may also involve the access and binding to the intracellular bacterial DNA. Apart from bacterial killing in vivo, 17BIPHE2 can augment host innate immunity to further combat bacterial infection. Combined, these properties make 17BIPHE2 an attractive candidate for the treatment of complicated clinical infections involving biofilms of one or more ESKAPE pathogens, especially in implanted medical devices that cost millions of dollars per year in the USA alone (Darouiche, R. O. (2004) N. Engl. J. Med., 350:1422-1429).

A number of publications and patent documents are cited throughout the foregoing specification in order to describe the state of the art to which this invention pertains. The entire disclosure of each of these citations is incorporated by reference herein.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. An isolated anti-microbial peptide comprising the amino acid sequence $GX_1KRLVQRLKDX_2LRNLV$ (SEQ ID NO: 58); wherein $X_1$ and $X_2$ are hydrophobic amino acids; wherein said peptide comprises a single amino acid substitution with any amino acid at any position other than $X_1$ or $X_2$; wherein said anti-microbial peptide retains anti-microbial activity with said substitution; and wherein said peptide optionally comprises at least one D-amino acid.

2. The isolated anti-microbial peptide of claim 1, wherein $X_1$ and $X_2$ are biphenylalanine.

3. The isolated anti-microbial peptide of claim 1, wherein said peptide comprises at least one D-amino acid.

4. The isolated anti-microbial peptide of claim 1, wherein the amino acids at positions 5, 9, and 13 are D-amino acids.

5. The isolated anti-microbial peptide of claim 1, wherein said peptide further comprises at least one modification selected from the group consisting of amidation and acetylation.

6. A composition comprising at least one anti-microbial peptide of claim 1 and at least one pharmaceutically acceptable carrier.

7. The composition of claim 6, further comprising at least one antibiotic.

8. A method for inhibiting a microbial infection in a subject in need thereof, said method comprising administering to said subject the composition of claim 6.

9. The method of claim 8, further comprising the administration of at least one additional antibiotic.

10. The method of claim 8, wherein said microbial infection is a staphylococcal infection.

11. The method of claim 8, wherein said microbial infection is a methicillin-resistant Staphylococcus aureus (MRSA) infection.

12. An isolated anti-microbial peptide comprising the amino acid sequence selected from the group consisting of SEQ ID NO: 68, SEQ ID NO: 69, and SEQ ID NO: 70.

13. An isolated anti-microbial peptide, wherein the peptide is selected from the group consisting of the peptide consisting of the amino acid sequence of SEQ ID NO: 68, the peptide consisting of the amino acid sequence of SEQ ID NO: 69, and the peptide consisting of the amino acid sequence of SEQ ID NO: 70.

14. The isolated anti-microbial peptide of claim 1, wherein $X_1$ and $X_2$ are each independently selected from the group consisting of trifluoromethylphenylalanine, napthylalanine, and biphenylalanine.

* * * * *